US007994144B2

(12) United States Patent
Symonds et al.

(10) Patent No.: US 7,994,144 B2
(45) Date of Patent: Aug. 9, 2011

(54) PROCESS FOR THE PREPARATION OF A COMPOSITION OF GENETICALLY MODIFIED HEMATOPOIETIC PROGENITOR CELLS

(75) Inventors: Geoffrey P. Symonds, Rose Bay (AU); Rafael Amado, Westlake Village, CA (US); Lun-Quan Sun, Eastwood (AU); Janet Macpherson, Leichhardt (AU); Greg Fanning, Surry Hills (AU); Wayne Gerlach, East Killara (AU)

(73) Assignee: Johnson & Johnson Research Pty, Limited, Eveleigh (AU)

( * ) Notice: Subject to any disclaimer, the term of this patent is extended or adjusted under 35 U.S.C. 154(b) by 996 days.

(21) Appl. No.: 10/483,347

(22) PCT Filed: Jul. 10, 2002

(86) PCT No.: PCT/US02/21907
§ 371 (c)(1),
(2), (4) Date: Nov. 5, 2004

(87) PCT Pub. No.: WO03/006691
PCT Pub. Date: Jan. 23, 2003

(65) Prior Publication Data
US 2005/0063958 A1  Mar. 24, 2005

Related U.S. Application Data

(60) Provisional application No. 60/304,127, filed on Jul. 10, 2001, provisional application No. 60/304,283, filed on Jul. 10, 2001, provisional application No. 60/343,484, filed on Dec. 21, 2001, provisional application No. 60/386,063, filed on Jun. 4, 2002.

(51) Int. Cl.
*A01N 43/04* (2006.01)
*C12N 5/08* (2006.01)
*C12N 15/63* (2006.01)
*C12Q 1/68* (2006.01)
*C07H 21/04* (2006.01)

(52) U.S. Cl. .......... 514/44; 435/6; 435/91.1; 435/91.31; 435/325; 435/455; 536/23.1; 536/24.5

(58) Field of Classification Search .............. 435/6, 91.1, 435/91.31, 325, 455; 514/44; 536/23.1, 536/24.5
See application file for complete search history.

(56) References Cited

U.S. PATENT DOCUMENTS

| 5,026,687 A | 6/1991 | Yarchoan et al. |
|---|---|---|
| 5,500,357 A | 3/1996 | Taira et al. |
| 5,525,468 A | 6/1996 | McSwiggen |
| 5,693,535 A | 12/1997 | Draper et al. |
| 5,712,384 A | 1/1998 | Symonds et al. |
| 5,911,983 A | 6/1999 | Barranger et al. |
| 6,060,317 A * | 5/2000 | Malech .................. 435/456 |
| 6,114,167 A * | 9/2000 | Symonds et al. .......... 435/372.3 |
| 6,287,864 B1 | 9/2001 | Bagnis et al. |
| 2002/0058636 A1 | 5/2002 | Symonds et al. |
| 2003/0082158 A1 | 5/2003 | Symonds et al. |
| 2004/0072771 A1 | 4/2004 | Symonds et al. |
| 2004/0072772 A1 | 4/2004 | Ruggieri et al. |

FOREIGN PATENT DOCUMENTS

| EP | 3/21201 | 6/1989 |
|---|---|---|
| EP | 6/12844 | 8/1994 |
| EP | 1298208 A2 | 4/2003 |
| JP | 2005-521632 | 7/2005 |
| WO | WO 91/04324 | 4/1991 |
| WO | WO 92/17211 | 4/1991 |
| WO | WO 94/00012 | 1/1994 |
| WO | WO 94/16736 | 8/1994 |
| WO | WO 95/04818 | 2/1995 |
| WO | WO 95/18854 | 8/1995 |
| WO | WO 96/22368 | 7/1996 |
| WO | WO 9633281 A1 * | 10/1996 |
| WO | WO 97/47770 | 12/1997 |
| WO | WO 00/34495 | 6/2000 |
| WO | WO 02/059300 | 7/2002 |
| WO | WO 03/006612 | 1/2003 |
| WO | WO 03/006691 | 1/2003 |

OTHER PUBLICATIONS

Bahner et al. (1996) J. Virology 70:4352-4360.*
Amado et al. (1999) Program Abstr. 6th Conf. Retrovir. Oppor. Infect Conf. Retrovir. Oppor. Infect 6th 1999 Chic. III. Jan. 31-Feb. 4, 1999; 6th: 70 (Abstract No. 17).*
Hanenberg et al. (1997) Human Gene Ther. 8:2193-2206.*
Gervaix et al. (1997) Human Gene Ther. 8:2229-2238.*
Perez-Simon et al. (1998) Transfusion 38:385-391.*
Bender et al. (1992) J. Hematotherapy 1:329-341.*
Verma, I.M. et al., Nature, vol. 389, pp. 239-242 (1997).*
File History of U.S. Appl. No. 11/506,722, filed Aug. 18, 2006, Symonds et al.
Abonour, "Efficient retrovirus-mediated transfer of the multidrug resistance 1 gene into autologous human lone-term repopulating hematopoietic stem cells", *Nature Medicine*, vol. 6, No. 6, pp. 652-658 (2000).
Abonour, Abstract #172, [online] 1997 Retrieved from Internet: URL:http://www4.od.nih.gov/oba/rac/hgtprep.asp.
Aguila, H.L., K. Akashi, J. Domen, K.L. Gandy, E. Lagasse, R.E. Mebius, S.J. Morrison, J. Shizuru, S. Strober, N. Uchida, D.E. Wright & I.L. Weissman (1997). "From stem cells to lymphocytes: biology and transplantation." *Immunol. Rev.* 157: 13-40.
Akhtar t al., (1996) "Anti-HIV Therapy with Antisense Oligonucleotides and Ribozymes: Realistic Approaches or Expensive Myths", *J. Antimicrob. Chemother.*, vol. 38, pp. 159-165.
Amado et al. "A Phase I gene therapy clinical study of autologous CD34+cells transduced with an anti-HIV-1 ribozyme," *40th Meeting of the American Society of Hematology*, Miami, 1998.

(Continued)

*Primary Examiner* — Jane Zara
(74) *Attorney, Agent, or Firm* — John P. White; Cooper & Dunham LLP

(57) ABSTRACT

Described are compositions and methods relating to gene therapy, particularly as applied to hematopoietic progenitor (HP) cells, to transduced cells and methods of obtaining them, and to methods of using them to provide prolonged engraftment of modified hematopoietic cells in human subjects. The invention particularly relates to ex vivo gene therapy of HP cells for treatment or prevention of HIV infection.

29 Claims, 21 Drawing Sheets

OTHER PUBLICATIONS

Amado, Rafael, "A phase I trial of autologous CD34+ hematopoietic progenitor cells transduced with Anti-HIV Ribozyme," *Human Gene Therapy*, 1999; 10: 2225-2270.

Amado et al. "Development of genetically protected T-lymphocytes from transduced hematopoietic progenitors in human immunodeficiency virus-1 infected patients," *14th International AIDS Conference*, Barcelona, 2002.

Amado et al. "Multilineage engraftment and preferential survival of ribozyme containing CD4+ T-lymphocytes derived from CD34+ progenitor cells in a phase I study in HIV-1," *5th Am Soc Gener Therapy Meeting*, 2002.

Amado et al., "Effects of Megakaryocyte Growth and Development Factor on Survival and Retroviral Transduction of T Lymphoid Progenitor Cells", *Human Gene Therapy* 9:173-183 (1998).

Amado et al., A phase I gene therapy trial of autologous CD34+ cells transduce with an anti-HIV ribozyme, *Conf. Retroviruses Opportunistic Infect*. Jan. 31- Feb. 4, 1999; $6^{th}$ : 70 (abstract No. 17).

Amado, Systemix #261, [online] 1998 pp. 11-13 URL:http://www4.od.nih.gov/oba/rac/hgtprep.asp.

Amado, Systemix #277, [online] 1998 p. 15-16 URL:http://www4.od.nih.gov/oba/rac/hgtprep.asp.

Bai J, Gorantla S, Banda N, Cagnon L, Rossi J, Akkina R. Characterization of anti-CCR5 ribozyme-transduced CD34+ hematopoietic progenitor cells in vitro and in a SCID-hu mouse model in vivo. *Mol Ther*. 2000; 1:244-54.

Baringa,"Ribozymes: Killing the Messenger," *Science* 262:1512 (1993).

Barranger, JA, Scientific Summary #46, [online] 1993 URL:http://www4.od.nih.gov/oba/rac/hgtprep.asp.

Bauer et al., "Gene Therapy for Pediatric AIDS" *Annals of the New York Academy of Sciences*, 2000, vol. 918, pp. 318-329.

Bauer, Scientific Abstract #204 [online] 1997, URL:http://www4/od.nih.gov/oba/rac/hgtprep.asp.

Baum, C.M., I.L. Weissman, A.S. Tsukamoto, A.-M. Buckle and B.Peault (1992) "Isolation of a candidate human hematopoietic stem-cell population." *Proc Natl Acad Sci USA* 89:2804-2808.

Bauer et al., (1997) "Inhibition of Human Immunodeficiency Virus-1 (HIV-1) Replication After Transduction of Granulocyte Colony-Stimulating Factor-Mobilized CD34$^+$ Cells From HIV-1-Infected Donors Using Retroviral Vectors Containing Anti-HIV-1 Genes," *Blood* 89 :2259-2267.

Bender, M.A., Palmer, T.D., Gelinas, R.E. & Miller, A.D. (1987). Evidence that the Packaging Signal of Moloney Murine Leukemia Virus Extends into the gag Region. *J. Virol*., 61, 1639-1646.

Berzal-Herranz, A. et al. "Essential Nucleotide Sequences and Secondary Structure Elements of the Hairpin Ribozyme." *EMBO* 12:2567-2574 (1993).

Bevec, D. et al., "Inhibition of Human Immunodeficiency Virus Type 1 Replication in Human T Cells by Retroviral-Mediated Gene Transfer of a Dominant-Negative Rev Trans-Activator." *Proc. Natl. Acad. Sci*. 89:9870-9874 (1992).

Bischofberger, N. and Wagner, R.W. "Antisense Approaches to Antiviral Agents". *Virology* 3:57-66 (1992).

Amado et al. (1998) "A Phase I gene therapy clinical study of autologous CD34$^+$ cells transduced with an anti-HIV-1 ribozyme," *Blood*, 92 (10), Supplement 1, part 1-2, p. 665a, Abstract # 2743 *40th Meeting of the American Society of Hematology*, Miami.

Bodine et al., (1998) "Improved Amphotropic Retrovirus-Mediated Gene Transfer into Hematopoietic Stem Cells," *Ann NY Acad Sci* 850: 139-50.

Bonyhadi et al., (1997) "RevM10-Expressing T Cells Derived In Vivo from Transduced Human Hematopoietic Stem-Progenitor Cells Inhibit Human Immunodeficiency Virus Replication," *J Virol* 71:4704-16.

Bordignon et al., "Gene Therapy in Peripheral Blood Lymphocytes and bone Marrow for ADA$^-$ Immunodeficient Patients," *Science* vol. 270, 470-475 (1995).

Briones et al., (1999) "Retroviral gene transfer into human hematopoietic cells an in vitro kinetic study," *Haematologica* 84 :483-488.

Buckley, Abstract #446, [online] 2001 Retrieved from Internet: URL:http://www4.od.nih.gov/oba/rac/hgtprep.asp.

Calenda et al., "The Effects of HIV on Hematopoiesis" *European Journal of Haematology*, 1992, 48: 181-186.

Carabasi, Systemix #340 (Protocol 108), [online] 1999 pp. 13-16 URL:http://www4.od.nih.gov/oba/rac/hgtprep.asp.

Carr et al. "A Phase I Gene Therapy Study showing safety, feasibility and sustained survival of anti-HIV-I transduced CD4+ lymphocytes", *6th Conference on Retroviruses and Opportunistic Infections*, Chicago, 1999.

Case et al., (1999) "Stable transduction of quiescent CD34$^+$CD38$^-$ Human hematopietic cells by HIV-1-based lentiviral vectors," *Proc Natl Acad Sci USA* 96:2988-93.

Castanotto, D. et al. (2000). "Human gene therapy and genetically modified stem cells for the treatment of AIDS," Abstract, Third Annual Meeting of the American Society of Gene Therapy.

Cavazzana-Calvo, "Gene Therapy of Human Severe Combined Immunodeficiency (SCID)-X1 Disease," *Science* vol. 288, 669-672 (2000).

Cech et al., "Ribozyme engineering" Curr. Opin. *Structural Biol*. 2:605-609.

Champlin, Scientific Abstract #44, [online] 1993 URL:http://www4.od.nih.gov/oba/rac/hgtprep.asp.

Chatterjee et al., (2001) "Transduction of Primitive Human Marrow and Cord Blood-Derived Hematopoietic Progenitor Cells with Adeno-Associated Virus Vectors," *Blood* 93: 1882-1894.

Chen, C-J. et al., "Inhibition of HIV-1 Replication by Novel Multitarget Ribozymes". *Ann. N.Y. Acad. Sci*. 660:271-273 (1992).

Chen, C-J. et al., "Multitarget-Ribozyme directed Cleave at up to Nine Highly Conserved HIV-1 env RNA REgions Inhibits HIV-1 Replication-Potential Effectiveness Against Most Presently Sequenced HIV-1 Isolates". *Nucleic Acids Res*. 20:4581-4589 (1992).

Chowrira, B.M. "Four Ribose 2'-Hydroxyl Groups Essential for Catalytic Function of the Hairpin Ribozyme". *J. Biol. Chem*. 268:19458-19462 (1993).

Christoffersen et al. (1995) "Ribozymes as Human Therapeutic Agents", *J. of Med. Chemistry*, vol. 38, pp. 2023-2037.

Chu, "Retrovirus-mediated gene transfer into human hematopoietic stem cells", *J. Mol. Med*. 76:184-192 (1998).

Cohen-Haguenauer et al., (1999) "Efficient Transduction of Hemopoietric CD34$^+$ Progenitors of Human Origin Using an Original Retroviral Vector Derived from Fr-MuLV-FB29: in Vitro Assessment," Hum Gene Ther 9:207-16.

Conant, Enzo Therapeutics, Inc. Scientific Abstract #230, [online] URL:http://www.4.od.nih.gov/oba/rac/hgtprep.asp, 1998.

Cooper et al. (1999) "A marker study of therapeutically transduced CD4+ peripheral blood lymphocytes in HIV discordant twins", *Human Gene Therapy*, vol. 10, pp. 1401-1421.

Cournoyer, D. and Caskey, C.T. "Gene Therapy of the Immune System" *Annu. Rev. Immunol*. 11:297-329 (1993).

Cowan, Abstract #143, [online] 1996 URL:http://www4.od.nih.gov/oba/rac/hgtprep.asp.

Crisell, P. et el., "Inhibition of HIV-1 Replication by Ribozymes that Show Poor Activity in vitro" *Nucleic Acids Res*. 21:5251-5255 (1993).

Croop, Scientific Abstract #370, [online] 2000 URL:http://www4.od.nih.gov/oba/rac/hgtprep.asp.

Cui et al., (2002) "Targeting transgene expression to antigen-presenting cells derived from lentivirus-transduced engrafting human hematopoietic stem/progenitor cells," *Blood* 99 :399-408.

Dao et al., (1997) "FL T3 Ligand Preserves the Ability of Human CD34$^+$ Progenitors to Sustain Long-Term Hematopoiesis in Immune-Deficient Mice After Ex Vivo Retroviral-Mediated Transduction," *Blood* 89 :446-456.

Dao et al., (1998) "Reduction in levels of the cyclin-dependent kinase inhibitor p27$^{kip-1}$ coupled with transforming growth factor β neutralization induces cell-cycle entry and increases retroviral transduction of primitive human hematopoietic cells," *Proc Natl Acad Sci USA* 95:13006-11.

Dao et al., (1998) "Adhesion to Fibronectin Maintains Regenerative Capacity During Ex Vivo Culture and Transduction of Human Hematopoietic Stem and Progenitor Cells," *Blood* 92:4612-21.

Dunbar et al., (1996) "Retroviral Mediated Transfer of the cDNA for Human Glucocerebrosidase into Hematopoietic Stem Cells of Patients with Gaucher Disease. A Phase I Study," *Human Gene Ther* 7:231-253.

Dunbar et al., (1998) "Retroviral Transfer of the Glucocerobrosidase Gene into CD34+ Cells from Patients with Gaucher Disease: In Vivo Detection of Transduced Cells without Myeloablation," *Human Gene Ther* 9:2629-2640.

De Feyter, Rob, Technology evaluation: HIV ribozyme gene therapy, Gene Shears Pty Ltd, *Current Opinion in Molecular Therapeutics*, 2000, vol. 2, No. 3, pp. 332-335.

Declaration of Geoffrey P. Symonds, Ph.D. Under 37 C.F.R. §1.132 filed on May 9, 2000 with the United States Patent and Trademark Office in connection with U.S. Appl. No. 08/375,291, pp. 1-3, including Exhibits 1-2, references as Exhibits 1-11 and Exhibits B-G.

Declaration of Geoffrey P. Symonds, Ph.D. Under 37 C.F.R. §1.132 filed on Nov. 28, 2001 with the United States Patent and Trademark Office in connection with U.S. Appl. No. 08/375,291, pp. 1-3, including Exhibit 1, references as Exhibits 1-11 and Exhibits B-G.

Deonarain (1998) *Expert Opin Ther Pat*, vol. 8, pp. 53-69.

Dinauer, Scientific Abstract # 196, [online] 1997 URL:http://www4.od.nih.gov/oba/rac/hgtprep.asp.

Donahue et al."Strong Sequence Conservation Among Horizontally Transmissible, Minimally Pathogenic Feline Leukemia Viruses," *J. Vir.* 62:722 (1988).

Douer, Scientific Abstract #92, [online] 1994 pp. 174-175 URL:http://www4.od.nih.gov/oba/rac/hgtprep.asp.

Dropulic, B. et al., "Ribozymes: Use As Anti-HIV Therapeutic Molecules". *Antisense Res. Dev.* 3:87-94 (1993).

Dropulic, B et al., (1992) *J. Virol.* 66: 1432-1441.

Dunbar et al., "Retrovirally Marked CD34-Enriched Peripheral Blood and Bone Marrow Cells Contribute to Long-Term Engraftment After Autologous Transplantation," *Blood*, vol. 85, No. 11, pp. 3048-3057 (1995).

Dunbar et al., Abstract # 47, [online] 1993 URL:http://www4.od.nih.gov/oba/rac/hgtprep.asp.

Eck et al, 1996, Goodman & Gilman's The Pharmacological Basis of Therapeutics, McGraw-Hill, New York, p. 77-101.

Eglitis and Schneiderman, (1997), "Transduction of Human Hematopoietic Progenitor Cells with Retroviral Vectors Based on the Gibbon Ape Leukemia Virus," Biochem Biophys Res Commun 231:477-80.

Ely et al. "Conducting gene therapy clinical trials—paving a new path in clinical research", *International Clinical Trials Symposium: Improving Health in the New Millennium*, Sydney, 1999.

Ely et al. "Current state of research in HIV infection", Invited Speaker, *Twelfth Annual Meeting International Symposium on Critical Care Medicine*, Trieste, 1997.

Ely et al. "Retrovirus vectors and gene therapy for HIV", Invited Speaker, *Annual Meeting of the Australian Society for Microbiology*, Hobart, 1998.

Ely et al. (1998) "Anti-HIV ribozymes in the inhibition of HIV and AIDS", Invited Review *Biogenic Amines: Special Issue on Gene Therapy*, Ed. R Bertolotti, vol. 1, pp. 113-135.

Fan et al., (2000) "Efficient Adenoviral Vector Transduction of Human Hematopoietic SCID-Repopulating and Long-Term Culture-Initiating Cells," *Hum Gene Ther* 11:1313-27.

Fanning et al. (2000) "Anti HIV ribozymes in the inhibition of HIV and AIDS", Invited Review *Progress in Gene Therapy: Basic and Clinical Frontiers*, Eds. R Bertolotti, SH Parvez and T Nagatsu, VSP Utrecht, pp. 433-454.

Fanning et al. (2002) "Ribozymes as gene therapeutic agents for HIV/AIDS; a potential paradigm shift", Invited Review *Pathogenic Genomics: Impact on Human Health*, Ed. KJ Shaw, Humana Press Inc, Totowa, NJ, pp. 39-51.

Fisher-Adams et al., 1996, *Blood*, vol. 88, No. 2, p. 492-504.

Fehse et al., (1997) "Selective Immunoaffinity-Based Enrichment of CD34+ Cells Transduced with Retroviral Vectors Containing an Intracytoplasmatically Truncated Version of the Human Low-Affinity Nerve Growth Factor Receptor (ΔLNGFR) Gene," *Hum Gene Ther* 8:1815-24.

Gabarre et al., "High-dose therapy and autologous haematopoietic stem-cell transplantation for HIV-1-associated lympohoma", *The Lancet*, vol. 355, pp. 1071-1072 (2000).

Gerlach et al. (1989) "Synthetic Ribozymes for in vivo inactivation of prokaryotic or eukaryotic RNA transcripts", *Chemical Abstracts*, vol. 112, pp. 336-337.

Gerlach et al. (1996) "Ribozymes in HIV gene therapy," *Organisation for Economic Cooperation and Development, Gene Delivery Systems, A state-of-the-Art Review*, pp. 303-307.

Gervaix, "Gene Therapy Targeting Peripheral Blood CD34+ Hematopoietic Stem Cells of HIV-Infected Individuals" *Human Gene Therapy* 8:2229-2238 (1997).

Glimm et al. (1998) "Efficient Serum-Free Retroviral Gene Transfer into Primitive Human Hematopoietic Progenitor Cells by a Defined, High-Titer, Nonconcentrated Vector-Containing Medium," *Hum Gene Ther* 9:771-8.

Goerner et al., (1999) "The Use of Granulocyte Colony—Stimulating Factor During Retroviral Transduction on Fibronectin Fragment CH-296 Enhances Gene Transfer Into Hematopoietic Repopulating Cells in Dogs," *Blood* 94:2287-92.

Goodchild et al., Enhancement of ribozyme catalytic activity by a contigous oligodeoxynucleotide (facilitator) and by 2'-O-methylation, *Nucleic Acids Res*. 20:4607-4612 (1992).

Goodchild et al., "Antisense Antivirals" Antisense Res. Dev. 1: 361-364 (1991).

Gorecki, 2001, "Prospects and Problems of Gene Therapy: an Update," *Expert Opin Emerging Drugs*, 6(2), 187-198.

Grande, A. et al, "Transcriptional Targeting of Retroviral Vectors to the Erythroblastic Progeny of Transduced Hematopoietic Stem Cells" *Gene Therapy, Blood*, 93:3276-6285.

Haas et al., (2000) "Critical Factors Influencing Stable Transduction of Human CD34+ Cells with HIV-1-Derived Lentiviral Vectors," Mol Ther, 2:71-80.

Haase, A.T., Henry, K., Zupancic, M., Sedgewick, G., Faust, R.A., Melroe, H., Cavert, W., Gebhard, K., Staskus, K., Zhang, Z-Q., Dailey, P.J., Balfour, H.H.,Jr., Erice, A. & Perelson, A.S (1996). "Quantitative image analysis of HIV-1 infection in lymphoid tissue," Science, 274, 985-989.

Hacein-Bey S, Gross F, Nusbaum P, Hue C, Hamel Y, Fischer A, Cavazzana-Calvo M. "Optimization of retroviral gene transfer protocol to maintain the lymphoid potential of progenitor cells," *Hum. Gene Ther.* 2001; 12:291-301.

Hoogerbrugge, PM et al, "Bone Marrow Gene Transfer in Three Patients With Adenosine Deaminase Deficiency" *Gene Therapy*, 3:179-183.

Halene, "Gene Therapy Using Hematopoietic Stem Cells: Sisyphus Approaches the Crest", *Human Gene Therapy* 11:1259-1267 (2000).

Han et al. "Inhibition of Moloney Murine Leukemia Virus-Induced Leukemia in Transgenic Mice Expressing Antisense RNA Complementary to the Retroviral Packaging Sequences," PNAS 88:4313 (1991).

Hanenberg et al., (1997) "Optimization of Fibronectin-Assisted Retroviral Gene Transfer into Human CD34+ Hematopoietic Cells," Hum Gene Ther 8:2193-2206.

Harrison and Lever (1992) "The Human Immunodeficiency Virus Type 1 Packaging Signal and Major Splice Donor Region Have a Conserved Stable Secondary Structure," *J. Virol.*, vol. 66, pp. 4144-4153.

Haseloff & Gerlach (1988) "Simple RNA Enzymes with New and Highly Specific Endoribonuclease Activities," *Nature*, vol. 334, pp. 585-591.

Heidenreich, O. and Eckstein F. "Hammerhead Ribozyme-Mediated Cleavage of Long Terminal Repeat RNA of Human Immundeficiency Virus Type 1," *J. Biol. Chem.* 267:1904-1909 (1992).

Hennemann et al., (1999) "Optimization of retroviral-mediated gene transfer to human NOD/SCID mouse repopulating cord blood cells through a systematic analysis of protocol variables," *Exp Hematol* 27:817-825.

Hirsch and D'Aquila (1993), "Therapy for Human Immunodeficiency Virus Infection," *New England J. of Med.*, vol. 328, pp. 1686-1695.

Holodniy, Systemix Abstract #333, [online] 1999 pp. 13-16 URL:http://www4.od.nih.gov/oba/rac/hgtprep.asp.

Homann, M. et al., "Incorporation of the Catalytic Domain of a Hammerhead Ribozyme Into Antisense RNA Enhances Its Inhibitory Effect on the Replication of Human Immunodeficiency Virus Type 1," *Nucleic Acids Res.* 21:2809-2814 (1993).

Ijichi et al., "In vivo induction of human immunodeficiency virus type 1 entry into nucleus-free cells by CD4 gene transfer to hematopoietic stem cells: a hypothetical possible strategy for therapeutic intervention," *Medical Hypothesis*, 2002, vol. 59, No. 1, pp. 24-34.

Imbert et al., (1998) "A neutralizing anti-TGF-β1 antibody promotes proliferation of $CD34^+Thy^-$ peripheral blood progenitors and increases the number of transduced progenitors," *Exp Hematol* 26:374-81.

Israeli Application No. 88683/2 (Abstract only).

Israeli Application No. 98543/2 (Abstract only).

Jennings et al. (1994) DNA-Armed Ribozymes and Minizymes, Chemical Abstracts 121:490.

Jennings et al. (1991) "Minizymes: Oligonucleotide Endonucleases and their use in Disease Treatment", *Chemical Abstracts*, vol. 117, p. 365.

Johnston et al., "Present Status and Future Prospects for HIV Therapies," *Science* 260: 1286-1293 (1993).

Joseph, S. et al. "Substrate Selection Rules for the Hairpin Ribozyme Determined by in Vitro Selection, Mutation, and Analysis of Mismatched Substrates". *Genes and Development* 7:130-138 (1993).

Joseph,S. et al. "Optimization of an Anti-Hairpin Ribozyme by in Vitro Selection" *J. Biol. Chem.* 268: 24515-24518 (1993).

Knop et al. (1998) "Artificial capillary culture: expansion and retroviral transduction of CD4+ T-lymphocytes for clinical application," *Gene Therapy*, vol. 6, pp. 373-384.

Kohn et al. Scientific Abstract #390, [online] (Mar. 2000) URL:http://www4.od.nih.gov/oba/rac/hgtprep.asp.

Kohn et al., "Engraftment of gene-modified umbilical cord blood cells in neonates with adenosine deaminase deficiency," *Nature Medicine*, vol. 1, No. 10, pp. 1017-1023 (1995).

Kohn/Zaia, Scientific Abstract #153 [online] 1996, URL:http://www4/od.nih.gov/oba/rac/hgtprep.asp.

Kohn et al., "T lymphocytes with a normal ADA gene accumulate after transplantation of transduced autologous umbilical cord blood $CD34^+$ cells in ADA-deficient SCID neonates," *Nature Medicine* vol. 4: 775-780 (1998).

Kohn et al., "A Clinical Trial of Retroviral-Mediated Transfer of a *rev*-Responsive Element Decoy Gene Into $CD34^+$ From the Bone Marrow of Human Immunodeficiency Virus-1-Infected Children," *Blood*, vol. 94, No. 1, pp. 368-371 (1999).

Kohn, Scientific Abstract # 147, [online] 1996 URL:http://www4.od.nih.gov/oba/rac/hgtprep.asp.

Krishnan, A. and J. Zaia. 1997. "High Dose Chemotherapy and Autologous Peripheral Stem Cell Transplantation for HIV Lymphomas: A Phase IIa Study of Comparative marking Using a Ribozyme Gene and a Neutral Gene," Human Gene Transfer Protocols Report, Recombinant DNA Advisory Committee, National Institutes of Health, (www4.od.nih.gov/oba/rac/hgtprep.asp).

Krishnon and Zaia (1997) *Non-technical Absract* #218, [online] URL:http://www4.od.nih.gov/oba/rac/hgtprep.asp.

Laurence, J., Enzo Therapies #443, [online] 2001, pp. 1-3 URL:http://www4.od.nih.gov/oba/rac/hgtprep.asp.

Law et al., "Mobilization of Peripheral Blood Progenitor Cells for Human Immunodeficiency Virus-Infected Individuals", *Experimental Hematology*, 1999, vol. 27, pp. 147-154.

Lawrence, D., "RNAi Could Hold Promise in the Treatment of HIV", *The Lancet*, Jun. 8, 2002, vol. 359, p. 2007.

Leavitt et al. (1994) "Transfer of an anti-HIV-1 ribozyme gene into primary human lymphocytes," *Human Gene Therapy*, vol. 5, pp. 1115-1120.

Lee et al. "Expression of Small Interfering RNAs Targeted Against HIV-1 Rev Transcripts in Human Cells," Nature Biotechnology (2002) 19:500-505.

Lee, Benhur, "An Intricate Web: Chemokine Receptors, HIV-1 and Hematopoiesis," *Stem Cells* 1998, vol. 16, pp. 79-88.

Lever at al. (1989) "Identification of a Sequence Required for Efficient Packaging of Human Immunodeficiency Virus Type 1 RNA Into Virions," *J. Vir.*, vol. 63, p. 4085-4087.

Levinsky, R.J. (1989). "Recent advances in bone marrow transplantation," *Clin. Immunol. Immunopathol.* 50(1 Pt 2) : S124-132.

Levy, (1994) "Antiviral Approaches," *HIV and the Pathogenesis of AIDS, ASM Press*, pp. 217-236.

Levy. J. "Pathogenesis of human Immunodefiency Virus Infection," *Microbiol. Rev.* 57:183-289 (1993).

Li et al. "Gene therapy targeting cord blood-derived $CD34^+$ cells from HIV-exposed infants: preclinical studies," *Gene Therapy* (1998) 5:233-239.

Lisziewicz, J. et al., "Inhibition of Human Immunodeficiency Virus Type 1 Replication By Regulated Expression of a Polymeric Tat Activation Response RNA Decoy as a Strategy for Gene Therapy in AIDS," *Proc. Natl. Acad. Sci.* 90:8000-8004 (1993).

Liu et al., (1999) "Engraftment of Hematopoietic Progenitor Cells Transduced with the Fanconi Anemia Group C Gene (*FANCC*)," *Human Gene Ther* 10 :2337-2346.

Liu, "Regulated Expression of a Dominant Negative Form of Rev Improves Resistance to HIV Replication in T Cells," *Gene Therapy* 1:32-37 (1994).

Liu, JM, Abstract #78, [online] 1994 URL:http://www4.od.nih.gov/oba/rac/hgtprep.asp.

Lo, K.M. et al., "Inhibition of Replication of HIV-1 by Retroviral Vectors Expressing tat-Antisense and Anti-tat Ribozyme RNA," *Virology* 190:176-183 (1992).

Lori F. et al., "Rapid Protection Against Human Immunodeficiency Virus Type 1 (HIV-1) Replication Mediated by High Efficiency Nonretroviral Delivery of Genes Interfering with HIV-1 tat and gag," *Gene Therapy* 1:27-31 (1994).

Lowenstein et al. (1997) "Inhibition of Moloney murine leukemia virus (MoMLV) by a retroviral vector LNL6, carrying ribozymes, targeted to the 5' non-coding sequence," *J. Gen. Virol.* vol. 78, pp. 2587-2590.

Lu et al., (1994) "High Efficiency Retroviral-Mediated Gene Transduction into $CD34^+$ Cells Purified from Peripheral Blood of Breast Cancer Patient Primed with Chemotherapy and Granulocyte-Macrophage Colony-Stimulating Factor," *Human Gene Ther* 5 :203-208.

Lu et al., (1996) "Retrovirus-Mediated Gene Expression in Hematopoietic Cells Correlates Inversely with Growth Factor Stimulation," *Human Gene Ther* 7 :2263-2271.

Macpherson et al. (1999) "Ribozymes in gene therapy of HIV-1," Invited Review, *Frontiers in Bioscience*, vol. 4, pp. 497-505.

Malech, Scientific Abstract #104, [online] 1995 URL:http://www4.od.nih.gov/oba/rac/hgtprep.asp.

Malech, Scientific Abstract #231, [online] 1998 URL:http://www4.od.nih.gov/oba/rac/hgtprep.asp.

Malik et al., (1995) "Retroviral-Mediated Gene Expression in Human Myelomonocytic Cells: A Comparison of Hematopoietic Cell Promoters to Viral Promotors," *Blood* 86:2993-3005.

Mann et al. (1985) "Varying the position of a retrovirus packaging sequence results in the encapsidation of both unspliced and spliced RNAs," *J.Vir.*, vol. 54, p. 401-407.

Mar. 22, 2005 Declaration of Geoffrey Symonds Pursuant to 37 C.F.R. §1.132 in connection with U.S. Appl. No. 10/192,058.

Mautino et al., "Gene Therapy of HIV-1 Infection Using Lentiviral Vectors Expressing Anti-HIV Genes," *AIDS Patient Care and STDs*, 2002, vol. 16, No. 1, pp. 11-26.

R.D. McFarland, D.C.Douek, R.A Koup and L.J.Picker (2000). "Identification of a human recent thymic emigrant phenotype." *Proc. Natl. Acad. Sci. USA* 97(8):4215-4220.

W.A. Marasco, S. Chen, J.H. Richardson, U.Ramstedt and S.D. Jones (1998). "Intracellular antibodies against HIV-1 envelope protein for AIDS gene therapy," *Hum. Gene Ther* 9(11): 1627-1642.

Michallet et al., "Transplantation with selected autologous peripheral blood $CD34^+Thy1^+$ hematopoietic stem cells (HSCs) in multiple myeloma: Impact of HSC dose on engraftment, safety, and immune reconstitution," *Experimental Hematology* 28:858-870 (2000).

Migata et al., (1995) "Selection of Transduced $CD34^+$ progenitors and enzymatic correction of cells from Gaucher patients, with bicistronic vectors," *Proc Natl Acad Sci USA* 92 :12075-12079.

Miller et al. "Ex vivo CD34+ stem cell transduction: modulation by cytokines and retrovirus," *Gene Therapy for Hematopoietic Stem Cells in Genetic Disease and Cancer*, Taos, New Mexico, 1996.

Miller et al. "Ex vivo CD34+ stem cell transduction: modulation by cytokines and retrovirus envelope", *Fourth International Symposium, Blood Cell Transplantation*, Adelaide, 1996.

Miyoshi et al., (1999) "Transduction of Human CD34+ Cells That Mediate Long-Term Engraftment of NOD/SCID Mice by HIV Vectors," *Science* 283:682-686.

Moore and MacKenzie, (1999) "Optimizing Conditions for Gene Transfer into Human Hematopoietic Cells," Prog Exp Tumor Res 36:20-49.

Morel et al., "Hematologic Recovery in Mice Transplanted with Bone Marrow Stem Cells Expressing Anti-Human Immunodeficiency Virus Genes" *Human Gene Therapy*, Nov. 20, 1999, vol. 10 pp. 2779-2787.

Mountain, "Gene therapy: the first decade", *Tibtech* vol. 18 pp. 119-128 (2000).

Murray JM, Kaufmann, G, Kelleher, AD, Cooper, DA. (1998) . A model of primary HIV-1 infection. *Mathematical Biosciences*, 154:57-85.

Murray, J et al. (2001). HIV-1 RNA and DNA dynamics during treated and untreated primary HIV-1 infection. 8th Conference on Retroviruses and Opportunistic Infections, Chicago.

Murray et al., (1999) "Optimization of Retroviral Gene Transduction of Mobilized Primitive Hematopoietic Progenitors by Using Thrombopoietin, Flt3, and Kit Ligands and RetroNectin Culture," *Hum Gene Ther* 10:1743-1752.

Murray et al., (2000) "Addition of the Human Interferon β Scaffold Attachment Region to Retroviral Vector Backbones Increases the Level of in Vivo Transgene Expression among Progeny of Engrafted Human Hematopoietic Stem Cells," Hum Gene Ther 11:2039-50.

Murray et al., (1999) "Thrombopoietic, flt3, and kit ligands together suppress apoptosis of human mobilized CD34+ cells and recruit primitive CD34+Thy1+ cells into rapid division," *Experimental Hematol* 27:1019-1028.

Ng et al., (2002) "Selective in vitro expansion and efficient retroviral transduction of human CD34+ CD38− haematopoietic stem cells," *Brit J Haematol* 117:226-237.

Ngok, (2004) Clinical gene therapy research utilizing ribozymes: application to the treatment of HIV/AIDS, *Methods Mol. Biol.*, vol. 252, pp. 581-598.

NIH Recombinant DNA Advisory Committee Meeting, Minutes of Meeting, Sep. 6-7, 2001.

Nolta et al., (1992) "Retroviral Vector-mediated Gene Transfer into Primitive Human Hematopoietic Progenitor Cells: Effects of Mast Cell Growth Factor (MGF) Combined with Other Cytokines," *Exp Hematol* 20:1065-1071.

Novelli et al., 2000 (Abstract #3448) A Phase I Trial of Retroviral-Mediated Gene Therapy of Gaucher Disease, Clinically-Related Gene Therapy Studies 798a.

Novina et al., "siRNA-directed inhibition of HIV-1 infection," *Nature Medicine*, Jul. 2002, vol. 7, No. 8 pp. 681-686.

O'Shaughnessy, Abstract #54, [online] 1993 URL:http://www4.od.nih.gov/oba/rac/hgtprep.asp.

Ohkawa, J. et al., "Importance of Independence in Ribozyme Reactions: Kinetic Behavior of Trimmed and of Simply Connected Multiple Ribozymes wit Potential Activity Against Human Immunodeficiency Virus". *Proc. Natl. Acad.Sci.* 90: 11302-11306 (1993).

Ohkawa, J. et al. (1993) "Multiple Site-Specific Cleavage of HIV RNA by Transcribed Ribozymes from Shotgun-Type Trimming Plasmid," Nucleic Acids Symp. Ser (Eng.) 29:121-122.

Ojwang, J.O. et al., "Inhibition of Human Immunodeficiency Virus Type 1 Expression by a Hairpin Ribozyme". *Proc. Natl. Acad. Sci.* 89:10802-10806 (1992).

Olmsted et al. "Nucleotide Sequence Analysis of Feline Immunodeficiency Virus: Genome Organization and Relationship to Other Lewntiviruses," *PNAS* 86:8088 (1989).

Poeschla et al., "Development of HIV Vectors for Anti-HIV Gene Therapy," *Proceedings of the National Academy of Sciences*, Oct. 1996, vol. 93, pp. 11395-11399.

Poeschla, E.M., Yu, M., Leavitt, M.C. and Wong-Staal, F. (1998) "Methods for treating HIV by gene therapy using ribozymes," *Methods in Molecular Medicine* vol. 11: Therapeutic Applications of Ribozymes (Ed KJ Scanlon) Humana Press USA, p. 65-82.

Quan et al. (1999) "Human CD34+ hematopoietic cells transuced by retrovirus-mediated interferon alpha gene maintains regeneration capacity and engraftment in NOD/SCID mice," *Exp Hematol* 27:1511-8.

Raponi et al. (1999) "Gene delivery technology: non-viral and viral vector systems," Invited Review *Ex Vivo Cell Therapy*, Eds. Schindheilm and Nordon, Academic Press, Chapter 14, pp. 293-322.

Ratner et al. "Complete Nucleotide Sequence of the AIDS Virus, HTLV-III," *Nature* 313:277 (1985).

Reis, (1999) "Enumeration of CD34+ Hematopoietic Precursor Cells: Current Status," *Transplant Proc* 31:2970-2.

Relander et al., (2001) "Retroviral Transduction of human CD34+ cells on fibronectin fragment CH-296 is inhibited by high concentrations of vector containing medium," *J Gene Med* 3:207-218.

Relander et al., (2002) "Oncoretroviral gene transfer to NOD/SCID repopulating cells using three different viral envelopes," *J Gene Med* 4:122-132.

Richman, (1990) "The Clinical Use of Anti-HIV Agents," *Design of Anti-AIDS Drugs*, ed. E. de Clercq, Pharmacochemistry Library, Elsevier, vol. 14, pp. 339-366.

Rigden et al. (1999) "The use of ribozyme gene therapy for the inhibition of HIV replication and its pathogenic sequelae," Invited Review *Intracellular Ribozyme Applications: Principles and Protocols*, Eds. Couture and Rossi, pp. 255-270.

Rigden et al. (2000) "The use of ribozyme gene therapy for the inhibition of HIV replication and its pathogenic sequelae," Invited Review *Current Issues in Molecular Biology*, vol. 2, pp. 61-69.

Romano, "Latest Developments in Gene Transfer Technology: Achievements, Perspectives, and Controversies over Therapeutic Applications," *Stem Cells* 18:19-39 (2000).

Rossi, J.J. et al., "Ribozymes as Anti-HIV-1 Therapeutic Agents: Principles, Applications, and Problems," *AIDS Res. Hum. Retroviruses* 8:183-189 (1992).

Rossi, J.J. et al.; 1999. "A human gene therapy trial of ribozyme gene transduced CD34+ hematopoietic cells," 2nd Annual Meeting of the American Society of Gene Therapy, 1999.

Rossi, J.J. et al, "Catalytic Antisense RNA (Ribozymes): Their Potential and Use as Anti-HIV-1 Therapeutic Agents," *Innov. in Antiviral Dev. & the Detecting of Virus Infection* 312: 95-109, (1992).

Rossi, J.J. et al., "Ribozymes as Therapies for AIDS," *Ann. N.Y. Acad. Sci.* 616:184-200 (1990).

J.J. Rossi, E.M. Cantin, N. Sarver and P.F. Chang (1991). "The potential use of catalytic RNAs in therapy of HIV infection and other diseases," *Pharmac. Ther.* 50(2): 245-254.

Rossi JJ. "Ribozyme therapy for HIV Infection," *Adv. Drug Deliv. Rev.* 2000; 44: 71-8.

Rozenweig et al., (1997) "Intracellular Immunization of Rhesus CD34+ Hematopoietic Progenitor Cells with a Hairpin Ribozyme Protects T Cells and Macrophages From Simian Immunodeficiency Virus Infection," *Blood* 12:4822-4831.

Rovira et al., (2000) "Stable in vivo expression of glucose-6-phosphate dehydrogenase (G6PD) and rescue G6PD deficiency in stem cells by gene transfer," *Blood* 96:4111-4117.

Sadelain et al., "Issues in the Manufacture and Transplantation of Genetically Modified Hematopoietic Stem Cells," *Current Opinion in Hematology*, 2000, vol. 7, pp. 364-377.

Sandhaus et al., "A simplified method of CD34+ cell determination for peripheral blood progenitor cell transplantation and correlation with clinical engraftment", *Experimental Hematology* 26:73-78 (1998).

Santoro, S.W. and G.F. Joyce (1997). "A general purpose RNA-cleaving DNA enzyme," *Proc Natl Acad Sci USA*. 94(9) : 4262-4266.

Sanyal and Schuening, (1999) "Increased Gene Transfer into Human Cord Blood Cells by Centrifugation-Enhanced Transduction in Fibronectin Fragment-Coated Tubes," *Hum Gene Ther* 10:2859-68.

Sarver, N. "Ribozymes as Potential Anti-HIV-1 Therapeutic Agents," *Science* 247:1222-1225 (1990).

Sarver, N. "Ribozymes: A New Frontier in Anti-HIV Strategy," *Antisense Res. Dev.* 1: 373-378 (1991).

Sarver et al. "Ribozymes as Potential Anti-HIV-1 Therapeutic Agents," *Aids Res. Rev.* 2: 259-285 (1992).

Schuening, Scientific Abstract #61, [online] 1993 URL:http://www4.od.nih.gov/oba/rac/hgtprep.asp.

Schilz et al., (1998) "High Efficiency Gene Transfer to Human Hematopoietic SCID-Repopulating Cells Under Serum-Free Conditions," *Blood* 92:3163-71.

Schwartzberg, L.S.,R. Birch, B.Hazelton, K. W. Tauer, P.Lee, Jr., R. Altemose, C. George, R.Blanco, F. Wittlin, J. Cohen, J. Muscato & W.H. West. (1992). "Peripheral blood stem cell mobilization by chemotherapy with and without recombinant human granulocyte colony-stimulating factor," *J Hematother* 1(4):317-327.

Sczakiel, G. and M. Pawlita (1991)."Inhibition of human immunodeficiency virus type 1 replication in human T cells stably expressing antisense RNA." *J. Virol.* 65(1): 468-472.

Sempowski, G.D.,Hale, L.P., Sundy, J.S., Massey, J.M., Koup, R.A., Douek, D.C., Patel, D.D. & Haynes, B.F. (2000). Leukemia inhibitory factor, oncostatin M, IL-6, and stem cell factor mRNA expression in human thymus increases with age and is associated with thymic atrophy, *J. Immunol.* 164, 2180-2187.

Shimayama T. et al., "Cleavage of the Highly Conserved Hairpin-Loop Region of HIV-1 by Synthetic Ribozymes," *Nucleic Acids Symp. Sr.* 29:177-178 (1993).

Sioud, M. (1994) "Tumor Necrosis Factor-Alpha Ribozymes and degradation-resistant RNA derivatives linked to TNF-alpha Ribozymes," *Chemical Abstracts*, vol. 121, p. 127034m.

Slobod et al., (1996) "Mobilization of CD34+ Progenitor cells by granulocyte colony-stimulating factor in human immunodeficiency virus type-1 infected adults," *Blood*, vol. 88 pp. 3329-3335.

Smythe, J, Sun, L-Q, Pyati, J, Gerlach, W and Symonds, G Gene therapy: antisense and ribozyme strategies for HIV-1 infection. Lorne Genome Conference, 1995.

Smythe, J.A., D.Sun, M. Thomson, P.D Markham, M.S.Reitz, R.C. Gallo, and J. Lisziewicz (1994). "A Rev-inducible mutant gag gene stably transferred into T lymphocytes: An approach to gene therapy against human immunodeficiency virus type 1infection," *Proc Natl Acad Sci USA*. 91(9): 3657-3661.

Sorrentino, Scientific Abstract # 446, [online] 2001 <URL:http://www4.od.nih.gov/oba/rac/hgtprep.asp>.

Strayer et al., 2000, "Efficient gene transfer to hematopoietic progenitor cells using SV40-derived vectors," *Gene Therapy*, vol. 7, p. 886-895.

Stull et al. "Antigene, Ribozyme and Aptamer Nucleic Acid Drugs: Progress and Prospects," *Pharm. Res.* 12:465 (1995).

Sullenger, B.A., H.F. Gallardo, G.E. Ungers and E. Gilboa (1990). "Overexpression of TAR sequences renders cells resistant to human immunodeficiency virus replication," *Cell* 63(3): 601-608.

Su et al., (1997) "Hematopoietic Stem Cell-Based Gene Therapy for Acquired Immunodeficiency Syndrome: Efficient Transduction and Expression of RevM10 in Myeloid Cells In Vivo and In Vitro," *Blood* 89:2283-90.

Sutton et al., (1998) "Human Immunodeficiency Virus Type 1 Vectors Efficiently Transduce Human Hematopoietic Stem Cells," *J Virol* 72:5781-8.

Sun et al. "Ribozyme-Mediated Suppression of Moloney Murine Leukemia Virus and Human Immunodeficiency Virus Type I Replication in Permissive Cell Lines," *PNAS* 1994 91: 9715-9719.

Sun, L-Q, Smythe, J, Pyati, J, Gerlach, W and Symonds, G "Ribozyme and antisense constructs confer resistance to HIV-1 infection in hemotopoietic cells," *Lorne Genome Conference*, 1995.

Sun et al. (1995) "Ribozyme and antisense constructs confer resistance to HIV-1 infection in hematooietic cells", Ribozymes: Basic Science and Therapeutic Applications, Keystone Meeting, Abstract: *J. Cell. Biochem.* Supp 19A, p. 223.

Sun et al. (1997) "Anti-HIV ribozymes," Invited Review. *Molecular Biotechnology*, vol. 7, pp. 241-251.

Sun et al. (1998) "The design, production and validation of an anti-HIV type 1 ribozyme," (Invited Review) *Methods in Molecular Medicine*, Therapeutic Applications of Ribozymes, Ed. KJ Scanlon, Humana Press USA, pp. 51-64.

Sun et al. (1999) "Exogenous gene transfer into lymphoid and haematopoietic progenitor cells", Invited Review *Ex Vivo Cell Therapy*, Eds. Schindheilm, K and Nordon, R, Academic Press, Chapter 9, pp. 179-195.

Sun et al. (1999) "Gene Therapy in haematopoietic cells," *Cancer Forum* vol. 23, pp. 2-5.

Sun et al. "A gene therapeutic approach for AIDS: Implications for disease progression," Invited Plenary Speaker, *Fifth International Workshop, HIV Drug Resistance*, Whistler, Canada, 1996.

Sun et al. "A gene therapeutic approach for AIDS: Implications for disease progression," Invited Speaker, *The Boden Conference on Gene Therapy*, Thredbo, 1997.

Sun et al. "A gene therapeutic approach for AIDS: Implications for disease progression," Invited Speaker *Scientific Meeting, Australian Society for Medical Research*, Sydney.

Sun et al. "Ribozyme constructs in a gene therapy approach for AIDS", Invited Speaker, *Gene Therapy of Cancer, AIDS and Genetic Disorders*, Trieste, Italy, 1996.

Sun et al. "The use of ribozyme constructs for a gene therapy approach to AIDS," Invited Speaker, *10th International Biotechnology Symposium*, Sydney, Australia, 1996 (Selected Abstract: *Australasian Biotechnology*, 1996, vol. 6, p. 150).

Sun et al. (1995) "Resistance to human immunodeficiency virus type 1 infection conferred by transduction of human peripheral blood lymphocytes with ribozyme, antisense or polymeric TAR constructs," *Proc. Natl. Acad. Sci. USA*, vol. 92, pp. 7272-7276.

Sun et al. (1995) "Antisense and ribozyme strategies for HIV-1 infection", Invited Review *Drugs New Perspect.*, vol. 8, pp. 325-331.

Sun, et al. (1995) "Target Sequence-Specific Inhibition of HIV-1 Replication by Ribozymes Directed to tat RNA," *Nucleic Acid Res.* vol. 23, pp. 2909-2913.

Sun et al. (1998) "Retroviral delivery of ribozymes," Invited Review *Ribozymes in the Gene Therapy of Cancer* Eds. Scanlon, KJ and Kashani-Sabet, M, pp. 87-100.

Sun, L.Q., Cairns, M.J., Saravolac, E.G., Baker, A., Gerlach, W.L. (2000). "Catalytic nucleic acids: from lab to applications," *Pharmacological Reviews*. vol. 52, pp. 325-347.

Sun, L.-Q., Gerlach, W. and Symonds, G. (1996) "The use of ribozymes to inhibit HIV replication," Invited Review Nucleic Acids & Molecular Biology, 10, 329-342 (Eds. Eckstein, F. and Lilley, D.M.J.), Springer.

Sun et al., "A gene therapeutic approach for AIDS: Implications for disease progression," Invited Speaker *1st Congress of the Federation of Immunological Societies of Asia-Ocean*, Sydney, 1996.

Sun et al., "Ribozyme-based gene therapy approach for the treatment of HIV-1 infection," *XIth International AIDS Conference on AIDS*, Vancouver, Canada, 1996.

Symonds et.al. "Gene therapies for HIV infection," Plenary Speakers *National Center for HIV Epidemiology and Clinical Research Combined Working Group Meeting*, Sydney, 2002.

Symonds et al. "Gene therapy for AIDS: phase I clinical trials," *Meeting of the Aust Soc HIV Medicine*, 1997.

Symonds et al. "Phase I Gene Therapy Clinical Trials utilising CD4+ T lymphocytes or CD34+ stem cells transduced with an anti-HIV ribozyme", *Inaugural Meeting of the Australian Gene Therapy Society*, Melbourne, 1999.

Symonds, et al. "Ribozyme and antisense constructs confer resistance to HIV-1 infection in T lymphocyte cells," Invited Speaker, *Proc. 7th FAOBMB Congress*, Sydney, 1995 (Abstract: Proc. Aust. Soc. Biochem. & Molec. Biol. 27).

Symonds et al. "Ribozyme and antisense constructs confer resistance to HIV-1 isoforms in T lympocyte cells," Invited Speaker, Scientific Meeting Australian Society for Microbiology, Canberra, 1995, (Abstract: *Microbiology Australian* S39.3).

Symonds, G, Sun, L-Q, Pyati, J, Smythe, J and Gerlach, W. "Gene therapeutic approaches to AIDS," *Biotech '94 Biotechnology Against AIDS; From Basic Science to Prevention, Diagnosis and Therapy.*

Symonds, G. "The use of ribozymes as anti-cancer agents: lessons from other systems and approaches," Invited Speaker, *5th Hanson Symposium: Molecular Mechanisms of Oncogenesis*, Adelaide, 1996.

Symonds, G., "Ribozyme Gene therapy for HIV/AIDS patients," Invited Sepaker, *Janssen-Cilag Medical Department Conference*, Sydney 1999—Oral Presentation Only.

Symonds, G., "Case Study How Johnson & Johnson continuously fosters innovation through supporting scientific research with commercial applications B Gene Therapeutic approaches to disease," Invited Speaker, *Technology Commercialisation 2000*, Sydney 2000—Oral Presentation Only.

Symonds, G., "Gene Therapy for HIV: Issues and implications of the approach", Invited Speaker, *Clinical Trials Strategy Conference*, Sydney Apr. 2000 (Brochure only).

Symonds, G., "Inhibition of HIV replication by the use of ribozymes targeted to the genome of HIV," Invited Speaker *Australasian Society of HIV Medicine Conference*, Sydney, Oct. 2002 (Brochure only).

Symonds, G., "Trials and tribulations of the gene transfer process", Invited Speaker *AusBiotech National Biotechnology & Investment Forum*, Melbourne, 2002.

Symonds, G., Guest Editor (1999) Current Status of Gene Therapy (Part 1): Overview Cancer Forum 23, 2.

Systemix Inc. 1998 A Phase 1/11 study of the safety and feasibility of REVM10 or REVM10/antisense POL1 transduced hematopoietic stem cells (HSC) in HIV-1 related non-Hodgkin's lymphoma patients already being treated with high dose chemotherapy and peripheral blood stem cell support.

Takiyama et al. (1998) "Comparison of methods for retroviral mediated transfer of glucocerebrosidase gene to CD34$^+$ hematopoietic progenitor cells," *Eur J Haematol* 61:1-6.

Taylor, N.R. and Rossi J.J., "Ribozyme-Mediated Cleavage of a HIV-1 gag RNA: The Effects of Nontargeted Sequences and Secondary Structure on Ribozyme Cleavage Activity", *Antisense Res. Dev.* 1:173-186 (1991).

Thill, G. et al., "Structural and Sequence Elements Required for the Self-Cleaving Activity of the Hepatitis Delta Virus Ribozyme," *Biochemistry* 32:4254-4262 (1993).

Tisdale, Precis Abstract # 341, [online] 1999 <URL:http://www4.od.nih.gov/oba/rac/hgtprep.asp>.

Todd, A. V., C.J. Fuery, H.L. Impey, T.L. Applegate and M.A. Haughton (2000)."DzyNA-PCR:use of DNAzymes to detect and quantify nucleic acid sequences in a real-time fluorescent format," *Clin Chem* 46(5): 625-630.

Tough, D.F. and J. Sprent (1995). "Life span of naïve and memory T cells," *Stem Cells* 13(3) : 242-249.

Uchida et al., (1998) "HIV, but not murine leukemia virus, vectors mediate high efficiency gene transfer into freshly isolated $G_o/G_1$ human heamtopoietic stem cells," *Proc Natl Acad Sci USA* 95:1939-44.

Uhlmann (1990) "Antisense Oligonucleotides: A New Therapeutic Principle," *Chemical Reviews*, vol. 90, pp. 544-584.

Vassilopoulos et al., (2001) "Gene transfer into murine hematopoietic stem cells with helper-free foamy virus vectors," Blood 98:604-609.

Verma et al. (1997) "Gene Therapy Promises, problems, and Prospects," *Nature*, vol. 389, pp. 239-242.

Walsh, Scientific Abstract #291, [online] 1999 <URL:http://www4.od.nih.gov/oba/rac/hgtprep.asp>.

Wang et al. (1998) "Preclinical Characterization of an Anti tat Ribozyme for Therapeutic Application", *Human Gene Therapy*, vol. 9, pp. 1283-1291.

Weerasinghe, M. et al., "Resistance to Human Immunodeficiency Virus Type 1 (HIV-1) Infection in Human CD4$^+$ Lymphocyte-Derived Cell Lines Conferred by Using Retroviral Vectors Expressing an HIV-1 RNA-Specific Ribozyme," *J. Virol* 65:5531-5534 (1991).

Wilcox et al., (2000) "Intergin αIIb promoter-targeted expression of gene products in megakaryocytes derived from retrovirus-transduced human heamtopoietic," *Blood* 95:3645-52.

Williams et al., (1999) "Retroviral-Fibronectin Interactions in Transduction of Mammalian Cells," Ann NY Acad Sci 872:109-13.

Wright & I.L. Weissman (1997). "From stem cells to lymphocytes: biology and transplantation," *Immunol. Rev.* 157:13-40.

Yamada, O. et al., "Intracellular Immunization of Human T Cells with a Hairpin Ribozyme Against Human Immunodeficiency Virus Type 1", *Gene Therapy* 1:38-45 (1994).

Yu et al. (1995) "Intracellular immunization of human fetal cord blood stem/progenitor cells with a ribozyme against human immunodeficiency virus type 1," *Proc Natl Acad Sci USA* 92:699-703.

Yu et al. (1994) "Progress towards gene therapy for HIV infection," *Gene Therapy*, vol. 1, pp. 13-26.

Yu, M. et al., "A Hairpin Ribozyme Inhibits Expression of Diverse Strains of Human Immunodeficiency Virus Type 1", *Proc. Natl. Acad. Sci.* 90:6340-6344 (1993).

Zack, J.A., Arrigo, S.J., Weitsman, S.R., Go, A.S., Haislip, A. & Chen, I.S. (1990). HIV-1 entry into quiescent primary lymphocytes: molecular analysis reveals a labile, latent viral structure. *Cell* 61, 213-22.

Zaia, J.A. et al. (1998)"One year results after autologous stem cell transplantation using retrovirus-transduced peripheral blood progenitor cells in HIV-infected subjects," American Society Hematology. *Blood*, 92(10), Supplement 1, part 1-2, p. 665a, Abstract #2744, 40th Meeting of the American Society of Hematology, Miami.

Zaia, Non-technical Abstract #218 [online] 1997, URL:http://www4/od.nih.gov/oba/rac/hgtprep.asp.

Zaia, J.A. et al, "Status of Ribozyme and Antisense-Based Developmental Approaches for Anti-HIV-1 Therapy," *Ann. N.Y. Acad. Sci.* 660: 95-106 (1992).

Korbling, Martin, "Peripheral Blood Progenitor Cell Transplantation: A Replacement for Marrow Auto- or Allografts," *Stem Cells* 14:185-195 (1996).

Hacein-Bey-Abina S. et al. "Sustained Correction of X- Linked Severe Combined Immunodeficiency by Ex Vivo Gene Therapy," *N. Engl. J. Med.* 2002; 346(16):1185-1193.

Bahner, et al. (1996) "Transduction of Human CD34+ Hematopoietic Progenitor Cells by a Retroviral Vector Expressing an RRE Decoy Inhibits Human Immunodeficiency Virus Type 1 Replication in Myelomonocytic Cells Produced in Long-Term Culture," *J. Virol.* 70:4352-4360.

Jacque, J-M et al. (2002) "Modulation of HIV-1 Replication by RNA interference," *Nature*, 418: 435-438.

Miller et al. "Ex vivo CD34+ stem cell transduction: modulation by cytokines and retrovirus envelope," *Gene Therapy for Hematopoietic Stem Cells in Genetic Disease and Cancer*, Taos, New Mexico, 1996.

Miller et al. "Ex vivo CD34+ stem cell transduction: modulation by cytokines and retrovirus envelope", *Fourth International Symposium, Blood Cell Transplantation*, Adelaide, 1996.

Sun, et al.., "A Gene Therapeutic Approach for AIDS: Implications for Disease Progression", Invited Speaker, *Seventh International Antiviral Symposium*, Sydney, 1997.

Sun et al. "A gene therapeutic approach for AIDS: Implications for disease progression," Invited Plenary Speaker, *Fifth Workshop on HIV Drug Resistance*, Whistler, Canada, 1996.

Sun et al. "A gene therapeutic approach for AIDS: Implications for disease progression," Invited Speaker, The Boden Conference on Gene Therapy, Thredbo, 1997.

Sun et al. "Ribozyme constructs in a gene therapy approach for AIDS", Invited Speaker, *Gene Therapy of Cancer, AIDS and Genetic Disorders*, Trietste, Italy, 1996.

Sun et al., "A gene therapeutic approach for AIDS: Implications for disease progression," Invited Speaker *1$^{st}$ Congress of the Federation of Immunological Societies of Asia-Oceania*, Adelaide, 1996.

Symonds et al. "Phase I Gene Therapy Clinical Trials utilising CD4+ lymphocytes or CD34+ stem cells transduced with an anti-HIV ribozyme", *Inaugural Meeting of the Australian Gene Therapy Society*, Melbourne, 1999.

Symonds et al. "Ribozyme and antisense constructs confer resistance to HIV-1 infection in T lymphocyte cells," Invited Speaker, Proc. 7th FAOBMB Congress, Sydney, 1995 (Abstract: *Proc. Aust. Soc. Biochem. & Molec. Biol.* 27).

Symonds et al. "Ribozyme and antisense constructs confer resistance to HIV-1 infection in T lymphocyte cells," Invited Speaker, Scientific Meeting Australian Society for Microbiology, Canberra, 1995 (Abstract: *Microbiology Australian S39.3*).

Symonds, G. "The use of ribozymes as anti-cancer agents: lessons from other systems and approaches," Invited Speaker, *5th Hanson Symposium: Molecular Mechanisms of Oncogenesis*, Adelaide, 1996.

International Preliminary Examination Report dated Sep. 20, 2005 for PCT/US02/21713 (WO 03/006612).
International Search Report dated Jul. 17, 2003 for PCT/US02/21713 (WO 2003-006612 A3).
Supplementary Partial European Search Report, issued Sep. 12, 2006 in connection with European Application No. 02749878.1 (PCT/US02/21713).
Supplementary Partial European Search Report, issued Sep. 3, 1999 in connection with European Application No. 95905220.0.
Supplementary Partial European Search Report, issued Sep. 3, 1999 in connection with European Application No. 96900475.3.
Tendeloo, et al. (2001) "Gene therapy: principles and applications to hematopoietic cells," Leukemia 15: 523-544.
Supplementary Partial European Search Report, issued Dec. 19, 2006 in connection with European Application No. 02746963.4 (PCT/US02/21907).
Cavazzana-Calvo et al. (2001) "Gene therapy of sever combined immunodeficiencies," *J. Gene Med.* 3: 201-206.
Zaia, J.A. et al. (1999), "Autologous stem cell transplantation using retrovirus-transduced peripheral blood progenitor cells in HIV-infected subjects." 41st Annual Meeting of the American Society Hematology, New Orleans; Dec. 3-7, 1999; Blood 94(10) Suppl. 1 Part 1, p. 642a (Abstract Only).
Amado et al., (2004) "Anti-Human Immunodeficiency Virus Hematopoietic Progenitor Cell-Delivered Ribozyme in a Phase I Study: Myeloid and Lymphoid Reconstitution in Human Immunodeficiency Virus Type-1-Infected Patients" Human Gene Therapy, 15:251-262.
Zhou et al. (1994) Gene vol. 149 p. 33-39.
Holyoake et al. *Blood Rev.* Jun. 1994;8(2):113-24.
Coulombel *Oncogene.* Sep. 20, 2004;23(43):7210-22.
Civin, C. I., (2000) "Gene Therapy in Clinical Applications" Stem Cells 2000; 18:150-156 (Exhibit 1).
Malech, H. L., et al., (1997) "Prolonged Production of NADPH Oxidase-corrected Granulocytes after Gene Therapy of Chronic Granulomatous Disease" Proc. Natl. Acad. Sci.1997, 94:12133-12138 (Exhibit 2).
International Search Report issued Feb. 29, 1996 for PCT/AU96/00022.
Jul. 9, 2008 Examination Report issued in connection with European Application No. 02746963.4.
Dec. 16, 2008 Official Action issued in connection with Canadian Application 2,180,358.
Jan. 5, 2009 Office Action issued in connection with U.S. Appl. No. 08/375,291.
Hanenberg et al. (1996), "Colocalization of Retrovirus and Target Cells on Specific Fibronectin Fragments Increase Genetic Transduction of Mammalian Cells," Nat. Med. 1996, 2(8):876-882.
Restriction Requirement issued Oct. 31, 2003 in connection with U.S. Appl. No. 10/192,980.
Response to Oct. 31, 2003 Restriction Requirement filed Nov. 28, 2003 in connection with U.S. Appl. No. 10/192,980.
Supplemental Response to Oct. 31, 2003 Restriction Requirement filed Dec. 22, 2003 in connection with U.S. Appl. No. 10/192,980.
Nonfinal Office Action issued Jul. 2, 2004 in connection with U.S. Appl. No. 10/192,980.
Amendment in Response to Jul. 2, 2004 Nonfinal Office Action filed Dec. 4, 2004 in connection with U.S. Appl. No. 10/192,980.
Final Office Action issued Apr. 8, 2005 in connection with U.S. Appl. No. 10/192,980.
Amendment in Response to Apr. 8, 2005 Final Office Action filed Oct. 12, 2005 in connection with U.S. Appl. No. 10/192,980.
Final Office Action issued Jan. 11, 2006 in connection with U.S. Appl. No. 10/192,980.
Amendment in Response to Jan. 11, 2006 Final Office Action filed Mar. 10, 2006 in connection with U.S. Appl. No. 10/192,980.
Advisory Action issued Apr. 3, 2006 in connection with U.S. Appl. No. 10/192,980.
Amendment in Response to Jan. 11, 2006 Final Office Action filed Jul. 14, 2006 in connection with U.S. Appl. No. 10/192,980.
Nonfinal Office Action issued Oct. 30, 2006 in connection with U.S. Appl. No. 10/192,980.
Amendment in Response to Oct. 30, 2006 Nonfinal Office Action filed Mar. 22, 2007 in connection with U.S. Appl. No. 10/192,980.
Notice of Allowance issued Jun. 20, 2007 in connection with U.S. Appl. No. 10/192,980.
Restriction Requirement issued Nov. 5, 2008 in connection with U.S. Appl. No. 11/506,722.
Amendment in Response to Nov. 5, 2008 Restriction Requirement filed Apr. 15, 2009 in connection with U.S. Appl. No. 11/506,722.
Nonfinal Office Action issued Jun. 11, 2009 in connection with U.S. Appl. No. 11/506,722.
Amendment in Response to Jun. 11, 2009 Nonfinal Office Action filed Dec. 15, 2009 in connection with U.S. Appl. No. 11/506,722.
Notice of Allowance issued Mar. 12, 2010 in connection with U.S. Appl. No. 11/506,722.
International Search Report issued Sep. 27, 2002 in connection with International Application PCT/US02/21907.
Written Opinion issued Jun. 10, 2003 in connection with International Application PCT/US02/21907.
International Preliminary Examination Report issued Jan. 26, 2005 in connection with International Application PCT/US02/21907.
Partial European Search Report issued Dec. 19, 2006 in connection with European Patent Application No. 02746963.4.
Supplemental European Search Report issued Feb. 28, 2007 in connection with European Patent Application No. 02746963.4.
Aug. 8, 2007 Communication Under Article 96(2) EPC issued in connection with European Patent Application No. 02746963.4.
Apr. 18, 2008 Response to Office Action Pursuant to Article 94(3) EPC Dated Aug. 8, 2007.
Jul. 9, 2008 Communication Pursuant to Article 94(3) EPC issued in connection with European Patent Application No. 02746963.4.
Jan. 19, 2009 Response to Official Action Pursuant to Article 94(3) EPC Dated Jul. 9, 2008.
May 7, 2009 Summons to Attend Oral Proceedings Pursuant to Rule 115(1) EPC issued in connection with European Patent Application No. 02746963.4.
Sep. 8, 2009 Written Submission in Preparation To/During Oral Proceedings in connection with European Patent Application No. 02746963.4.
Oct. 15, 2009 Communication to Provide the Minutes of Oral Proceedings in connection with European Patent Application No. 02746963.4; and.
Dec. 23, 2009 Reply to Communication From the Examining Division in connection with European Patent Application No. 02746963.4.

* cited by examiner

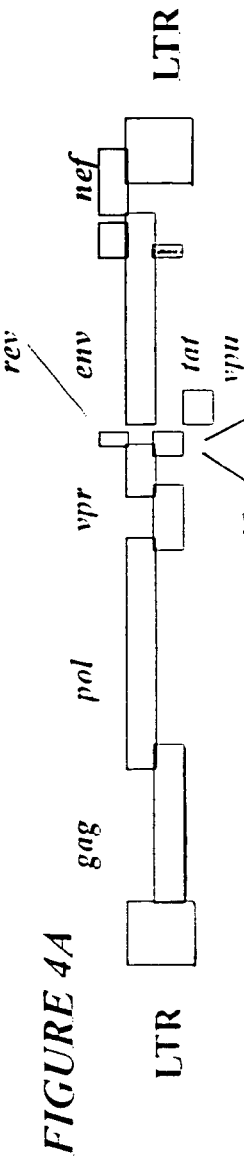
*FIGURE 4A*
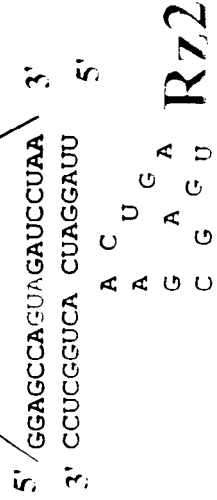
*FIGURE 4B*
*FIGURE 4C*

Self-cleaving RNAi construct with multiple-targeting ability

PROCESS FOR THE PREPARATION OF A COMPOSITION OF GENETICALLY MODIFIED HEMATOPOIETIC PROGENITOR CELLS

This application claims benefit of U.S. Provisional Application No. 60/304,127, filed Jul. 10, 2001, U.S. Provisional Application No. 60/304,283, Jul. 10, 2001, U.S. Provisional Application No. 60/343,484, filed Dec. 21, 2001, and U.S. Provisional Application No. 60/386,063, filed Jun. 4, 2002, the contents of all of which are hereby incorporated by reference.

Throughout this application various publications are referenced in parenthesis. Full citations for these publications may be found listed alphabetically at the end of the specification immediately preceding the claims. The disclosures of these publications in their entireties are hereby incorporated by reference into this application in order to more fully describe the state of the art to which this invention pertains.

FIELD OF THE INVENTION

The present invention relates to gene therapy, particularly as applied to hematopoietic progenitor (HP) cells, to transduced cells and methods of obtaining them, and to methods of using.

BACKGROUND OF THE INVENTION

Gene therapy refers to the use of genetic sequences and their introduction into cells to alter the genetic makeup of the cells and thereby change the properties or functioning of those cells. Gene therapy may be used, for example, to correct a genetic defect by providing to the cells a good copy of a gene that functions as desired, or to provide a gene that encodes an RNA or protein that inhibits an undesired cellular or pathogen activity.

Gene therapy may be aimed at any of a variety of diseases in which there is a genetic aspect. Of particular interest are diseases of the blood or immune systems since the hematopoietic cells are relatively easy to collect from a subject, allowing for ex vivo procedures to be used. These include hemoglobinopathies, defects of leukocyte production or function, immune deficiencies, lysosomal storage diseases and stem cell defects such as Fanconi's anemia, chronic granulomatous disease, Gaucher's disease, G6PD deficiency etc. Many of these disorders have been successfully treated by allogeneic bone marrow cell transplants (Parkman 1986). However, the requirement for immune suppression or the occurrence of immunologic effects such as graft rejection are a disadvantage of allogeneic bone marrow transplantation. Gene therapy of hematopoietic stem cells has been suggested as an alternative means of, treating disease affecting the hematopoietic system in humans.

Despite early promise of success in gene therapy in humans, clinical success has been very difficult to achieve despite a massive effort in the last decade (Mountain, 2000). This is due at least in part to low efficiencies of gene transfer, an inability to modify enough cells, an inability to target appropriate cell types, and a lack of persistence of the desired effect in human subjects.

Gene therapy of human hematopoietic stem (HS) cells has proven to be difficult to carry out in practice (Kohn et al 1998, Halene and Kohn 2000, Kume et al 1999). In most trials in humans, the level of gene-containing peripheral blood leukocytes has been low and these have been short-lived, suggesting a failure to transduce reconstituting HS cells (Bordignon et al 1995, Kohn 1995, Kohn et al 1998, Dunbar et al 1995, Hoogerbrugge et al 1996). This is related in part to the relatively few HS and hematopoietic progenitor (HP) cells in the body (Bertolini et al 1998, Reis 1999) and the requirement that the cells be activated when using some murine retroviral vectors for transduction. This is related to the low level of amphotropic receptors in quiescent human HS cells (Bodine et al 1998). Most human HS cells are quiescent, are relatively slow to respond to stimulation (Hao et al 1996, Gothot et al 1998) and when induced to divide, tend to lose long term repopulating capacity (Traycoff et al 1998). Almost all gene therapy attempts in humans using HS cells have up to now suffered from these two basic problems: insufficient numbers of HS cells that are totipotent and capable of long term engraftment have been transduced in order to have a therapeutic effect, and, secondly, the transduced cells have not persisted to provide modified hematopoietic cells long term.

The most promising trial of gene therapy into human HP cells involved the transfer of a gene into children with X-linked severe combined immunodeficiency (SCID) which led to the reconstitution of an immune system with gene-containing T-lymphocytes (Cavazzana-Calvo et al 2000; Hacein-Bey-Abina et al 2002). That trial used $CD34^+$ cells from bone marrow of pediatric patients (<12 months) and delivered more than $10^6$ transduced cells per kg. The number of $CD34^+$ cells (per kg weight) that can be isolated from children, particularly of low weight, is much higher than in adults. Thymopoiesis is also more active in children. Furthermore, this study is unusual in that thymopoiesis in the SCID-X1 context results only from $CD34^+$ cells that contain the exogenous gene (Cavazzana-Calvo et al 2001). In some ways, this study is analogous to those where myeloablation is carried out in that the infused cells can fill the physiological space that is unoccupied in the SCID patient. Early studies with allogeneic bone marrow transplantation showed that HS cell engraftment was not sustained in patients that were not myeloablated, primarily because of the continued presence of the recipient HS cells (Parkman 1986). Therefore, conclusions drawn from prior engraftment studies using human HS cells in an ablative context cannot be simply transferred to the non-ablative system.

Other reports of human clinical trials for gene therapy of hematopoietic progenitor cells are less positive. Kohn et al 1999 reported results of a clinical trial using bone-marrow derived $CD34^+$ cells from pediatric patients (8-17 yrs) transduced with a gene encoding an RRE decoy (RNA molecule) against HIV. This trial failed to achieve significant transduction and engraftment of progenitor cells. In another trial, patients with breast or ovarian cancer were treated with HP cells after transduction with a marker gene, after myeloablation, but only transient presence of marked cells was observed (Bagnis et al 2002). A clinical trial including three patients with Gaucher disease showed presence of the gene-containing vector in peripheral blood and bone marrow up to 3 months post-infusion but at very low levels (Dunbar et al 1998). In another example, a trial with five patients suffering from Chronic Granulomatous Disease (CGD) was carried out whereby the p47phox gene was introduced into $CD34^+$ cells from peripheral blood. Although corrected neutrophils were found in peripheral blood during the first few months after infusion, they were undetectable at 6 months post-infusion (Malech et al 1997). Further, a trial to correct Fanconi Anemia where the complementation group C gene was inserted into $CD34^+$ cells resulted in only transient detection of the gene in the patients post-infusion (Liu et al 1999).

The poor results in these trials may reflect the lack of a survival advantage of the corrected cells compared to the uncorrected cells, in contrast to the X-linked SCID case. Furthermore, in most of these examples, the manipulated cell populations were administered to patients with no or partial myeloablation, requiring that the transduced cells compete with the resident stem cells to engraft.

Other factors may be operating as well. HS cells can be reduced in number in patients with HIV infection (Marandin et al 1996), making it more difficult to obtain sufficient numbers of such cells. Moreover, HS cells of HIV-infected individuals are compromised in their replication and clonogenic capacities and show an enhanced propensity to apoptosis (Vignoli et al 1998, Zauli et al 1996). Mobilization of peripheral blood HP cells using granulocyte colony-stimulating factor (G-CSF) was demonstrated in HIV-infected individuals (Law et al 1999). Maximal mobilization was achieved after 4 days of G-CSF administration. The leukapheresis product contained approximately $3 \times 10^6$ CD34$^+$ cells per kg. Law et al did not transduce the isolated CD34$^+$ cells nor show that the isolated CD34$^+$ cells were capable of engrafting a subject long term. They merely speculate that gene therapy of HP cells might provide a cure for HIV infection. They also comment that discussion of the number of stem cells required for gene therapy of AIDS is premature because of many uncertainties, including the engraftment potential of the genetically modified cells, the need for chemotherapy, the need for myeloablation or not, the requirement to establish a niche for the infused cells, and the unknown response of the microenvironment in the marrow of AIDS patients after infusion of cells.

The minimum number of CD34$^+$ cells from peripheral blood required for efficient restoration of the hematopoietic system, particularly platelet recovery, in the context of myeloablation has been suggested to be $2.0 \times 10^6$ cells per kg of weight of a subject (Zimmerman 1995). However, the number required for efficient engraftment when not performing myeloablation was unknown prior to this invention. It was unknown whether a "niche" had to be established for the infused cells, or the effect of competing, resident cells in the marrow. As mentioned above, this was particularly true in the context of HIV infection.

Many studies have used model animal systems, particularly in mice, to improve the methods for transduction and increase engraftment. However, although murine HS cells can be efficiently transduced with retroviral vectors, efforts to translate findings from the murine system to applications for human HS cells have revealed major difficulties (Halene and Kohn 2000; Richter and Karlson 2001).

A further difficulty for therapeutic application of gene therapy is in scaling up procedures to obtain sufficient transduced cell numbers (Schilz et al, 2000). Schilz et al measured transduction efficiency and engraftment in a mouse model, but it is unclear how the conclusions might apply to human subjects.

Each of these factors is addressed by the present invention.

SUMMARY OF THE INVENTION

This invention provides a composition suitable for administration to a human subject comprising a pharmaceutically acceptable carrier and at least $1.63 \times 10^6$ CD34$^+$ hematopoietic cells per kg of body weight of the human subject to whom the composition is to be administered, at least $0.52 \times 10^6$ of such CD34$^+$ hematopoietic cells being transduced by a viral construct which expresses an anti-HIV agent.

This invention also provides a method of inserting into hematopoietic cells of a human subject a gene of interest comprising:

a) mobilizing CD34$^+$ hematopoietic progenitor cells into the blood of the human subject;
b) isolating leukocytes from the subject by apheresis;
c) isolating CD34$^+$ hematopoietic cells from the isolated leukocytes by an immunoselective method;
d) subjecting the CD34$^+$ hematopoietic cells of step c) to a transduction process with a gene of interest in the presence of an agent that colocalizes the cells with a transduction vector;
e) determining the total number of CD34$^+$ hematopoietic cells after step d), and if the total number is at least $1.63 \times 10^6$ cells per kg of body weight of the human subject, then proceeding to step f), and if the total number of CD34$^+$ hematopoietic cells after step d) is less than $1.63 \times 10^6$ cells per kg of body weight of the human subject, then performing at least steps b)-d) and combining the CD34$^+$ hematopoietic cells; and
f) delivering to the subject the CD34$^+$ hematopoietic cells, thereby inserting into hematopoietic cells of the human subject a gene of interest.

This invention further provides a use of the composition comprising a pharmaceutically acceptable carrier and at least $1.63 \times 10^6$ CD34$^+$ hematopoietic cells per kg of body weight of a human subject to whom the composition is to be administered, at least $0.52 \times 10^6$ CD34$^+$ of such cells per kg being transduced with a viral construct which expresses an anti-HIV agent, for the manufacture of a medicament for the treatment of the human subject infected with HIV.

This invention yet further provides a kit comprising
a) an amount of an agent capable of mobilizing hematopoietic progenitor cells in a human subject;
b) a culture medium including at least one cytokine acceptable for culturing CD34$^+$ hematopoietic cells;
c) a retroviral vector comprising nucleotides having a sequence that in a cell gives rise to a ribozyme having the sequence 5'-UUA GGA UCC UGA UGA GUC CGU GAG GAC GAA ACU GGC UCC-3' (SEQ ID NO. 1) (Rz2); and
d) tissue culture vessels coated on their inside with a recombinant fibronectin fragment. A package comprising the kit and instructions for its use is also provided by this ideation.

BRIEF DESCRIPTION OF THE FIGURES

FIG. 4. Location of Rz2 target site. A: Schematic of HIV-1 genome showing location of replicative, regulatory and accessory genes. B: Ribozyme sequence together with the complementary target and hybridizing sequence within the tat gene. Cleavage occurs immediately 3' of the triplet GUA. C: Location of the GUA target sequence in the genes encoding Tat and Vpr proteins.

DETAILED DESCRIPTION OF THE INVENTION

Figure 1A:
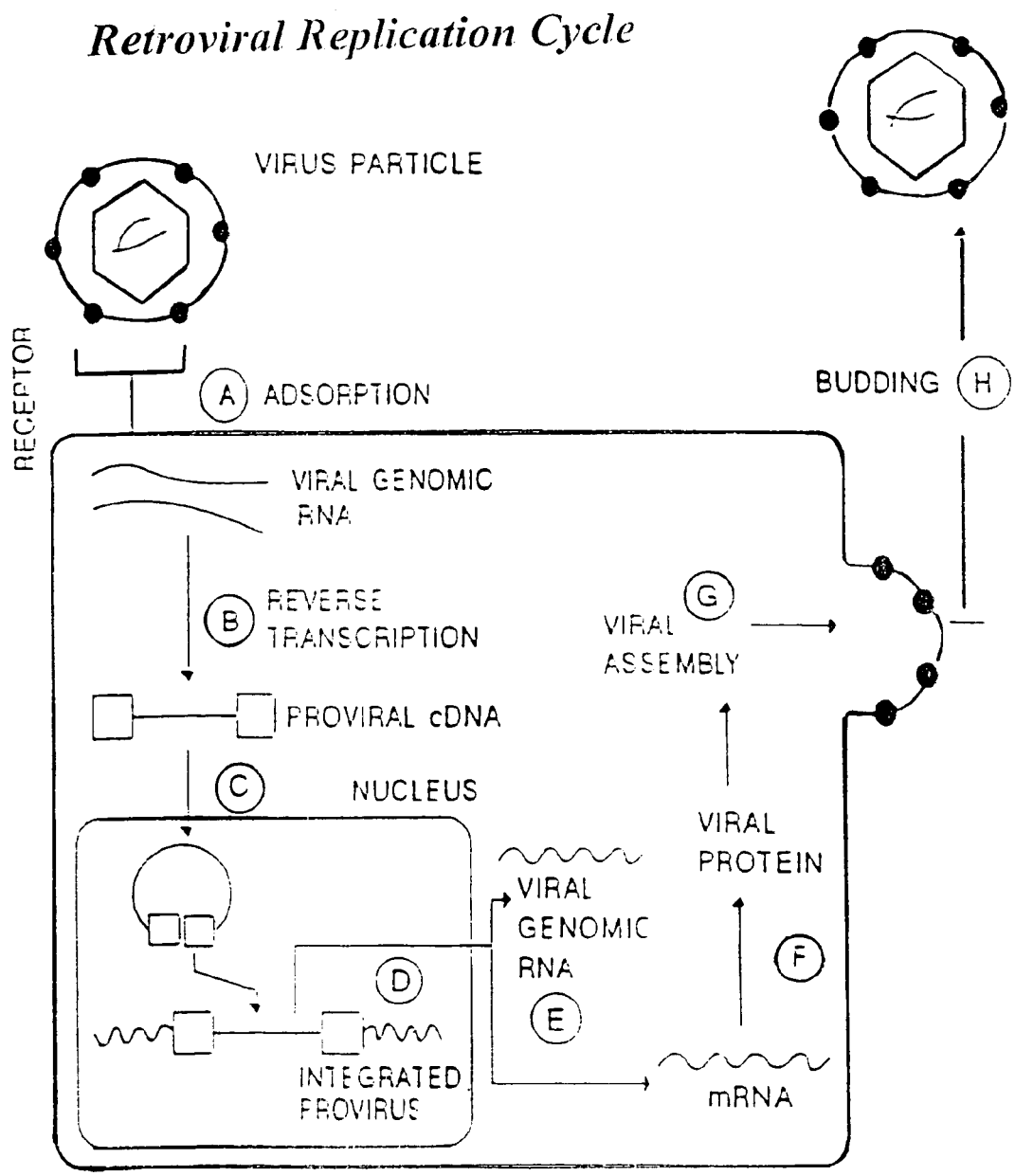
FIG. 1(A). Replication cycle of a typical retrovirus.
A) Virus binds to cell surface receptors on the target cell and the genomic RNA enters the target cell following fusion and viral uncoating.
(B) Reverse transcription occurs resulting in the conversion of viral RNA into cDNA.
(C) cDNA enters the nucleus and is converted into a circular form.
(D) The cDNA then becomes integrated into the host cell genome.
(E) Transcription of the provirus to produce viral RNA and mRNA.
(F) Translation produces viral proteins.
(G) The viral core is formed from the virally encoded proteins and viral RNA packaged.
(H) The core obtains a membrane and exits the cell by budding through the cell membrane.

This invention provides a composition comprising a pharmaceutically acceptable carrier and at least $1.63 \times 10^6$ CD34+ hematopoietic cells per kg of body weight of the human subject to whom the composition is to be administered, at least $0.52 \times 10^6$ of such CD34+ hematopoietic cells being transduced with a viral construct which expresses an anti-HIV agent. Alternatively, the composition comprises at least about $1.7 \times 10^6$ CD34+ hematopoietic cells per kg, at least about $0.5 \times 10^6$ of such cells per kg being transduced with the viral construct. The composition is suitable for administration to a human subject. The human subject may be an adult.

The viral construct may be a retroviral construct. The composition may also be substantially free of cytokines, or substantially free of virus.

This invention also provides a composition where at least $5 \times 10^6$ CD34+ hematopoietic cells per kg of body weight of a human subject to whom the composition is to be administered are transduced; or comprising at least $9.37 \times 10^6$ CD34+ hematopoietic cells per kg of body weight of a human subject, wherein at least $5 \times 10^6$ of such CD34+ hematopoietic cells are transduced; or comprising at least about $10 \times 10^6$ CD34+ hematopoietic cells per kg of body weight where at least $5 \times 10^6$ such cells are transduced; or where the anti-HIV agent is an RNA molecule; or where the anti-HIV agent is an RNAi molecule; or where the anti-HIV agent is an antisense molecule; or where the anti-HIV agent is a ribozyme. The ribozyme may comprise nucleotides having the sequence 5'-UUA GGA UCC UGA'UGA GUC CGU GAG GAC GAA ACU GGC UCC-3' (SEQ ID NO. 1). (Rz2).

In the composition, the transduced CD34+ cells are capable of engraftment, and of giving rise to progeny cells for at least 12 months, in the subject. The cells may be in a primary cell culture.

Also disclosed is a composition comprising a pharmaceutically acceptable carrier and at least $1.63 \times 10^6$ CD34+ hematopoietic cells per kg of body weight of the subject to whom the composition is to be administered, at least $0.52 \times 10^6$ of such CD34+ hematopoietic cells being transduced with a viral construct which expresses an anti-HIV agent,
wherein the composition is produced by a process comprising the steps of:
(a) isolating CD34+ hematopoietic cells from the subject;
(b) culturing the CD34+ hematopoietic cells with at least one cytokine;
(c) transducing the CD34+ hematopoietic cells with the viral construct which expresses the anti-HIV agent in the presence of an agent which enhances colocalization of the cells and the viral construct;
(d) washing the CD34+ hematopoietic cells, and
(e) mixing the CD34+ hematopoietic cells with a pharmaceutically acceptable carrier, to thereby obtain the composition. The composition is suitable for administration to a human subject.

In the composition, the culturing of step (b) may be performed in the presence of at least one cytokine, at least two cytokines or only two cytokines. Step (c) may be performed in the presence of a recombinant fibronectin fragment.

This invention also provides a composition comprising a pharmaceutically acceptable carrier and at least $1.63 \times 10^6$ CD34+ hematopoietic cells per kg of body weight of the human subject to whom the composition is to be administered, at least $0.52 \times 10^6$ CD34+ of such CD34+ hematopoietic cells being transformed with a gene of interest not found in the CD34+ cells prior to transformation. The composition is suitable for administration to a human subject. In this composition, the numbers of cells can be as defined above. The subject may be an adult. In this composition, the gene of interest may express an RNA agent.

This invention yet also provides a composition comprising a pharmaceutically acceptable carrier and at least $1.63 \times 10^6$ CD34+ hematopoietic cells per kg of body weight of a human subject to whom the composition is to be administered, at least $0.52 \times 10^6$ CD34+ of such CD34+ hematopoietic cells being transformed with a gene of interest not found in the CD34+ cells prior to transformation,
wherein the composition is produced by a process comprising the steps of:
(a) isolating CD34+ hematopoietic cells from the subject;
(b) culturing the CD34+ hematopoietic cells with at least one cytokine;
(c) transforming the CD34+ hematopoietic cells with a vector which encodes a gene of interest in the presence of an agent which enhances colocalization of the cells and the vector;
(d) washing the CD34+ hematopoietic cells, and
(e) mixing the CD34+ hematopoietic cells with a pharmaceutically acceptable carrier, to thereby obtain the composition. The composition is suitable for administration to a human subject. In this composition, the numbers of cells can be as defined above. The subject may be an adult. In this composition, the gene of interest may express an RNA agent.

This invention further provides a method of inserting into hematopoietic cells of a human subject a gene of interest comprising:
  a) mobilizing CD34+ hematopoietic progenitor cells into the blood of the human subject;
  b) isolating leukocytes from the subject's blood by apheresis;
  c) isolating CD34+ hematopoietic cells from the isolated leukocytes by an immunoselective method;
  d) subjecting the CD34+ hematopoietic cells of step c) to a transduction process with a gene of interest in the presence of an agent that colocalizes the cells with a transduction vector;
  e) determining the total number of CD34+ hematopoietic cells after step d), and if the total number is at least $1.63 \times 10^6$ cells per kg of body weight of the human subject, then proceeding to step f), and if the total number of CD34+ hematopoietic cells after step d) is less than $1.63 \times 10^6$ cells per kg of body weight of the human subject, then performing at least steps b)-d) and combining the CD34+ hematopoietic cells; and
  f) delivering to the subject the CD34+ hematopoietic cells, thereby inserting into hematopoietic cells of the human subject a gene of interest. The human subject may be an adult.

In the method, the agent that colocalizes the cells with a transduction vector may be a fragment of fibronectin.

In the method, step f) may be performed without myeloablation. Step a) of mobilizing hematopoietic progenitor cells in the subject may be performed by administering to the subject an amount of a cytokine sufficient to mobilize the hematopoietic progenitor cells. In the step of isolating the leukocytes from the subject's blood, apheresis may be performed at least twice.

In the method, the step of subjecting the CD34+ hematopoietic cells to a transduction process with a gene of interest is performed in the presence of a recombinant fibronectin fragment, which may be recombinant fibronectin fragment CH-296.

In the method, the gene of interest may encode an anti-HIV agent. The anti-HIV agent may be an RNA molecule; or an RNAi molecule; or an antisense molecule; or a ribozyme. The ribozyme may comprise nucleotides having the sequence 5'-UUA GGA UCC UGA UGA GUC CGU GAG GAC GAA ACU GGC UCC-3' (SEQ ID NO. 1) (Rz2).

In an embodiment of the method, in step e), if the total number of CD34+ hematopoietic cells after step d) is less than $1.63 \times 10^6$ cells per kg of body weight of the human subject, then further including a step of cryogenically storing the CD34+ hematopoietic cells from step d), repeating steps a)-d), and combining any cryogenically stored cells with the cells from step d). The specific number of cells to be obtained may be increased as described above.

In the method, all or almost all of the CD34+ hematopoietic cells of step e) are delivered to the subject, for example at least 90% of the total number.

The method may further comprise a step of culturing the isolated CD34+ hematopoietic cells of step c) in the presence of at least two cytokines or a cytokine mixture.

The cytokine mixture may comprise one or more cytokines selected from the group consisting of stem cell factor (SCF) megakaryocyte growth and development factor (MGDF), Flt-3 ligand (FL, sometimes abbreviated Flt-3), interleukin 3 (IL-3), granulocyte-macrophage colony stimulating factor (GM-CSF) and thrombopoietin (TPO) The cytokine mixture may further comprise one or more cytokines selected from the group consisting of interleukin 1 (IL-1), interleukin 4 (IL-4), interleukin 5 (IL-5), interleukin 6 (IL-6), interleukin 7 (IL-7), interleukin 9 (IL-9), interleukin 11 (IL-11), interleukin 12 (IL-12), interleukin 15 (IL-15), granulocyte colony stimulating factor (G-CSF), macrophage colony stimulating factor (M-CSF), erythropoietin (EPO), leukemia inhibitory factor (LIF), transforming growth factor beta (TGF-β) macrophage inhibitory protein 1 (MIP-1), tumor necrosis factor (TNF) and stromal cell-derived factor 1 (SDF-1).

In a further embodiment of the method, the cytokine mixture comprises one cytokine selected from a first group and one cytokine selected from a second group, wherein the first group consists of SCF, MGDF, FL, IL-3, GM-CSF, TPO, IL-1, IL-4, IL-5, IL-6, IL-7, IL-9, IL-11, IL-12, IL-15, G-CSF, M-CSF, EPO, LIF, TGF-β, MIP-1, TNF and SDF-1, and wherein the second group consists of MGDF, FL, GM-CSF, TPO, IL-1, IL-4, IL-5, IL-7, IL-9, IL-11, IL-12, IL-15, G-CSF, M-CSF, EPO, LIF, TGF-β, MIP-1, TNF and SDF-1.

This invention further provides a method of inserting into hematopoietic cells of a human subject a gene of interest comprising:
  a) mobilizing CD34+ hematopoietic progenitor cells into the blood of the subject;
  b) isolating leukocytes from the subject's blood by apheresis;
  c) isolating CD34+ hematopoietic cells from the isolated leukocytes by an immunoselective method;
  d) determining the total number of CD34+ hematopoietic cells after step c), and if the total number is at least $1.63 \times 10^6$ cells per kg of body weight of the human subject, then proceeding to step e), and if the total number of CD34+ hematopoietic cells after step c) is less than $1.63 \times 10^6$ cells per kg of body weight of the human subject, then performing steps b)-c) and combining the CD34+ hematopoietic cells;
  e) subjecting the CD34+ hematopoietic cells of step c) to a transduction process with a gene of interest in the presence of an agent that colocalizes the cells with a transduction vector; and
  f) delivering to the subject the CD34+ hematopoietic cells, thereby inserting into hematopbietic cells of the human subject a gene of interest. The relevant specifics of this method may be varied as discussed for the previous methods.

The invention further provides a method of inserting into hematopoietic cells of a human subject a gene that expresses a ribozyme comprising nucleotides having the sequence 5'-UUA GGA UCC UGA UGA GUC CGU GAG GAC GAA ACU GGC UCC-3' (SEQ ID NO. 1) (Rz2) comprising:
  a) mobilizing CD34+ hematopoietic progenitor cells into the blood of the subject by administering to the subject an amount of a cytokine sufficient to mobilize the hematopoietic progenitor cells;
  b) isolating leukocytes from the subject's blood by apheresis, which is performed at least twice;
  c) isolating CD34+ hematopoietic cells from the isolated leukocytes by an immunoselective method;
  d) culturing the isolated CD34+ hematopoietic cells of step c) for about one day in a culture medium in the presence of a cytokine;
  e) subjecting the CD34+ hematopoietic cells of step d) to a transduction process with a retrovirus comprising a vector that gives rise in the cell to a ribozyme comprising nucleotides having the sequence 5'-UUA GGA UCC UGA UGA GUC CGU GAG GAC GAA ACU GGC UCC-3' (SEQ ID NO. 1) (Rz2) in the presence of a recombinant fibronectin fragment;

f) determining the total number of CD34+ hematopoietic cells after step e), and if the total number is at least 1.63×10$^6$ cells per kg of body weight of the human subject, then proceeding to step g), and if the total number of CD34+ hematopoietic cells after step e) is less than 1.63×10$^6$ cells per kg of body weight of the human subject, then again performing steps b)-e) and combining the CD34+ hematopoietic cells; and g) delivering to the subject, without myeloa-blation, the CD34+ hematopoietic cells, thereby inserting into hematopoietic cells of the human subject a gene that expresses the ribozyme. The relevant specifics of this method may be varied as discussed for the previous methods.

Also provided is a method of preparing the compositions described above, comprising:

a) mobilizing CD34+ hematopoietic cells into the blood of the subject;

b) isolating leukocytes from the subject's blood by apheresis;

c) isolating the CD34+ hematopoietic cells from the isolated leukocytes by an immunoselective method;

d) subjecting the CD34+ hematopoietic cells of step c) to a transduction process with a gene of interest in the presence of an agent that colocalizes the cells with a transduction vector; and e) determining the total number of CD34+ hematopoietic cells after step d), and if the total number of CD34+ hematopoietic cells after step d) is less than 1.63×10$^6$ cells per kg of body weight of the human subject, then again performing steps b)-d) and combining the CD34+ hematopoietic cells.

Also provided is a use of a composition comprising a pharmaceutically acceptable carrier and at least 1.63×10$^6$ CD34+ hematopoietic cells per kg of body weight of a human subject to whom the composition is to be administered, at least 0.52×10$^6$ CD34+ of such cells per kg being transduced with a viral construct which expresses an anti-HIV agent, for the manufacture of a medicament for the treatment of the human subject infected with HIV.

Also provided is a kit comprising elements for use in carrying out the described methods. A specific embodiment of a kit comprises a) an amount of an agent capable of mobilizing hematopoietic progenitor cells in a human subject;

b) a culture medium including at least one cytokine acceptable for culturing CD34+ hematopoietic cells;

c) a retroviral vector comprising nucleotides having a sequence that in a cell gives rise to a ribozyme having the sequence 5'-UUA GGA UCC UGA UGA GUC CGU GAG GAC GAA ACU GGC UCC-3' (SEQ ID NO. 1) (Rz2); and d) tissue culture vessels coated on their inside with a recombinant fibronectin fragment.

Yet further provided is a package comprising the described kits and instructions for the use of the kits.

In a further embodiment of the described method, the total combined time taken for the steps of culturing and transducing the CD34+ hematopoietic cells is not more than about three days, that is, the time during which the cells are in a culture medium at 37° C. in the presence of added cytokines (at normal levels) is not more than about three days. Alternatively, the time during which the cells are in culture media in the presence of more than one cytokine is not more than three days. The transduction of the cells may be performed in the presence of a recombinant fibronectin fragment CH-296 or an equivalent agent.

The compositions and methods of this invention can be used to treat any of a variety of diseases in which there is a genetic aspect. Of particular interest are diseases of the blood or immune systems. These include hemoglobinopathies, defects of leukocyte production or function including cancers, immune deficiencies such as HIV, viral infections, lysosomal storage diseases and stem cell defects such as Fanconi's anemia, chronic granulomatous disease, Gaucher's disease, G6PD deficiency etc. They also include infectious diseases such as AIDS/HIV infection or acquired disease such as cancers or cardiovascular diseases.

The present invention relates to gene therapy, particularly as applied to hematopoietic progenitor (HP) cells, to transduced cells and methods of obtaining them, and to methods of using them to provide prolonged engraftment of modified hematopoietic cells in human subjects. The invention particularly relates to ex vivo gene therapy of HP cells for treatment or prevention of HIV infection.

The invention provides compositions of transduced HP cells that comprise sufficient numbers of totipotent cells capable of providing therapeutic benefit. In one embodiment, this invention provides compositions of transduced human HP cells and methods of gene therapy against HIV in order to give rise, in human subjects, to protected T-lymphocytes.

In the context of viral infection, particularly HIV infection, significant therapeutic benefit is provided by the invention through increased long term survival of modified T-lymphocytes in the human subject and thereby increased numbers of T-lymphocytes and improved immune function, leading to lower viral replication and viral load.

In a further embodiment, the transduced human HP cells of the composition or system are capable of long-term engraftment when infused into a patient, giving rise to differentiated hematopoietic cells for at least 12 months after infusion, preferably at least 24 months and even more preferably at least 30 months after infusion. In a further embodiment, the transduced human HP cells are capable of long-term engraftment when infused into an autologous subject. In a further embodiment, the transduced human HP cells are capable of long-term engraftment when infused into a subject without myeloablation.

Another embodiment provides a composition or system comprising transduced human HP cells in sufficient numbers that, when delivered into a human subject, provide long term engraftment at a level such that at least 0.01% gene-modified cells of at least one cell type can be detected in the blood or bone marrow for example, by biopsy. It is preferred that the cell type be T-lymphocytes or macrophages/monocytes. Preferably, the level of gene-modified cells is at least 0.1%, more preferably at least 1% and most preferably at least 10%. It is preferred that the transduced cells are delivered into an autologous subject. It is preferred that the transduced cells are delivered in the absence of myeloablation. It is preferred that long term engraftment occurs for at least 12 months, more preferred at least 24 months, even more preferred, at least 30 months. It is preferred that the transduced gene is for treatment of diseases other than SCID, for example cancers and infectious diseases. It is more preferred that the transduced gene is for treatment or prevention of HIV infection.

The HP cells for transduction were preferably obtained from one subject. The CD34+ purity of the transduced human HP cells (% CD34+) should be at least 65%, preferably at least 90% and more preferably at least 95%. The percentage transduction should be at least about 10%, preferably at least about 30% and more preferably at least about 50%.

In a further embodiment, the transduced human HP cells are derived from CD34+ cells isolated from the blood of a human subject after mobilization of HP cells into the peripheral blood. Mobilization can be achieved by the use of cytokines, preferably one or more from the group consisting of granulocyte colony-stimulating factor (G-CSF), conjugated G-CSF, pegylated G-CSF and granulocyte-macrophage colony-stimulating factor (GM-CSF). The cytokine(s) may further comprise stem cell factor (SCF), interleukin 3 (IL-3), or stromal cell-derived factor-1 (SDF-1, Lataillade et al 2000) or similar acting cytokines. Mobilization may be assisted by the use of a short course of chemotherapy with agents such as cyclophosphamide. More preferably, mobilization is carried out using G-CSF or pegylated G-CSF. The cytokine(s) may be administered daily at an amount of at least about 10 µg per kg of weight of the subject and more preferably at about 30 µg per kg. The $CD34^+$ cells may be collected by apheresis on days 3, 4, 5, 6 or later after beginning cytokine treatment.

Preferably, apheresis is carried out at least twice. The $CD34^+$ cells may be selected by any of the clinical grade devices known in the art such as the Isolex 300i cell selection system or the CEPRATE SC Stem Cell Concentration System.

In a further embodiment, the $CD34^+$ cells are treated prior to transduction with a cytokine mixture, preferably comprising MGDF and SCF, or essentially MGDF and SCF, to induce entry into cell cycle, preferably at concentrations of about 100 ng/ml and 50 ng/ml, respectively. It is preferred that cell cycle induction occur in the absence of added cytokines IL-3, IL-6 or SCF, or the combination of the three of these.

The transduced human HP cells contain an introduced gene which may encode one or more proteins or RNA molecules, for example antisense molecules, RNAi molecules, RNA decoys or ribozyme RNA (ie. RNA agents). The introduced gene may be any introduced gene provided that the encoded protein or RNA or both alter the properties of the transduced human HP cells in a desired way compared to the non-transduced HP cells. In one embodiment, the introduced gene, when expressed, provides resistance to the transduced HP cells or to differentiated progeny of these cells against viral infection, preferably resistance against HIV infection. More preferably, the introduced gene encodes antisense or ribozyme RNA capable of inhibiting HIV-1 replication in cells.

Types of ribozymes which may be directed against viral infection such as HIV-1 infection or against non-viral diseases include the hammerhead, hairpin, RNAse P, hepatitis delta virus (HDV), intervening sequence ribozymes of the Group I or Group II type, or catalytic motifs selected by in vitro selection methods. The ribozymes are preferably hammerhead or hairpin ribozymes, more preferably hammerhead ribozymes. Such ribozymes are capable of cleaving RNA molecules associated with the disease.

The invention includes the use of multiple ribozymes (eg. Ramezani et al 2002), for example a ribozyme with multiple catalytic domains, or a combination of types of ribozymes. This should reduce the likelihood of viral resistance in the case of treatment of virus infection. It is also preferred that the ribozyme cleavage site(s) is highly conserved in the viral target RNA, as is the case for the Rz2 cleavage site. Any combination of the above is also possible, providing more than one mechanism of effect.

The transduced human HP cells of the composition or system are transduced by DNA or a plasmid or viral transfer vector. It is desired that the introduced gene is integrated into the cell genome, after reverse transcription if appropriate. Preferably, the cells are transduced with a retroviral vector, for example a murine retroviral vector or a lentiviral vector. More preferably, the retroviral vector is derived from LNL6 (Bender et al. 1987) or other oncoretroviral vector. In a particular embodiment, the cells are transduced with RRz2.

The introduced gene is expressed in the transduced human HP cells or progeny cells from a promoter. The promoter may be constitutively expressed or inducible, for example being expressed preferentially under favorable conditions or circumstances. The gene may be transcribed by RNA polymerase II (RNA pol II promoters) or by RNA polymerase III.

In another embodiment of the invention, the composition is formulated to be ready for delivery into a human subject. The great majority of cells should be viable for example greater than 95% and preferably greater than 98%. The volume of the composition is preferably from about 10 ml to about 1000 ml, more preferably from about 100 ml to about 500 ml. The composition comprises a pharmaceutically acceptable carrier which is preferably a buffered salts solution comprising a protein agent such as an albumin or gelatine and/or a sugar such as glucose, which agents may act to stabilize the cells. The carrier may contain anticoagulant agents such as sodium citrate. The carrier may comprise a plasma expander, well known in the art. In further aspects, the composition is sterile (bacterial, fungal, mycoplasma), detectably free of bacteria, endotoxin, mycoplasma, HIV p24 antigen or replication-competent retrovirus, substantially free of free transducing vector, or any combination of these. In a further aspect, the composition is substantially free of added cytokines. The composition is administered to the subject by parenteral means, preferably by infusion or injection on one or more occasions.

The invention also provides methods for gene therapy of hematopoietic cells, particularly hematopoietic progenitor cells, using the compositions as described herein. The invention also provides methods of treatment or prevention of genetic or infectious diseases, for example HIV infection. The methods may comprise the use of the CH-296 fragment of human fibronectin (RetroNectin™) or equivalent, or one or more debulking steps to remove unwanted cells, or one or more washing steps.

Gene therapy can be carried out ex vivo or in vivo. The methods described here preferably apply to the ex vivo approach but could also be applied to in vivo approaches (for example, Newbound et al., 2001). The invention can be performed for subjects already having disease, or prophylactically to reduce the occurrence or prevent disease.

HP cells for use in the methods of the invention can be obtained from peripheral blood, bone marrow, umbilical cord blood, or from stem cells that give rise to hematopoietic cells. They are preferably obtained from peripheral blood after mobilization. HP cells can be mobilized into the peripheral blood by administering one or more cytokines, with or without administration of a chemotherapeutic agent. The cytokines may be selected from the group consisting of G-CSF, pegylated G-CSF, conjugated G-CSF, GM-CSF and any combination of the above. The cytokines may further comprise one or more selected from the group consisting of SCF, FL and IL-3.

The methods of the invention are capable of providing at least 0.01% of gene-modified hematopoietic cells long term in a patient in the absence of myeloablation.

The parameters and characteristics of each of the embodiments described above are interchangeable when applicable to each other, and are therefore not repeated. Thus, for example, any parameter or characteristic of the first embodiment may be employed in the other embodiments of the invention.

Definitions

Hematopoietic cells as used herein refer to cells normally found in the blood as well as cells that give rise to cells normally found in the blood, such as cells found in the bone marrow. In this context, "normally" includes the situation where a person is treated to alter the number or quality of cells in the blood or bone marrow.

Viral vector is used herein to mean a vector that comprises all or parts of a viral genome which is capable of being introduced into cells and expressed. Such viral vectors may include native, mutant or recombinant viruses. Such viruses may have an RNA or DNA genome. Examples of suitable viral vectors include retroviral vectors (including lentiviral vectors), adenoviral vectors, adeno-associated viral vectors and hybrid vectors.

A retroviral vector is a viral vector where the virus is from the family retroviridae.

A "construct" is used to mean recombinant nucleic acid which may be a recombinant DNA or RNA molecule, that has been generated for the purpose of the expression of a specific nucleotide sequence(s), or is to be used in the construction of other recombinant nucleic acids. In general, "construct" is used herein to refer to an isolated, recombinant DNA or RNA molecule.

An "anti-HIV agent" as used here refers to any agent that can be expressed by a mammalian cell and which inhibits the replication of HIV or the entry of HIV into the mammalian cell. Such agents may be nucleic acids or polypeptides.

The term "capable of engraftment" is used in here to refer to the ability of a hematopoietic cell to implant into the bone marrow for an extended period of time, e.g. at least one year. Implantation may be detected directly (e.g. by biopsy) or by the production of progeny cells in the blood.

The terms "mobilize" and "mobilized" are used here to refer to hematopoietic cells being moved from the tissue stores in the bone marrow into the peripheral blood.

The term "cytokine" is used to refer to any number of hormone like, low-molecular weight proteins, whether secreted by various cell types or recombinant, that regulate the intensity and duration of cell growth or function, for example cell-to-cell communication. Cytokines are involved, for example, in mediating immunity, allergy, and in regulating maturation and growth of cells.

An "adult" is used here to refer to a fully grown and physically mature human subject. Generally accepted age of a human "adult" is 18 years or more.

Transduction is used to refer to the introduction of genetic material into a cell by using a viral vector.

As used herein a transduced cell results from a transduction process and contains genetic material it did not contain before the transduction process, whether stably integrated or not. As used in some prior art, but not as used herein, "transduced cells" may refer to a population of cells which has resulted from a transduction process and which population includes cells containing the genetic material and cells not containing the genetic material, whether stably integrated or not.

Transfection refers to the introduction of genetic material into a cell without using a viral vector. Examples of transfection include insertion of "naked" DNA or DNA in liposomes, that is without a viral coat or envelope.

Myeloablation refers to treatment, generally chemical or radiological, which results in the destruction of at least a significant part of the myeloid compartment (which includes hematopoietic progenitor cells) in a patient. Myeloablation does not include conditioning treatments which may cause only a minor or unsubstantial destruction of cells of the myeloid compartment.

The phrase "pharmaceutically acceptable carrier" is used to mean any of the standard pharmaceutically acceptable carriers. Examples include, but are not limited to, phosphate buffered saline, physiological saline, and water.

"Recombinant fibronectin fragment" is used to refer to an agent that functions to colocalize the cells with the vector during the transduction process and is based on the activity of fibronectin. For example, RetroNectin™, TaKaRa Shuzo Co. Ltd., is a recombinant fibronectin fragment that contains three domains, a central cell binding domain that binds to integrin VLA-5, a high affinity heparin-binding domain that binds proteoglycans, and a CS-1 site within the alternatively splices IIICS region that binds integrin VLA-4 (Williams 1999). Equivalent retronectins contain three domains that are functionally equivalent to RetroNectin™, while colocalization agents that are similar to RetroNectin™ contain at least two domains that are functionally equivalent.

"Nucleic acid sequence" as used herein refers to an oligonucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Model Proving Principle of Invention

The model selected to prove the principles of the invention is an HIV infected human. An effective, long term and practical treatment or eradication or prevention of HIV infection in a human subject has been an elusive goal. Thus, the advantages of the invention are exemplified in the context of a highly complex problem, i.e. therapy against HIV infection in a human subject.

However, as will be evident from the following description, different diseases can be treated using the compositions or methods of the invention, including any of the blood or immune systems. These include hemoglobinopathies, defects of leukocyte production or function, immune deficiencies, lysosomal storage diseases and stem cell defects such as Fanconi's anemia, chronic granulomatous disease, Gaucher's disease, G6PD deficiency etc. Many of these disorders have been successfully treated by allogeneic HP cell transplants (Parkman 1986). However, the requirement for immune suppression or the occurrence of immunologic effects such as graft rejection or graft-versus host disease are a disadvantage of allogeneic bone marrow transplantation. The invention provides advantages where autologous HP cells are used. The invention can also be used to confer resistance to HP cells or their progeny against myelosuppressive effects.

The invention can also be used to treat infectious disease, such as the exemplified AIDS or other viral infection such as HTLV-1 (Bunnel and Morgan 1998), or acquired diseases such as cardiovascular diseases (for example, see Orlic et al 2001) or cancers. With respect to cancers, bone marrow transplantation techniques have been used for a variety of cancers including those primarily of the hematopoietic system. There is an advantage to providing protection to hematopoietic cells against anti-cancer agents (Carpinteiro et al, 2002), to allow more effective treatment (see review by Brenner 2001). Genes that can be used include the multidrug resistance (MDR) gene which confers resistance to anthracyclines, Vinca alkaloids, podophyllins and taxol, and mutant dihydrofolate reductase (mDHFR)genes to confer resistance to methotrexate or trimetrexate, and genes for O-alkylguanine-DNA-alkyltransferase for resistance to alkylating agents. The gene therapy methods of this invention can be also used in treatment of malignancies by altering the immune response to the cancerous cells or simply by marking cells to monitor the efficacy of conventional therapies (Cornetta et al 1996). For treatment of malignancies where gene therapy of hematopoietic cells is also carried out, partial or complete myeloablation will often be performed prior to delivery of the modified cells.

Gene Therapy for HIV-1

The Human Immunodeficiency Virus (HIV) group includes HIV-1 and HIV-2 types. Replication of HIV-1 is now well understood. The current standard treatment uses a combination of antiretroviral drugs, often three or more, and may provide control of HIV replication in the short-term but is often associated with negative aspects such as drug toxicity, viral resistance, awkward dosing regimes, and cost of treatment.

Using hematopoietic progenitor cells as transduction targets, gene therapy for HIV/AIDS aims to replace a fraction of the HIV-infected cellular pool with cells engineered to inhibit virus replication. This strategy can potentially contribute to virus eradication by protecting $CD4^+$ cells and by allowing the establishment of an antiviral response mediated by protected immune elements. For these strategies to have a positive impact on the course of HIV infection, it is essential that i) a degree of immune reconstitution occur in the setting of HIV infection, ii) the reconstituted immune system be protected against HIV-induced depletion, enabling it to recognize antigen and to protect the host against pathogens. It is desired that this strategy impact on viral load. With regard to the potential for immune reconstitution in HIV infection, several reports have addressed the effects of highly active antiretroviral therapy (HAART) on the immunesystem (Ho et al 1995; Zhang et al 1998). In essence, HAART is associated with increases in $CD4^+$ cell counts, principally due to the expansion of memory cells during the first 4 months of HAART. This is followed by an increase in naïve $CD4^+$ cells, associated with a decrease in CD4 activation markers and an increase in proliferative responses to recall antigens (Autran et al 1997; Pakker et al 1998).

Although in vitro studies have demonstrated that the adult uninfected thymus maintains the ability to support T-lymphopoiesis (Jamieson et al 1999; Poulin 1999), it has not previously been proven that hematopoietic progenitor cell gene therapy can result in the prolonged restoration of the immune system with cells engineered to inhibit HIV-1 replication. With regard to the absence of gene therapy, while the emergence of recent thymic emigrants in the periphery has been described for patients that were previously HAART naïve, it was sustained only as long as viremia was kept in check (Douek et 1998; Zhang et al 1999). It is not known whether a similar response would occur in patients with more advanced HIV infection in the context of drug resistance and uncontrolled viremia. In addition, the source of progenitors that give rise to these recent thymic emigrants has not been elucidated; it is not known whether hematopoietic precursors responsible for the degree of thymopoiesis observed after HAART in adults migrate from the bone marrow to the thymus as a response to T-cell depletion, or whether T-lymphoid development after HAART derives from T-lymphoid progenitors that colonized the thymus earlier in life. Indeed, the ability of peripheral blood progenitor cells to undergo T-lymphocyte development in the adult thymus has not previously been elucidated in the setting of active HIV replication, as the emergence of T-lymphocytes after autologous transplantation of HIV patients could be ascribed to T-lymphocyte development arising from endogenous residual T-lymphocyte precursors (Gabarre et al 2000). Moreover, uninfected adult patients receiving allogeneic hematopoietic progenitor cell transplantation using selected $CD34^+$ cells display marked delay and suboptimal T-lymphocyte recovery, indicating subnormal thymic activity after intensive bone marrow suppression (Behringer et 1999; Martinez et al 1999). It should also be considered that potential factors inherent to the methods employed in genetic manipulation of hematopoietic progenitors might affect their ability to undergo T-lymphoid development. These previously identified factors include the induction of progenitors into cell cycle in preparation for transduction with murine retroviruses (Roe et al 1993), which could result in myeloid lineage commitment, and the presence of a constitutively expressed foreign gene that might interfere with the required processes of progenitor cell migration, homing and differentiation. Therefore we sought to determine whether genetically protected T-lymphocytes, including naïve T-lymphocytes, could be produced in the context of adult HIV infection.

Figure 1B:
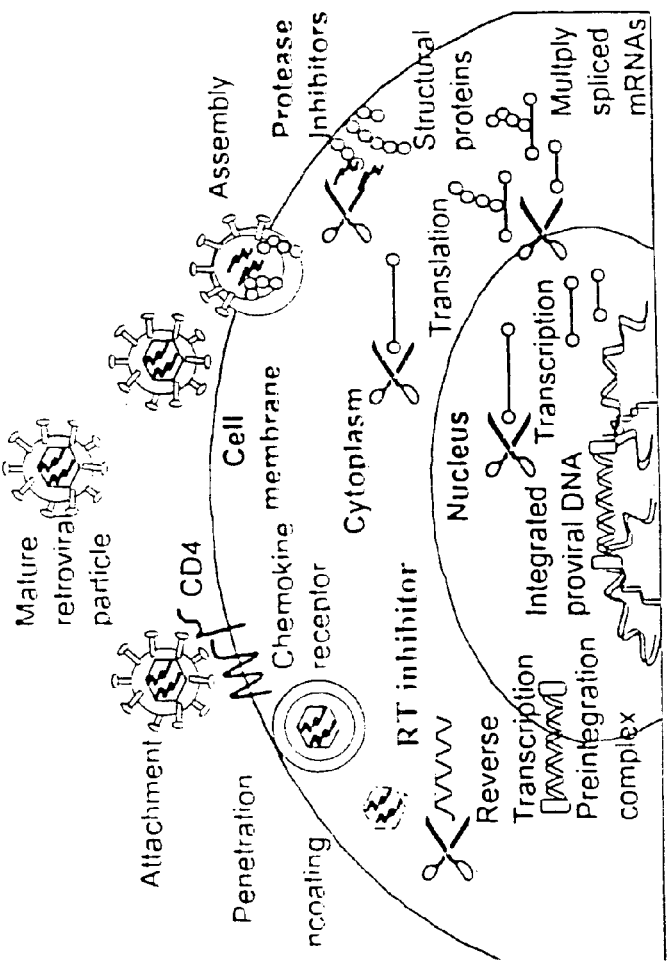
FIG. 1(B). Proposed mode of action of invention. The ribozyme can act at any of several points in the life cycle of the HIV-1 virus. It can cleave the genomic RNA after uncoating and before reverse transcription, or it can cleave viral transcripts in the nucleus or cytoplasm to inhibit translation of viral proteins, or it can cleave newly-formed genomic RNA prior to or during assembly.

Interference with HIV-1 multiplication can occur at any stage of its replication cycle. Retroviral infection of a cell is initiated by the interaction of viral glycoproteins with cellular receptors (A) (see FIG. 1). Following adsorption and uncoating, the viral RNA enters the target cell and is converted into cDNA by the action of reverse transcriptase, an enzyme brought within the virion (B). The cDNA adopts a circular form (C), is converted to double-stranded cDNA and then becomes integrated into the host cell's genomic DNA by the action of integrase (D). Once integrated, proviral cDNA is transcribed from the promoter within the 5' LTR (E). The transcribed RNA including the mRNAs for gag, pol and env and the regulatory factors tat, rev and vpr are translated to produce the viral proteins (F) or is left as nascent viral RNA. This viral RNA contains a Psi packaging sequence which is essential for its packaging into virions (G). Once the virion is produced, it is released from the cell by budding from the plasma membrane (H). In general, retroviruses do not cause lysis of the host cell; HIV is an exception to this. The proviral cDNA remains stably integrated in the host genome and is replicated with the host DNA so that progeny cells also inherit the provirus. Potential anti-viral agents may be targeted at any of these replicative control points. For example, down-regulation of the CCR5 receptor can inhibit HIV-1 replication (Bai et al 2000).

Different types of approaches that can be used with this invention for gene therapy against HIV-1 including intracellular expression of transdominant proteins (eg. Smythe et al. 1994), intracellular antibodies (eg. Marasco et al. 1998, Shaheen et al 1996), antisense ribonucleic acid (RNA) (eg. Sczakiel and Pawlita 1991), viral decoys (eg. Kohn et al. 1999), catalytic ribozymes (eg. Sarver et al. 1990; Sun et al. 1996) and RNAi (eg. Novina et al 2002).

Transdominant (mutant) proteins, particularly mutant Rev or Tat proteins, act by binding to HIV RNA or factors required for HIV replication. They have an altered function compared to the non-mutant protein such that they interfere with the function of the non-mutant protein. They may be a fusion protein, combining two or more activities. In one particular embodiment, the transdominant protein is the RevM10 protein (Ranga et al 1998), which has been shown to inhibit HIV-1 replication in primary T cells. RevM10 transduced CD34$^+$ cells isolated from human umbilical cord blood or peripheral blood gave rise to mature thymocytes in a mouse model and protected T cells against HIV-1 (Bonyhadi et al 1997). Furthermore, retroviral delivery of RevM10 to CD4$^+$ cells protected these cells in HIV-infected individuals (Ranga et al 1998).

Intracellular antibodies, generally of the single-chain type, such as that produced from the retroviral construct pSLX-CMV (Shaheen et al 1996), can inhibit the HIV life cycle by binding or sequestering specific viral proteins. In one particular embodiment, anti-reverse transcriptase (RT) antibody fragments inhibited HIV infection in vitro (Maciejewski et al 1995).

Antisense RNA may bind to viral RNA, either genomic or transcription products, and destabilize the RNA or inhibit processes such as translation or export from the nucleus. Binding to the nascent viral RNA may also act to inhibit productive packaging of RNA into virions. As is well understood in the art, the complementary region for an antisense molecule can be as short as 15 nucleotides, more preferably more than 30 nucleotides, and most preferably between 100 and 500 nucleotides in length. Inhibition of HIV-1 replication has been demonstrated for antisense RNAs targeted against several viral regulatory and structural genes including pol, gag, env, tat, vif, and psi (see Veres et al 1998). Replication of the related simian immunodeficiency virus (SIV) was limited and disease progression was reduced in monkeys after treatment with lymphocytes containing an antisense tat/rev gene (Donahue et al 1998) showing that antisense expression can inhibit *lentivirus* replication in vivo. In one particular embodiment, the retroviral vector HGTV43 encodes an antisense molecule targeting tar and two separate sites of the tat/rev region in the HIV-1 genome. This molecule has been shown to provide protection against HIV infection in vitro.

RNA decoys such as RRE decoys and TAR decoys have also been used to protect cells against HIV (Lee et al 0.1994, Lisziewicz et al 1993) and are preferably used in a polymeric form to increase the ability to bind HIV-1 related proteins and sequester them.

Ribozymes may act not only by binding viral RNAs but also by cleaving and inactivating them and so are attractive for use with this invention. They consist of one or more (usually two) regions of complementarity to the target RNA and a catalytic region that provides enzymatic activity. Ribozymes, particularly those with longer hybridizing arms, may also act through mechanisms similar to those used by antisense molecules. The most widely used ribozyme motifs are the hammerhead and hairpin types, which are described in U.S. Pat. No. 6,127,114 and U.S. Pat. No. 6,221,661, respectively. In one particular embodiment, the retroviral vector pTCAG encodes a hairpin ribozyme targeting the U5 region (position+111/112 from the cap site) of HIV-1 LTR fused with part of an RRE sequence and a ribozyme targeting the rev/env coding region (position 8629-8644 of HXB2 isolate), expressed from a tRNAval promoter (Gervaix et al 1997).

RNAi molecules are those with double stranded RNA regions that trigger host cell RNA degradation mechanisms in a sequence-specific manner. They may therefore be used to inactivate endogenous RNAs or pathogen RNA such as HIV-1 RNA. Each double stranded region may be relatively short, for example 21-25 base pairs in length, preferably less than about 30 base pairs in length and more preferably with a double stranded region of 19 to 25 base pairs. It is preferred that there be not more than one mismatch (mismatches are defined as not including G:U pairs) in each double-stranded region, more preferably no mismatches, and most preferred that the double stranded region(s) be perfectly matched. Where the targeted molecule is variable (eg. HIV-1 RNA), highly conserved regions should be targeted. A family of variants can be targeted provided they do not have more than one mismatch with one or other of the strands of the double-stranded region of the RNAi molecule. For longer RNAi molecules, several short duplexes may be joined, allowing targeting of multiple genes, which is preferred for targets with higher variablity. The RNAi duplexes may also be produced from longer RNA transcripts by splicing or self-cleaving means, for example by incorporating self-cleaving ribozymes between or flanking the duplex regions. RNAi molecules are easily formed from DNA molecules having an inverted repeat structure. Alternatively, RNAi duplexes may be formed from two RNA molecules with complementary regions. RNAi molecules with double-stranded regions of greater than 30 base pairs can be used if they are nuclear localized, eg. if they are made without signals for cytoplasmic export such as polyadenylated sequences. Until recently, RNAi had not been shown to work in human cells. Recently, however, RNAi (also called iRNA, or short siRNA, or hairpin RNA) has been shown to inhibit HIV-1 replication in T lymphocytes (Novina et al 2002). RNAi molecules targeted to the viral LTR, or the accessory vif and nef genes inhibited early and late steps of HIV replication in cell lines and primary lymphocytes (Jacque et al 2002). RNAi has also been successfully targeted to other viruses (eg. Gitlin et al 2002) and can be targeted against endogenous genes.

The RNA agents disclosed herein for use in the invention can be expressed from viral promoters (eg retroviral LTR, cytomegalovirus) or other promoters utilizing RNA polymerase II for high level expression. The RNA agent can be incorporated into longer transcripts, for example in the 3' untranslated region of a marker gene. The transcript may be engineered for self-cleavage for release of the agent. The RNA agent may also be expressed from RNA polymerase III promoters using gene constructs derived from tRNA genes, adenovirus VA1, U1 and U6 or other small nuclear RNA genes. Furthermore, the RNA agent may be provided with signals that aid in colocalizing the agent with the target molecule (for example, see Michienzi et al 2000).

Figure 2:
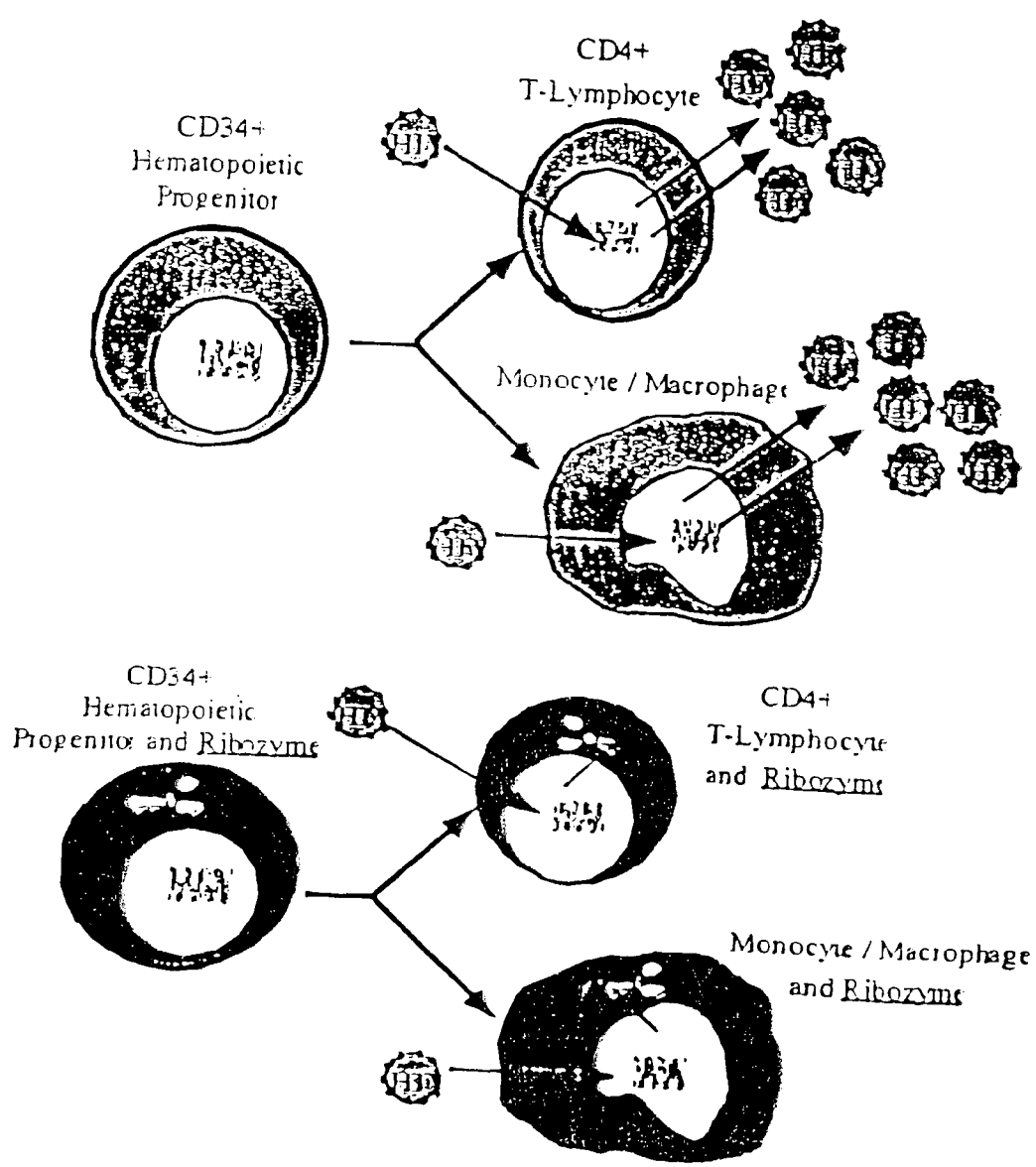
FIG. 2. Scientific rationale for use of ribozyme gene transfer to treat HIV/AIDS. A. Normal CD34+ hematopoietic progenitor cells give rise to lymphocytes and monocytes/macrophages that can be infected by HIV-1 and these infected cells generate HIV-1 particles before dying. B. CD34+ hematopoietic progenitor cells transduced with the ribozyme gene give rise to lymphocytes and monocytes/macrophages that express the ribozyme gene. The therapeutic ribozyme cleaves HIV-1 RNA and inhibits HIV-1 replication in these two key cell types.

The scientific rationale for the use of a ribozyme or other genes to treat HIV or other infection is shown schematically in FIG. 2.

It is an object of this invention to provide therapeutic benefit by allowing for the long term emergence of protected T-lymphocytes from the thymus, with increased survival of the CD4$^+$ cells, and the establishment of an increased immune response by protected immune elements.

Hematopoiesis

Figure 3:
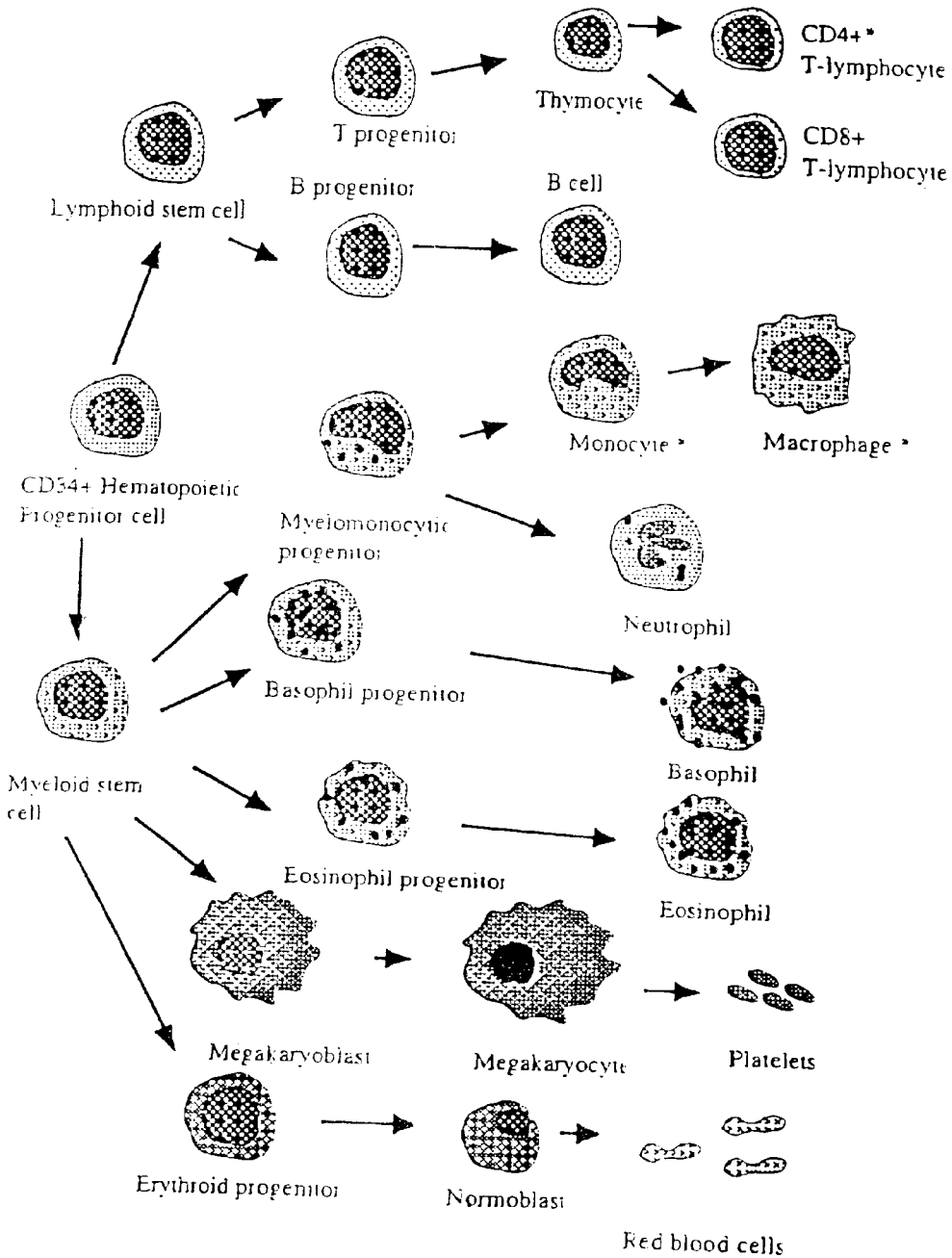
FIG. 3. Schematic of hematopoiesis. The CD34+ hematopoietic progenitor cells give rise to cells of increasing maturity through intermediate progenitor cells. Key cells in terms of HIV/AIDS infection are CD4+ T-lymphocytes and the monocytes/macrophages (asterisked). All of the cells shown schematically are hematopoietic cells.

Hematopoietic cells include cells normally found in the blood as well as cells that give rise to cells normally found in the blood, such as cells found in the bone marrow. In this context, "normally" includes the situation where a person is treated to alter the number or quality of cells in the blood or bone marrow. The process of differentiation of hematopoietic cells is shown schematically in FIG. 3. Hematopoiesis is the process through which the blood-forming system is maintained. This process involves a balance between cell death and regeneration and differentiation of new cells.

Production of mature lymphoid cells requires that precursors leave the bone marrow, pass through the selection mechanisms within the thymus and be exported as naïve cells into the peripheral blood. The efficiency of this process is age related as the thymus involutes with age and its rate of CD4+ T-lymphocyte export decays accordingly. Survival and expansion of T-lymphocytes to give rise to activated and memory T-cells is dependent on natural homeostatic mechanisms.

Hematopoiesis is maintained by a pool of pluripotent hematopoietic stem (HS) cells which have the long term capacity for self-renewal as well as giving rise to progeny which proliferate and differentiate into mature effector blood cells of both the myeloid and lymphoid groups (Ogawa et al 1993, Orlic and Bodine 1994). The numbers of HS cells are maintained by cell division so that these cells are effectively immortal. At least in theory, the whole hematopoietic system could be regenerated from a single HS cell. Many of the HS cells are quiescent in the body (Hodgson and Bradley 1979, Jones et al 1990).

Hematopoietic progenitor (HP) cells are characterized by the presence of the CD34 cell surface antigen and their ability to give rise to multilineage progeny of both the myeloid and lymphoid types. Some $CD34^+$ hematopoietic progenitor cells have the capacity for self-renewal and can be considered true stem cells, while other $CD34^+$ hematopoietic cells may not have the capacity for self-renewal or only a limited capacity. The $CD34^+$ antigen is absent on more mature hematopoiet-ic cells.

The $CD34^+$ cells are themselves heterogenous (Bertolini et al 1998) and can be fractionated into subpopulations based on expression of other markers, for example CD38 (Hogan et al 2002). Human cb34+/CD38− cells, representing about 5% of the $CD34^+$ cell population, were shown to have better long-term reconstituting ability in the SCID mouse model than the $CD38^+$ cells (Hogan et al 2002). Thus, $2.5 \times 10^4$ $CD34^+$/CD38-($CD34^+$/CD38low) cells may be equivalent to $5 \times 10^5$ $CD34^+$ cells. Other markers that can be used to enrich the cell population for cells with long-term reconstituting ability include Thy-1+, CD133+, human KDR+(VEGF receptor), human $ClQR_p^+$, HLA-DR−, and low-level retention of vital dyes such as Rhodamine 123 or Hoechst 33342.

Recent reports indicate that there may be HS cells lacking the CD34 antigen for at least some of the time (Halene and Kohn 2000, Dao and Nolta 2000). Reversible expression of the CD34 marker on murine HS cells has been shown, suggesting that CD34 serves as an activation marker (Sato et al 1999). $CD34^-$ cells have been shown to be capable of multilineage engraftment and to give rise to $CD34^+$ cells (Zanjani et al 1998).

The capacity of the HP cells, which are to be altered by gene therapy according to this invention, to engraft and give rise long term to multilineage differentiated progeny is a critical feature of this invention. This provides for persistence of gene-modified hematopoietic cells in the human subject. This capacity may be assayed by the ability to repopulate the hematopoietic systems of myeloablated animals (Harrison 1980, Harrison 1988) or preferably myeloablated humans, or more preferably non-myeloablated humans. Even more preferably, this capacity is assayed in the context of viral infection such as HIV-1 infection.

HP Cells and Their Isolation

The isolation and purification of human HP cells has been reviewed recently (To et al 1997, Huss 2000, Thomas et al 1999, Sadelain et al 2000).

HP cells for use in gene therapy according to the invention can be isolated from peripheral blood after mobilization, bone marrow, or umbilical cord blood. HP cells may also be obtained from stem cells that give rise to hematopoietic cells.

HP cells are preferably obtained from peripheral blood after mobilization (Huss 2000). There are some advantages in isolating HP cells from mobilized peripheral blood. A higher absolute number of $CD34^+$ cells can be collected from the peripheral blood after mobilization compared to bone marrow or umbilical cord blood, due to the relatively large amount of blood that can be processed. The procedure does not require a general anaesthetic and is associated with reduced hospitalization costs. As is well understood in the art (for example, Fu and Liesveld 2000) that mobilization can be performed by treatment with one or more cytokines, optionally adding a short course of chemotherapy with agents such as cyclophosphamide (Campos et al 1993). HP cells can be mobilized into the peripheral blood using G-CSF (Ho 1993, Lane et al 1995), pegylated G-CSF, conjugated G-CSF, GM-CSF (Siena et al 1989), or any combination of these. Mobilization can be enhanced by combining one or more of these cytokines with others such as stem cell factor (SCF), Flt-3 ligand (Ho et al 1996 abbreviated as Flt3), or interleukin 3 (IL-3; Huhn et al 1996). Mobilization may be enhanced by counteracting stromal cell-derived factor-1 (SDF-1; Ben-boubker et al 2001) or other factors that act negatively to restrict mobilization. Mobilization of peripheral blood HP cells using G-CSF in HIV-infected individuals has been demonstrated by Law et al 1999. Maximal mobilization was achieved after 4 days of G-CSF administration. HP cells may be obtained by apheresis on days 4, 5, 6 or later. Levels of $CD34^+$ cells in the blood may be monitored from about day 3 onward, for example Complete Blood Counts (CBCs), differential and platelet count may be performed daily during cytokine administration to assess the extent of the leucocytosis. The $CD34^+$ cell count is preferably greater than 20 cells/$mm^3$ prior to the start of apheresis.

Apheresis may be carried out with the Cobe Spectra (Gambra), Hemonetics (Domediac), Amicus (Baxter) or equivalent equipment. Apheresis results in a leukocyte population highly enriched in mononuclear cells and depleted for granulocytes, which is desired. If insufficient $CD34^+$ cells are obtained from a first series of mobilization/apheresis, the procedure can be repeated with the same or modified mobilization regime.

Alternatively, apheresis can be repeated. $CD34^+$ cells from the first procedure can be cryopreserved and combined with those from subsequent procedures.

It has been shown that primitive HP cells are reduced or lost in patients with HIV infection (Marandin et al 1996); this makes it more difficult to obtain sufficient numbers of cells in the context of HIV infection.

HP cells can also be isolated from aspirated bone marrow by isolating mononuclear cells (MNC) and purifying $CD34^+$ cells. HP cells can also be isolated from umbilical cord blood (Gluckman 2000). Up to about 200 ml of cord blood can be obtained at birth. Such cells can be cryopreserved and used for successful transduction and transplantation later (Huss 2000). There is evidence that HP cells from umbilical cord blood are more readily transduced and have greater self-renewal potential than those from peripheral blood (Moore and MacKenzie 1999).

Devices have been developed that allow enrichment of $CD34^+$ cells for clinical use, including the Isolex 300i or equivalent. These are based on the recognition of the CD34+ cell surface antigen, which is a transmembrane sialomucin that is expressed on HP cells and on vascular endothelial cells. The methods include immunoselective methods using antibodies with specificity for the CD34 antigen, which antibodies may be tagged with magnetic or fluorescent or other tags that allow selection. Cells may be expressing the CD34 protein internally but this would not allow immunoselection. Only cells expressing the CD34 antigen on the cell surface at same time, allowing access to the antibody, are considered CD34+.

Populations of hematopoietic cells that are highly enriched for CD34+ cells can also be obtained from the sources mentioned above by antigen-depletion strategies, for example to selectively deplete the population of cells expressing lineage-specific markers such as CD2, CD3, CD14, CD16, CD19, CD24, CD56, or CD66b glycoprotein A. This type of strategy allows the isolation of cell populations enriched for CD34⁻ HS cells as well as CD34+ cells. The enriched pool of CD34+ or lineage depleted cells preferably comprises at least 40%, more preferably at least 60% and most preferably at least 80% cells of this type. A balance must be struck between the purity and recovery of the desired cells.

The proportion of CD34+ cells in samples can be determined by flow cytometry methods, for example as done by Bender et al 1991, or immunologic methods. The absolute number and proportion of CD34+ cells can be determined by standardized procedures (Barnett et al 1998, Sandhaus et al. 1998). Absolute nucleated cell counts can be determined by hematological analyzers, or more preferably in single-platform assays, where absolute CD34 counts are produced directly from a single flow cytometric analysis. Enumeration of CD34+ cells and some of the equipment that can be used has recently been reviewed (Reis 1999).

Once isolated, CD34+ cells can be cultured in any suitable medium, well known in the art, in vessels such as flasks or bags, for example the gas-permeable polypropylene bags (Giarratana et al 1998).

There is increasing evidence that most CD34+ cells are involved in short-term but not long term reconstitution, and that only a small fraction of all CD34+ cells have long term multilineage engraftment potential (see Bertolini et al 1998). This raises concern about the enumeration of CD34+ numbers in earlier reports and engraftment potential (Ducos et al 2000). We have shown here that the transduced human CD34+ cells and methods of the invention are capable of providing for long term multilineage engraftment.

Treatment of HP Cells for Transduction with Murine Oncoretroviral Vectors.

Efficient transduction of human HP cells with murine oncoretroviral vectors (for example, those based on MMLV) and some other retroviral vectors requires induction of cell cycle, for example with one or more cytokines (growth factors) (Dao and Nolta 1999) or inhibitors of cell cycle control. The combination of thrombopoietin (TPO), Flt-3 ligand (FL) and Kit ligand (KL, also known as SCF) has been used in vitro (Murray et al 1999, Ng et al 2002). The combination of MGDF, SCF and FL was used in repopulation assays in primates (Wu et al 2000). Amado et al showed that treatment of cells with MGDF and SCF better supported the survival of thymocyte precursor cells than other combinations of factors in a mouse model (Amado et al 1998). IL-3, IL-6, SCF or TPO or combinations thereof have been shown to have beneficial effects on HP cell transduction (Nolta et al 1992, Hennemann et al 1999). The combinations FL/SCF/IL-3/IL-6, SCF/G-CSF, FL/SCF/TPO/IL-6, SCF/G-CSF, FL/SCF/TPO, and FL/SCF/GM-CSF have also been used in large animal models (Richter and Karlson 2001). There is evidence, however, that the combination of IL-3, IL-6 and SCF may impair engraftment (Peters et al 1996). Other approaches to induce cycling of HP cells include the use of inhibitors (eg antisense molecules or antibodies) of p27 (kip1) (Dao et al 1998, Cheng et al 2000) or transforming growth factor beta-1 (Ducos et al 2000, Imbert et al 1998) to increase cell numbers. However, the ability of cells stimulated in any of these ways and then transduced to confer long term engraftment in humans was unknown prior to this invention.

SCF (c-kit ligand) is a cytokine produced mainly by marrow stromal cells and has an important role in the survival and self-renewal of HSC (Lyman and Jacobsen 1998). It also acts as a co-mitogen in the movement of HS cells out of the stem cell pool into progeny. Flt-3 ligand (FL) is a cytokine that binds to a class III receptor tyrosine kinase that is expressed on primitive hematopoietic cells (Lyman and Jacobsen 1998). FL has a synergistic effect with SCF on survival and proliferation of HP cells (Dao et al 1997). Thrombopoietin (TPO) is a ligand for the c-Mpl receptor and is a growth factor involved in early hematopoiesis as well as megakaryocyte and platelet formation (Solar et al 1998). MGDF is a pegylated and truncated form of TPO and acts in a similar fashion to TPO; it may be regarded as functionally equivalent to TPO. Any of these cytokines may be modified, formulated differently or conjugated while still providing an equivalent effect.

Ribozymes

Ribozymes are enzymatic RNAs that can specifically cleave RNA (for example, Haseloff and Gerlach, 1988). Being catalytic, they exhibit turnover and can therefore cleave multiple target molecules. Ribozymes pair with the specific target RNA by virtue of complementary sequence and induce cleavage at specific sites along the phosphodiester backbone of RNA (Haseloff and Gerlach, 1988; Rossi et al., 1992; Hampel et al 1990; Ojwang et al 1992). The hammerhead ribozyme is small, simple and has an ability to maintain site-specific cleavage when incorporated into a variety of flanking sequence motifs (Haseloff and Gerlach, 1988; Rossi et al., 1992). The requirements for cleavage by a ribozyme are an accessible region of RNA and, in the case of the hammerhead ribozyme, a NUH target motif (where N is any ribonucleotide and H is A, C or U ribonucleotides). Cleavage occurs immediately 3' of the NUH target motif. These features make it particularly well suited for gene suppression. Other types of ribozymes include the so-called hairpin ribozyme, hepatitis delta virus ribozyme (HDV), RNAse P, intervening sequence (IVS) Group I, IVS Group II, and motifs identified by in vitro selection methods. The hammerhead and hairpin types are among the smallest and most widely used.

Description of Rz2

A number of studies have demonstrated ribozyme cleavage activity in test tube reactions, and protective effects in tissue culture systems against laboratory and clinical isolates of HIV-1 (Sarver et al. 1990; Sun et al. 1995; Wang et al. 1998). A particular hammerhead ribozyme denoted Rz2 is directed against a highly conserved region of the tat gene (FIG. 4). The tat gene is essential for HIV-1 replication; it encodes and produces the Tat protein that is a transcriptional activator of integrated HIV-1 provirus. Sun et al (1995) used Rz2 to protect T lymphocytes against HIV-1 in vitro but did not describe results in patients. They also did not disclose that a minimum number of transduced HP cells must be used for prolonged engraftment, or what that number might be. Amado et al (1999) describe in general terms the protocol used in a Phase I clinical trial to determine the feasibility and safety of transduction of CD34+ cells in HIV-1 infected individuals with an MoMLV-based retroviral vector. They did not describe results of the trial or that a minimum number of transduced HP cells should be used for long term engraftment. Objectives of the trial included determining the efficiency of transduction and safety and to test whether the ribozyme would confer a survival advantage (or disadvantage) to the progeny cells in vivo.

FIG. 4 shows the structure of Rz2 and its target sequence at position 5833 to 5849 within the HIV-1 strain HXB2 (Genbank sequence K03455), where cleavage occurs after the GUA triplet at position 5842. The target sequences comprise nucleotides 5833-5849 (GGAGCCA GUA GAUCCUA) (SEQ ID NO. 2) of reference strain HIV-HXB2 (Genbank accession number K03455) or nucleotides 5865 to 5882 (GGAGCCA GUA GAUCCUA) (SEQ ID NO. 2) of HIV IIIB (Genbank accession number X01762) or the corresponding region from other HIV strains. DNA nucleotides with the sequence 5'-TTA GGA TCC TGA TGA GTC CGT GAG GAC GAA ACT GGC TC-3' (SEQ ID NO. 3) corresponding to the Rz2 ribozyme were inserted into the SalI site in the 3' untranslated region of the $neo^R$ gene within the plasmid pLNL6, which contains the replication-incompetent retroviral vector LNL6 (Genbank accession number M63653) to generate a new virus, RRz2. The ribozyme sequence was expressed as a $neo^R$-ribozyme fusion transcript from the Moloney Murine Leukemia Virus (MoMLV) Long Terminal Repeat (LTR) in RRz2.

It is preferred that the nucleotide sequence immediately around the ribozyme cleavage site(s) is highly conserved in the viral target RNA. This can readily be determined by comparison of sequences available in sequence databases, or tested experimentally by multiple-passage assays (Wang et al 1998). The Rz2 target/cleavage site in HIV-1 is conserved in almost all naturally occurring infectious isolates. In a Phase I clinical trial, two sequence variants were observed at positions −4 and −1 relative to the GUA triplet at the cleavage site. However, these variants may represent less fit pseudotypes.

Since $CD4^+$ and CD8+ T-lymphocytes, monocytes and macrophages are the most susceptible to HIV infection, genetic modification of these cells so that they express Rz2 leads to inhibition of HIV infection. Preferably, the genetic modification is accomplished during the early stage of hematopoiesis.

Vectors

Different types of vectors can be used for transduction or transformation of HP cells. These include plasmid or viral vectors. Retroviral vectors have been used widely so far in gene therapy (Chu et al 1998), particularly those based on Moloney murine leukemia virus (MoMLV), a member of the murine oncoretroviruses. Other murine retroviral vectors that can be used include those based on murine embryonic stem cell virus (MESV) and murine stem cell virus (MSCV). Vectors based on murine oncoretroviruses can be used for high efficiency transduction of cells, however, they require that the cells be active in cell division. Following entry into the cell cytoplasm and reverse transcription, transport of the preintegration complex to the nucleus requires the breakdown of the nuclear membrane during mitosis. Transduction of HP cells with murine retroviral based vectors therefore requires activation of the cells.

Lentiviral vectors (Amado and Chen 1999), a subclass of the retroviral vectors, can also be used for high-efficiency transduction (Haas et al 2000, Miyoshi et al 1999, Case et al 1999) and are able to transduce non-dividing cells (Uchida et al 1998, Sutton et al 1998). The preintegration complex is able to enter the nucleus without mitosis, and therefore lentiviral transduction does not require the induction of HP cells into cell cycle. This increases the likelihood that the cells remain pluripotent. The use of lentiviral vectors in gene therapy against HIV-1 has been reviewed (Mautino and Morgan 2002).

Other groups of retroviruses such as spumaviruses, for example the foamy viruses (Vassilopoulos et al 2001) are also capable of efficiently transducing non-dividing cells.

Other types of viral vectors that can be used in the invention include adenoviral vectors (Fan et al 2000, Knaan-Shanzer et al 2001, Marini et al 2000), adeno-associated viral (AAV) vectors (Fisher-Adams et al 1996), SV40 based vectors (Strayer et al 2000), or forms of hybrid vectors (for example Feng et al, 1997 or Lieber et al 1999). Adenoviral vectors can be readily produced at high titers, that can be easily concentrated (1012 pfu/ml), and can transduce non-dividing cells. Large DNA inserts can be accommodated (7-8 kb). Immune reactions against adenovirus in vivo can be alleviated by removing genes encoding certain proteins.

AAV vectors are non-pathogenic, transduce both proliferating and non-proliferating cells including $CD34^+$ cells, and integrate stably into the cellular genome (Grimm and Kleinschmidt 1999). Moreover, they do not induce a host immune response and can be produced in helper-free systems to high titers of about 1010 cfu per ml. AAV is a non-enveloped virus with a single-stranded DNA genome. AAV vectors can readily incorporate up to about 4 kilobases of new DNA, although recent studies have extended this. AAV vectors can effectively transduce $CD34^+$ cells in long-term cultures (Chatterjee et al 1999).

Vectors which result in integration of the introduced gene into the cell genome are preferred, to obtain a long lasting effect after return of cells into a patient, for example retroviral vectors including lentiviral vectors, and AAV vectors. Integrating viral vectors are herein defined as those which result in the integration of all or part of their genetic material into the cellular genome. They include retroviral vectors and AAV vectors. They also include hybrid vectors such as adenoviral/retroviral vectors (for example, Feng et al 1997) and adenoviral/AAV vectors (for example Lieber et al 1999). However, vectors that replicate stably as episomes can also be used. It is also desired that the vector can be produced in cell lines to a high titre, in a cost-effective manner, and have minimal risk for patients, for example not giving rise to replication competent virus.

Vector Production

Methods for constructing and producing retroviral vectors are reviewed in Gambotto et al (2000). The vectors are packaged in packaging cell lines such as the PA317 or AM-12 cell lines which contain helper vector(s) that is itself defective in packaging. Several variations in the methods for producing high-titer retroviral supernatants have been described (Schilz et al 2001), including variations in the medium, packaging cells, temperature of harvest and concentration methods by centrifugation or complexation (Le Doux et al 2001). Any of these methods can be used with this invention.

Retroviruses packaged in murine amphotropic envelopes may not transduce primitive HP cells efficiently due to low levels of the amphotropic receptor (Bodine et al 1998). However, cell cycle induction has been shown to lead to increased expression of the amphotropic receptor with a concordant increase in gene transfer (Orlic et al 1999). An alternative approach is to pseudotype retroviral vectors with envelopes such as the envelope from gibbon ape leukemia virus (GALV) (Kiem et al 1997, Eglitis and Schneiderman 1997, Relander et al 2002), vesicular stomatitis virus (VSV-G protein) (Naldini et al 1996, von Laer et al 1998) or feline endogenous virus (Kelly et al 2002). Pseudo-typing vectors may allow concentration, for example by centrifugation.

AAV vectors may be produced in packaging cell lines or cells expressing the AAV rep and cap genes either constitutively or transiently. Production of AAV vectors has been reviewed (Grimm and Kleinschmidt 1999) including the development of helper-free packaging methods and the establishment of vector producer lines. Adenoviral vectors can be produced and purified according to standard methods (eg. see Fan et al 2000).

The biological titre of viral stocks can be readily determined (for example Tavoloni et al 1997).

Expression of the Gene in Vectors

The introduced gene is expressed in the transduced human HP cells of this invention or progeny cells from a promoter. The promoter may be constitutively expressed or inducible, for example being expressed preferentially under favorable conditions or circumstances (for example Chang and Roninson 1996, Saylors et al 1999). Targeted expression to specific cell types may be preferred with some genetic disorders such as hemoglobinopathies or thalassemias (Grande et al 1999). The promoters/enhancers of viral vectors such as the MoMLV retroviral LTR promoter can be modified for improved expression (Robbins et al 1998, Halene et al 1999) or modified by insertion of elements such as insulators (Rivella et al 2000) or scaffold attachment regions (SAR) (Murray 2000). Preferred promoters and additional regulatory elements, such as polyadenylation signals, are those which should yield maximum expression in the cell type (eg T-lymphocytes) which the gene therapy agent is to be expressed in. Thus, for example, HIV-1, HIV-2, HTLV-1 and HTLV-2 all infect lymphoid cells, and in order to efficiently express the gene therapy agent against these viruses, a transcriptional control unit (promoter and polyadenylation signal) are selected which provide efficient expression in hematopoietic, particularly lymphoid cells (or tissues). Preferred promoters are the cytomegalovirus (CMV) immediate early promoter, optionally used in conjunction with the growth hormone polyadenylation signals, and the promoter of the Moloney-MuLV LTR. A desirable feature of an LTR promoter is that it has the same tissue tropism as does the retrovirus of its origin. The CMV promoter is expressed in lymphocytes. Other promoters include VA1 and tRNA promoters which are dependent on RNA polymerase III. The metallothionein promoter has the advantage of inducability. The SV40 early promoter exhibits high level expression in vitro in bone marrow cells. Hematopoietic cell-specific promoters can be used instead of viral promoters (for example Malik et al 1995).

Expression of several anti-HIV genes from MoMLV-based vectors was maintained long term (Austin et al 2000, Su et al 1997) Vectors based on retroviruses other than MOMLV have shown prolonged expression, for example for mouse stem cell virus (MSCV) vectors (Cherry et al 2000) or FrMLV (Cohen-Haguenauer et al 1998). Expression from lentiviral vectors also appears to be maintained in transduced cells (Case et al 1999). Loss of gene expression from retroviral vectors has sometimes been observed after transduction of murine hematopoietic cells (Challita and Kohn 1994, Lange and Blankenstein 1997) but has rarely if ever been observed in transduced human HP cells in humans.

Transduction Methods

In the case of transduction with some murine retroviral vectors, the human HP cells may need to be treated with growth factors to induce cell cycle (see above). This may not be the case with other retroviral vectors. Following any such treatment, the cells need to be contacted with the transducing vector.

In the transduction method of this invention, it is preferable to use the extracellular matrix protein fibronectin (or chymotryptic fragments of fibronectin) which enhances colocalization of cells and viral particles and increases transduction frequencies (Hanenberg et al 1996, Hanenberg et al 1997, Kramer et al 1999, Williams et al 1999), or more preferably the recombinant fibronectin fragment CH-296. Equivalent fragments containing the heparin-binding domain and the alternatively spliced type 3 connecting segment region can also be used (Kiem et al 1998). Use of CH-296 may also aid in the maintenance of the regenerative potential of the HP cells as shown in a mouse xenograft model (Dao et al 1998). Use of CH-296 and growth factor combinations was used in a canine model (Goerner et al 1999) but it was not known how this would apply to humans. Other colocalization agents such as polybrene and protamine sulfate can also be used. These agents act by increasing the apparent titer of viral particles.

Physical colocalization of cells and vector can also be achieved on membrane filters (Hutchings et al 1998) or by centrifugation in fibronectin-coated tubes (Sanyal and Schuening 1999).

Cocultivation of the HP cells on monolayers of the vector-producing murine fibroblasts leads to efficient gene transduction but is not clinically useful as it would expose patients to large numbers of infused murine cells (Halene and Kohn 2000). In contrast, human mesenchymal stem cells can provide stromal support for efficient $CD34^+$ transduction (Reese et al 1999).

Serum-free methods of preparing retroviral vectors for transduction of human HP cells can be used (for example Glimm et al 1998, Schilz et al 1998). The transduction frequency can be increased, particularly for $CD34^+$ CD38low cells, in the presence of fibronectin fragment by reducing the concentration of the vector containing medium or preloading of the vector alone onto the fibronectin fragment (Relander et al 2001). Increased transduction frequency can also be achieved by enriching the virus preparations, for example with cationic and anionic polymers (LeDoux etal 2001).

Transfection of cells by non-viral means can be achieved by the use of cationic liposomes, or DNA-protein complexes such as poly-lysine-DNA complexes, or other means known in the art.

Several authors have reviewed conditions for gene transfer into human hematopoietic cells (Moore and MacKenzie 1999, Sadelain et al 2000).

Transduction Frequency

The frequency of transfer of genes into human HP cells can be determined by standard methods, for example PCR or fluorescent detection (Gerard et al 1996). Transduction frequencies of up to 70-100% have been obtained with retroviral vectors, but this was for relatively small cell samples (Halene et al 1999). Scaling up to clinically relevant levels of material generally results in lower transduction frequencies, particularly for the more primitive HP cells that are needed for long-term reconstitution (eg in the range 1-5% without colocalization agents)

It has been suggested that greater numbers of transduced human HP cells could be obtained by expansion in vitro. However, this can lead to loss of totipotency of the cells and stem cell damage (Bunting et al 1999, Briones et al 1999, Takatoku et al 2001). It is preferred that expansion in vitro be kept to a minimum, although some culture conditions allow some expansion of the HP cells without loss of repopulating potential (Kobari et al 2000, Lewis and Verfaillie 2000, Rosler et al 2000). For example, the combination of cytokines Flt3-Ligand, SCF and thrombopoietin (TPO) can be used (Ng et al 2002). Further addition of IL-3 and IL-6 was not preferred (Herrera et al 2001). Alternatively or additionally, culture of the cells post-transduction with SCF alone for two days can improve engraftment potential (Dunbar et al 2001). Treatment to de-activate the cells post-transduction may improve engraftment potential.

The frequency of transduction of human HP cells isolated from umbilical cord blood with retroviral vectors was increased when the cord blood was first cryopreserved (Orlic et al 1999).

The transduced human HP cells can also be enriched by introducing marker genes such as ones encoding cell-surface reporters (for example see Fehse et al 1997), however this may not be desirable in a clinical setting.

Transduction frequencies can be measured by any of the methods well known in the art, for example by PCR, growth of colonies in the presence of selective agents such as G418 when a selectable marker is included in the construct, or fluorescence-activated sorting. It is preferred that the transduction frequency is measured on a truly representative sample of cells from the total population, for example by quantitative PCR methods (eg real-time PCR) on total DNA from a sample of the cell population. Analysis of transduction frequencies on individual colonies produced from cells in the population is not preferred, but not excluded.

We have found in this invention that a minimum number of transduced human HP cells must be used for prolonged engraftment. Moreover, the transduced HP cells must be capable of undergoing thymopoiesis in order to give rise to differentiated multi-lineage leukocytes.

Types of Genes Introduced

Any gene can be introduced by transduction into human HP cells for this invention. The gene may be used to correct immune deficiencies, including severe combined immunodeficiencies. For example, vectors expressing the adenosine deaminase gene, the RAG1, RAG2 or recombination/DNA repair process genes that are defective in the Alymphocytosis type of SCID, the CD45 gene, or the γc, Jak3, IL-7 Rα genes can all be used (Cavazzana-Calvo 2001). Lysosomal storage diseases such as Gauchers Disease, the most prevalent human lysosomal storage disorder, can be treated. Vectors encoding the glucocerebrosidase (GC) gene such as the MFG-GC retroviral vector (Takiyama et al 1998) can be used for the treatment of Gauchers disease (Dunbar et al 1998a, Dunbar et al 1998b) Chronic Granulomatous Disease (CGD) results from defects in NADPH oxidase, a multisubunit enzyme with four components, and can be corrected with the appropriate gene such as the p47phox gene or the gp91phox gene. Glucose-6-Phosphate dehydrogenase deficiency, which is relatively prevalent in humans, can be treated with the G6PD gene (Rovira et al 2000). Fanconi's Anemia, which results from defects any one of at least eight genes, can be corrected with the appropriate gene, for example by the complementation group C gene (Liu et al 1999). Hemaglobinopathies can be corrected, as can Glanzmann thrombasthenia (Wilcox et al 2000), and Fabry disease (Takenaka et al 2000), each with the appropriate gene. CD34$^+$ cells can be transduced with myeloprotective genes such as MDR-1 as part of treatment for hematopoietic malignancies including leukemias, myelomas and lymphomas as well as non-hematopoietic malignancies where chemotherapeutic regimes would result in myeloablation (for example, Abonour et al 2000, Michallet et al 2000). Non-myeloablative conditioning can be used in such cases (Nagler et al 2000). If there is the potential for deleterious effects of expression of the gene on HP cell function where this is not desired, expression of the gene can be controlled by regulatable promoters, well understood in the art.

It should be considered that the presence of a constitutively expressed foreign gene in transduced HP cells might interfere with the processes of stem cell migration, homing and differentiation. An immune response directed at a protein might also lead to elimination of gene-containing cells. This has been seen after adenovirus-mediated gene delivery but does not normally occur after retroviral-mediated gene delivery or introduction of genes into CD34$^+$ cells. Immunologic reactions to the neo gene product are not generally observed. We have found in this invention that the introduction of a constitutively expressed foreign gene in two different retroviral vectors did not interfere with the processes of stem cell migration, homing and differentiation. Moreover, the use of human HP cells as the target for correction of genetic diseases is expected to be advantageous in that development of immunologic tolerance to the transgene product may be induced in such cells (Halene and Kohn 2000).

Furthermore, RNA products from the transgene such as ribozymes are expected to have negligible immunogenicity. The RevM10 gene encoding an anti-HIV protein did not inhibit the differentiation of transduced human CD34$^+$ cells in SCID mice (Su et al 1997, also Yu et al 1995). Proteins such as INFalpha have been expressed in CD34$^+$ cells without affecting engraftment and differentiation in NOD/SCID mice (Quan et al 1999).

Furthermore, human HP cells can be modified to provide them with a selective advantage in vivo in certain circumstances (for example Kirby et al 2000) or in the presence of selective agents (Omori et al 1999, Ragg et al 2000).

EXAMPLES

Example 1

Reagents

All steps were performed aseptically in a Class II Biological Safety Cabinet.

1.1. DNAse Solution (10 mg/ml).

Stock DNAse solution was used in the preparation of CD34$^+$ cryopreservation medium. 1.4 ml sterile saline solution (Sterile saline inhalation solution USP (0.9% NaCl), Dey Corp. NDC# 49502 830) was added to DNAse (DNAse I Type IIS, Sigma Cat# D-4513) in a 1.5 ml sterile screw-capped eppendorf tube (Sarstedt, Cat# 72692005) and dissolved by gently agitation. Stored at −20° C. 1 ml stock DNAse was used for every 50 ml cryopreservation medium.

1.2 PBMC Cryopreservation Medium (90% FBS+10% DMSO)

PBMC Cryopreservation Medium was used for the cryopreservation of PBMC cells for archival and safety testing purposes. The medium is constituted to provide maximum viable recovery of PBMC cells upon thaw. It contains 90% Fetal Bovine Serum (StemCell Technologies, Cat# HCC-6450) and 10% DMSO (Sigma, Cat# D-2650), filter sterilized and stored in 4 ml aliquots. Once opened, an aliquot was reserved for the exclusive use of one patient.

1.3 CD34$^+$ Cryopreservation Medium.

This was used for the cryopreservation of CD34$^+$ cells for archival and safety testing purposes. The medium is constituted to provide maximum viable recovery of CD34$^+$ cells upon thawing. This procedure was used for the preparation of 50 ml cryopreservation medium:

The following were pipetted into a sterile 50 ml tube, in this order:
  31 ml IMDM (Iscove's Modified Dulbecco's Medium, Gibco BRL, Cat 12440-046).
  10 ml DMSO (Dimethyl Sulphoxide; Sigma, Cat# D-2650)

8 ml Albuminarc25™ (25% Human Serum Albumin (HSA); American Red Cross, Cat# 451-0513)
15 µl Heparin solution (Heparin 10,000U/ml; Elkins-Sinn Inc.)
1 ml DNAse stock solution (10 mg/ml), see 1 above The components were mixed thoroughly by swirling. To filter sterilize, the mixture was filtered through a Corning 150 ml filter system (Corning Cat#25932-200). Aliquots of 4 ml in 5 ml sterile Nunc tubes were stored at −20° C.

One tube (4 ml) per patient was used for archival samples and co-cultivation samples. The cryopreservation medium was thawed and kept at 4° C. until ready for use. (DMSO is toxic to cells at higher temperatures).

1.4 MGDF (100 µg/ml Recombinant Human Pegylated Megakaryocyte Growth and Development Factor)

The recombinant human pegylated Megakaryocyte Growth and Development Factor was used for stem cell culture to promote cell growth and retroviral transduction. It was prepared and aliquotted as a 100 mg/ml working stock solution and added to the stem cell culture medium at a final concentration of 100 ng/ml.

The contents of a MGDF vial (Amgen Inc., 500 mg/ml recombinant human pegylated MGDF in 1 ml 10 mM sodium acetate containing 5% sorbitol, pH 5) and some IMDM culture medium (Iscove's Modified Dulbecco's Medium; Gibco BRL Cat# 12440-046) were warmed to room temperature. Using aseptic technique, 1 ml of MGDF solution was withdrawn from the vial and transferred to a sterile 15 ml tube (polypropylene conical tube; Corning Cat# 25319-15 or Falcon Cat# 352097). The MGDF was diluted to 5 ml final volume with 4 ml of IMDM to create a 100 mg/ml working stock solution. Aliquots (1 ml) of working stock solution were transferred to sterile screw cap microcentrifuge tubes (Sarstedt Cat# 72692005).

Once prepared, the MGDF working stock solution has a limited shelf life of 3 days. Prepared MGDF aliquots were stored at 4°-8° C. for up to three days without freezing. A batch of MGDF was prepared fresh for each patient on the day of CD34+ cell preparation (day 0 of culture). For each patient, working stock aliquots of MGDF were prepared from a separate vial of material that was discarded after use. Sufficient aliquots are prepared for at least five individual cell culture medium preparations.

1.5 Stem Cell Factor (50 µg/ml Recombinant Methionyl Human Stem Cell Factor).

The recombinant methionyl human Stem Cell Factor was used in stem cell culture medium to promote cell growth and retroviral transduction. It was prepared as a 50 mg/ml stock solution and used at a final concentration of 50 ng/ml.

Vial of SCF vial (Amgen Inc., 1875 mg lyophilized recombinant human methionyl SCF) and IMDM culture medium (Iscove's Modified Dulbecco's Medium; Gibco BRL Cat# 12440-046) were warmed to room temperature. Using aseptic technique, 1.25 ml of sterile water was drawn up through a needle into a syringe and injected into the SCF vial. The SCF was reconstituted by swirling without shaking. Using a fresh needle and syringe, 0.2 ml of the SCF solution was withdrawn and added to a 15 ml sterile conical tube containing 5.8 ml of IMDM. This made 6 ml of a 50 mg/ml working stock solution. Using a sterile 5 ml pipette, 1 ml aliquots of SCF working stock solution were transferred to sterile microcentrifuge tubes.

Prepared SCF aliquots were stored at 4°-8° C. for up to three days without freezing. The 50 mg/ml stock was prepared fresh for each patient on the day of CD34+ cell preparation (day 0 of culture). A separate vial of material was used for each patient. Each aliquot was single-use only for daily cell culture medium preparation.

1.6 Nevirapine (5 mg/ml Nevirapine-Virimmune™, 18.7 mM)

Nevirapine (Virimmune™) was used to inhibit the replication of HIV in the CD34 stem cell cultures during the period of cell culture and retroviral transduction. Nevirapine was prepared and aliquotted as a 5 mg/ml (18.7 mM) stock solution and added to the cell culture medium at a final concentration of 500 nM. A single batch of nevirapine working stock was prepared for the entire clinical trial. This stock was aliquoted to provide three vials per patient for each day of culture medium preparation.

Approximately 100 mg of Nevirapine anhydrous powder (Boehringer Ingelheim. Mfr# 43074) was weighed into a 50 ml tube (Bluemax™ 50 ml sterile polypropylene centrifuge tube; Falcon Cat# 2098). Ethanol (200 Proof Dehydrated Alcohol USP, Punctilious; Quantum Chemical Corp) was added to the tube to make a 5 mg/ml solution. 0.5 ml aliquots of 5 mg/ml working stock solution were transferred to 1.5 ml sterile screw-capped microcentrifuge tubes (Sarstedt Cat# 72692005) and stored at −20° C.

The Nevirapine stock solution was thawed at room temperature before use. Each aliquot was single-use for daily cell culture medium preparation.

1.7 Fetal Bovine Serum.

Fetal bovine serum was a constituent of the CD34+ culture medium and was used at a concentration of 20%. The viral supernatants used for transduction contained 10% FBS and therefore were supplemented with 10% FBS before use in transduction of the CD34 cells.

FBS, supplied in 500 ml bottles, was aliquoted into 50 ml volumes to minimize wastage. The serum (Fetal bovine serum, 500 ml; Stem Cell Technologies HCC-6450) was thawed in a 37° C. water bath, mixed by swirling without shaking until visibly homogeneous and aliquoted aseptically into 50 ml volumes in 50 ml centrifuge tubes (Bluemax™ 50 ml sterile polypropylene centrifuge tube; Falcon Cat# 2098). The aliquots were stored frozen. Each aliquot was single use for daily medium preparation.

1.8 Preparation of CD34+ Culture Medium.

Isolated CD34+ cells were grown in this culture medium for at least one day before transduction. The medium was designed to maintain high viability of progenitor cells. This procedure is for the preparation of 500 ml of medium:

The following were pipetted into a filter funnel (0.45 µm filter flask with 500 ml receiver; Nalgene cat# SFCA 162-0045) in this order:
400 ml IMDM (Iscove's Modified Dulbecco's Medium; Gibco BRL, Cat #12440-046).
100 ml FBS (Fetal bovine serum 2×50 ml aliquoted according to 1.2 above)
500 ml SCF (see 1.5 above)
500 ml MGDF (see 1.4 above)
13.3 ml nevirapine (see 1.6 above)

Vacuum was applied until half had passed through, then the contents swirled gently to mix. Filtration was completed and the contents swirled again.

The CD34+ culture medium was prepared fresh when required. It was stored at room temperature in a light protected environment until approximately 30 minutes before use, then warmed to 37° C. in a water bath. Medium in excess of immediate requirements was labeled with the patient CRF ID# and stored at 4° C. It was not used for any other patient and discarded when the patient cell culture/transduction/harvest procedure was completed.

1.9 Protamine Sulphate.

Protamine facilitates binding of the vector in viral conditioned medium to target CD34$^+$ cells.

Protamine Sulfate from ampoules (Elkin-Sinn, 5 ml, 10 mg/ml) was aliquoted to minimise wastage. Each CD34$^+$ transduction used 2 aliquots per patient so approximate 0.5 ml aliquots were dispensed into 10×1.5 ml sterile screw-capped microfuge tubes. These were stored at 4° C. without freezing. One vial was used on each day of transduction (day 1 and day 2) for preparing the VCM transduction mix. Aliquots were single use and discarded after VCM preparation on each day.

1.10 VCM Transduction Mixes with Protamine Sulfate.

Cultured CD34$^+$ cells were transduced with Virus Conditioned Medium (VCM) made by Magenta Corporation (bIOrELIANCE Corp.) under GMP conditions. There were two VCM preparations corresponding to the ribozyme and control vectors. The PA317/RRz2 VCM was of a lower titer than the PA317/LNL6 VCM, therefore 300 ml RRz2 or 200 ml LNL6 was used per transduction to equalise the numbers of infectious viral particles in each transduction.

Transduction proceeded over two consecutive days. To make VCM transduction mixes, each VCM was supplemented with growth factors and serum to match the culture medium of the first day as follows:

On Day 1, one 200 ml bottle of PA317/LNL6 VCM, two 200 ml bottles of PA317/RRz2 VCM and 2×30 ml aliquots of Fetal Bovine Serum were completely thawed at 37° C. in a waterbath. An aliquot of Nevirapine was thawed at room temperature and other reagents warmed to room temperature: 1 aliquot Protamine Sulfate, 1 aliquot SCF, 1 aliquot MGDF.

Preparation of the LNL6 mix was completed before starting the RRz2 mix. To prepare the LNL6 VCM, the following were pipetted into a filter funnel (Nalgene 0.45 mm filter flask with 500 ml receiver, Nalge SFCA 162-0045) in this order:

20 ml FBS (see above)
88 ml protamine sulfate (see below)
220 ml SCF (see above)
220 ml MGDF (see above)
6 ml nevirapine (see above)
200 ml PA317/LNL6 (PA317/LNL6-3; Magenta Corporation, titre 1.4×10$^7$ ivp/ml)

The funnel was swirled gently to mix and vacuum applied to filter the mixture.

The RRz2 VCM was prepared in the same fashion except that the following volumes were used:

30 ml FBS
132 ml protamine sulfate
330 ml SCF
330 ml MGDF
9 ml nevirapine
300 ml PA317/RRz2 (PA317/RRz2-17R'; Magenta Corporation, titre 0.8×10$^7$ ivp/ml)

The remaining 100 ml RRz2 VCM was labeled with the CRF# and immediately re-frozen at −80 C. This was used on the second day of transduction.

The same procedure was followed on Day 2 for preparation of the second LNL6 and RRz2 VCM transduction mixes except that one 200 ml bottle of the PA317/RRz2 and the remaining 100 ml from Day 1 were used for the RRz2 mix.

Each VCM transduction mix was prepared fresh on each day of transduction and stored in the biological safety cabinet until the CD34$^+$ cells were ready for transduction.

1.11 Preparation of Retronectin® (25 mg/ml Retronectin in PBS).

Retronectin® (human fibronectin fragment CH-296) solution was used to coat tissue culture vessels to facilitate retroviral transduction of CD34$^+$ cells.

1 vial containing 2500 mg lyophilized Retronectin® from Takara Shuzo Co. Ltd., code #T100B, ordered from BioWhittaker, was warmed to room temperature. 2.5 ml of sterile water was added, the material dissolved by gentle swirling, and removed with a syringe with needle. The mixture was filtered through a Millex filter (Millipore, cat # SLGV 0130S) into a 50 ml tube (50 ml sterile tissue culture tube; Falcon Cat # 2098) and diluted with 4 ml of PBS split into two 50 ml tubes and made up to 100 ml total volume. 200 ml was removed for endotoxin testing at the same time as the final product, the rest was stored at 4° C. Generally, the reagent was coated onto vessels immediately.

1.12 Preparation of 2% HSA (Human Serum Albumin in PBS).

2% HSA was used to block the tissue culture vessels after they were coated with Retronectin. It was prepared by aseptically mixing 8 ml of 25% HSA solution (Albumarc25') with 92 ml PBS (calcium & magnesium free, 1x; Virus Core Lab or JRH Biosciences Cat #59321-78P). The reagent was generally used immediately.

1.13 Retronectin-Coated Vessels.

Flasks coated with Retronectin were used for some patients to transduce CD34$^+$ cells with retroviral vectors.

25 ml of the Retronectin solution (see above) was pipetted into 4×175 ml flasks (Bacterial plastic flasks 175 cm$^2$, with 0.2 µm vented closures, Sarstedt 83.1812.502) and let stand for 2 hours at room temperature. The solution was removed from the flasks and 25 ml of the 2% HSA added. After a further 30 min at room temperature, the solution was removed and the flasks washed with 25 ml of IMDM (Iscove's Modified Dulbecco's Medium; GIBCO BRL, Cat #12440-046). The flasks were sealed in plastic bags and stored at 4° C. before use within 2-3 days.

1.14 VCM Transduction Mixes (used with Retronectin).

When retronectin-coated flasks were used for the transductions, protamine sulphate was omitted from the VCM Transduction Mixes. These were prepared in a similar fashion to those described in 1.10. above except that the following volumes were used:

For the first transduction in the morning of day 2, 200 ml aliquots of the virus preparations were thawed in a 37° C. waterbath, as was an aliquot of the FBS. The LNL6 or RRz2 VCM Transduction Mixes (with Retronectin) were prepared by adding into a filter funnel (Nalgene 0.45 µm filter flask with 250 ml receiver, Nalge SFCA 162-0045) in this order:

10 ml FBS (see above)
110 ml SCF (see above)
110 ml MGDF (see above)
3 ml nevirapine (see above)
100 ml PA317/LNL6 or 100 ml PA317/RRz2 (see above)

The components were mixed by gentle swirling and sterilized by filtration. Preparation of the LNL6 mix was completed before starting the RRz2 mix.

For a second transduction in the evening, the remaining 100 ml of PA317/LNL6 and 100 ml of PA317/RRz2 were used in the same way to prepare VCM Transduction Mixes. These were stored at room temperature until used.

1.15 VCM transduction mixes used with Retronectin (patients 8-10). VCM transduction mixes for patients #8-10 were prepared and used in the same way except that the volumes used in the preparation were doubled. Three rounds of transduction were preformed over 2 days, namely on the evening of day 1, and morning and afternoon of day 2.

1.16 CD34$^+$ cell Wash Buffer (PBS with Ca$^{2+}$ & Mg$^{2+}$, +1% HSA).

CD34$^+$ wash buffer containing 1% (final concentration) HSA was used for washing of the cells prior to infusion of the transduced CD34+ cells. 1 L wash buffer was used per patient and was prepared fresh or several days in advance.

From a new 1 L bottle of PBS, 40 ml of PBS was removed with a sterile 25 ml pipette so that approx 960 ml remained. 40 ml of 25% HSA solution (25% HSA Solution, Albumarc25™) was aseptically transferred to the PBS bottle using a 50 ml syringe with 18 gauge needle attached, and mixed well by swirling, without shaking. The Wash Buffer was stored at 4° C. and warmed to 37° C. before use. A 1 L batch was for the exclusive use of one patient and was single-use only, any remainder was discarded.

1.17 CD34+ Infusion Buffer (RPMI, Phenol Red Free, +5% Human Serum Albumin).

CD34+ Infusion buffer is designed to maintain viability of the transduced CD34+ cell harvest until transfused. The RPMI was free of phenol red as it was used for direct infusion into the patient. It contained human serum albumin at 5% final concentration.

100 ml was used for suspension of each batch of harvested cells after washing. This buffer can be made fresh on the day of harvest/infusion or can be prepared several days in advance.

Using a 25 ml sterile pipette, 80 ml phenol red-free RPMI (Phenol Red free, Gibco-BRL, Cat 118-030) was transferred to a 250 ml conical centrifuge tube. 20 ml 25% HSA solution (Albumarc25™), American Red Cross, was added aseptically using a 25 cc syringe with 21 gauge needle attached. The mixture was swirled gently. If the reagent was prepared in advance, it was stored at 4° C., but if prepared fresh on the day of harvest, it was stored at room temperature until use. The mixture was prewarmed to 37° C. before use. A 100 ml batch was for the exclusive use of one patient and was single-use only.

1.18 Preparation of FACS PBS (PBS, $Ca^{2+}$ & $Mg^{2+}$ free, +2% Fetal Bovine Serum+0.1% $NaN_3$)

FACS PBS is a wash buffer that was used to wash the cells during the FACS staining procedure. Additionally, if FACS analysis was performed immediately after staining (ie within the next 4-6 hours) it was used to resuspend the stained cells.

An Azide stock solution (10%) was prepared by dissolving 4 g of sodium azide in a 50-ml tube in distilled water. The FACS PBS solution was prepared by adding to 48.5 ml of PBS, in a 50 ml tube, 1 ml fetal bovine serum and 0.5 ml of the sodium azide solution. The solutions were stored at 4° C. The azide stock solution has an unlimited shelf life, the FACS PBS has a shelf life of 1 year. The FACS PBS was used chilled.

1.19 Preparation of FACS Blocker (5% Human AB Serum in PBS, $Ca^{2+}$ and $Mg^{2+}$ Free).

This was used in the FACS antibody staining reaction to reduce non-specific background staining of the cells. It contained 5% human AB serum (Sigma cat #H-4522, stored at −20° C., thawed in a 37° C. waterbath) diluted in sterile PBS (calcium & magnesium free, 1x; Virus Core Lab or JRH Biosciences cat #59321-78P) It was filter sterilized through an Acrodisc 0.45 μm filter (Gelman #4184) and stored as 1 ml aliquots at −20° C.

1.20 Preparation of FACS Paraformaldehyde Fixative (PBS, Ca & Mg Free, 2% Paraformaldehyde).

The FACS Paraformaldehyde is a fixative solution that preserves cells after antibody staining for FACS anaysis. Used at 1% concentration to resuspend cells after FACS staining, the antibody staining will remain stable for up to at least 3 days. After this time, the background signal from the fluorescent antibodies may increase. It contained 10 ml of 10% paraformaldehyde (Polysciences #04018) mixed with 40 ml of PBS and was stored at 4° C. Cells were suspended in 200 μl of PBS and then fixed with 200 μl of this buffer to create a working concentration of 1%.

1.21 Urea Lysis Buffer

Urea lysis buffer was used to prepare cell lysates for phenol extraction of DNA. It contains 84 g urea (Boehringer-Mannheim 1685 899), 4 g SDS (USB 21651), 1 ml 0.2M EDTA, 1 ml 1M Tris base, 1 ml 1M Tris HCl, 14 ml 5M NaCl in a final volume of 200 ml in water. This solution was filtered through a 0.45μ filter and stored at room temperature.

Example 2

Phase I Clinical Trial

We performed a phase I gene therapy clinical study to investigate whether i) the introduction of an anti-HIV-1 ribozyme into circulating hematopoietic progenitor cells could result in the emergence of thymic emigrants bearing vector sequences, ii) normal T-lymphocyte maturation could take place in genetically modified cells, iii) vector presence and expression could persist long-term and iv) the ribozyme could confer a survival advantage to HIV-1 vulnerable cells (Amado et al. 1999).

For transduction of cells with a ribozyme gene, RRz2 was used. RRz2 encodes the hammerhead ribozyme Rz2, which is directed against a highly conserved region of the tat gene of HIV-1. The DNA sequence encoding Rz2 was sub-cloned into a Sal-I site within the untranslated region of the neomycin phosphotransferase ($neo^R$) gene in pLNL6 (Bender et al 1987) to make RRz2. The ribozyme is expressed as a neo-ribozyme transcript from the MoMLV LTR in RRz2. To control for the potential ribozyme-specific effects on progenitor cell engraftment and T-lymphoid development, and to study potential effects on T-lymphocyte survival conferred by Rz2, progenitor cells were also transduced with the control retroviral vector LNL6.

In this study, HIV-1 infected patients with viremia less than 10,000 copies/ml and CD4 counts between 300 and 700 cells/$mm^3$ underwent mobilization of peripheral blood progenitor cells (PBPC) with the cytokine granulocyte colony stimulating factor (G-CSF) for 6 days. Patients received granulocyte colony stimulating factor (G-CSF) subcutaneously at a dose of 10 μg/kg daily for 6 days. PBPC procurement was carried out by performing one blood volume of apheresis on days 5 and 6 of G-CSF treatment using the COBE® Spectra Apheresis System (Gambro BCT, Lakewood, Colo.). CD34+ cell selection was performed using the CEPRATE® SC Stem Cell Concentration System (CellPro Inc. Bothell, Wash.) (patients 1 to 7) and Isolex 300i cell selection system (Nexell Therapeutics, Irvine, Calif.) (patients 8 to 10). After purification of PBPC for CD34 surface marker expression, cells were cultured for only one day in CD34 Culture Medium for induction into cycle using the cytokine combination of megakaryocyte growth and development factor (MGDF) and stem cell factor (SCF) (Amado et al 1998). MGDF and SCF were supplied by Amgen Inc. (Thousand Oaks, Calif.) and used at a concentration of 100 ng/ml and 50 ng/ml respectively.

Approximately, equal numbers of CD34+ cells were transduced independently with the RRz2 and LNL6 vectors. The LNL6 and RRz2 producer cell lines were prepared in a two stage process by transfecting the cDNA constructs, pLNL6 or pRRz2, into the psi2 packaging cell line to produce two populations of ecotropic replication-incompetent virus. These two populations were then used to infect the PA317 amphotropic packaging cell line (Miller and Buttimore 1986). Clonal producer cell lines derived following selection in G418, were checked for integrity of the constructs and sent to BioReliance Corporation (Rockville, Md.) for manufacture of a Master Cell Bank and subsequent manufacture of GMP virus with safety testing. All batches of retroviral supernatant (LNL6 and RRz2) were tested for sterility, replication-competent retrovirus and general safety by BioReliance Corporation. Viral titers were confirmed by infecting the NIH 3T3 cell line using serial dilutions and scoring G418 resistance. LNL6 and RRz2 titers were $1.4 \times 10^7$ and $0.8 \times 10^7$ infectious viral particles/ml respectively. Retroviral supernatant (VCM Transduction Mix) was added once daily for two days for patients 1 to 3, twice in one day for patients 4-7, and 3 times over 2 days for patients 8 to 10. For patients 4 to 10, transductions were performed in flasks coated with the CH296 fragment of human fibronectin (RetroNectin™, Takara Shuzo, obtained from BioWhittaker, Inc. Walkersville, Md.). To inhibit potential HIV replication in vitro, CD34+ cell cultures and transductions were carried out in the presence of Nevirapine at a concentration of 500 nM (Boehringer Ingelheim, Ridgefield, Conn.). Absence of HIV replication was verified by measuring p24 antigen by ELISA in the final infusate (all 10 samples had undetectable p24 levels). Fungal, bacterial and mycoplasma cultures, as well as endotoxin assays were negative in the final cell product for all 10 patients.

Figure 5:
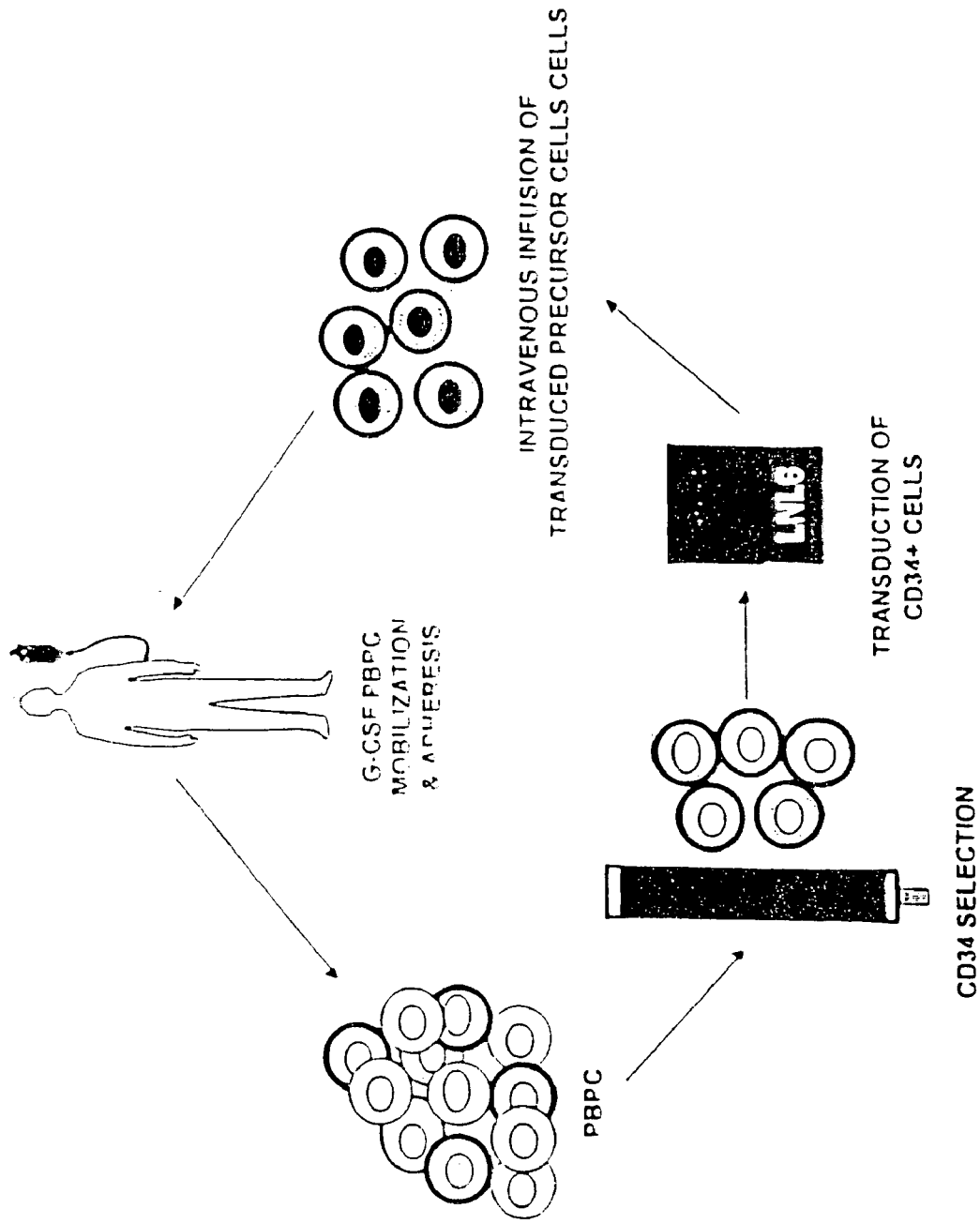
FIG. 5. Schematic Representation of CD34+ Phase I Clinical Trial. Ten subjects with HIV-1 infection were enrolled. The LNL6 and RRz2 vector were separately introduced into autologous CD34+ hematopoietic cells. Both populations of cells were infused into the patients without myeloablative treatment.

Following transduction, cells were pooled, tested for sterility, cell count, viability, CD34/CD38 phenotype, p24, and endotoxin, and then washed and infused into autologous recipient patients without myelosuppression. This treatment schema is illustrated in FIG. 5. Samples were kept aside for later testing in CFC assays, RCR analysis and PCR analysis for transduction efficiency.

Ten patients were enrolled on this study (Table 1). The median age was 42 years (range 32 to 59). The median number of antiretroviral regimens used was 3 (range 1 to 6). The total number of CD34+ cells infused ranged from 1.3 to $10.1 \times 10^6$ cells per kilogram of body weight (kg) (median $3.2 +/- 1.1 \times 10^6$ cells/kg). Transduction efficiency for the first 3 patients, carried out in the presence of protamine sulphate, was low (range <1% to 4%), accounting for a number of transduced CD34+ cells infused ranging from 0.01 to $0.08 \times 10^6$ cells/kg (Table 1). Cells carrying the transgene were detected up to 6 months in patient 1 (ribozyme in bone marrow and peripheral blood mononuclear cells (PBMC), LNL6 in granulocytes), up to 9 months in patient 2 (RRz2 in PBMC) and 12 months in patient 3 (LNL6 in PBMC and RRz2 in monocytes).

Table 1. Characteristics of the patients and of the CD34+ cell infusion product. The Table shows patient's age, gender, number of prior antiretroviral regimens (ART), use of retronectin to support transduction, CD34+ purity, number of infused CD34+ cells, percentage of transduction, and number of transduced CD34+ cells infused.

TABLE 1

| Patient | Age | Gender | ART | Retronectin | CD34+ Purity (%) | Infused CD34+ cells ($\times 10^6$/kg) | Transduction (%) | Transduced CD34+ cells ($\times 10^6$/kg) |
|---|---|---|---|---|---|---|---|---|
| 01 | 59 | M | 1 | No | 65 | 3.38 | 0.4 | 0.01 |
| 02 | 44 | M | 4 | No | 80 | 2.08 | 4 | 0.08 |
| 03 | 40 | M | 4 | No | 66 | 2.98 | 2 | 0.06 |
| 04 | 44 | M | 6 | Yes | 67 | 1.29 | 10 | 0.13 |
| 05 | 37 | M | 6 | Yes | 94 | 10.01 | 7 | 0.70 |
| 06 | 32 | M | 3 | Yes | 90 | 1.63 | 32 | 0.52 |
| 07 | 41 | M | 3 | Yes | 96 | 8.45 | 48 | 4.06 |
| 08 | 46 | M | 2 | Yes | 98 | 9.37 | 57 | 5.34 |
| 09 | 48 | M | 3 | Yes | 93 | 1.64 | 36 | 0.59 |
| 10 | 38 | F | 1 | Yes | 95 | 5.07 | 28 | 1.42 |

Figure 6:
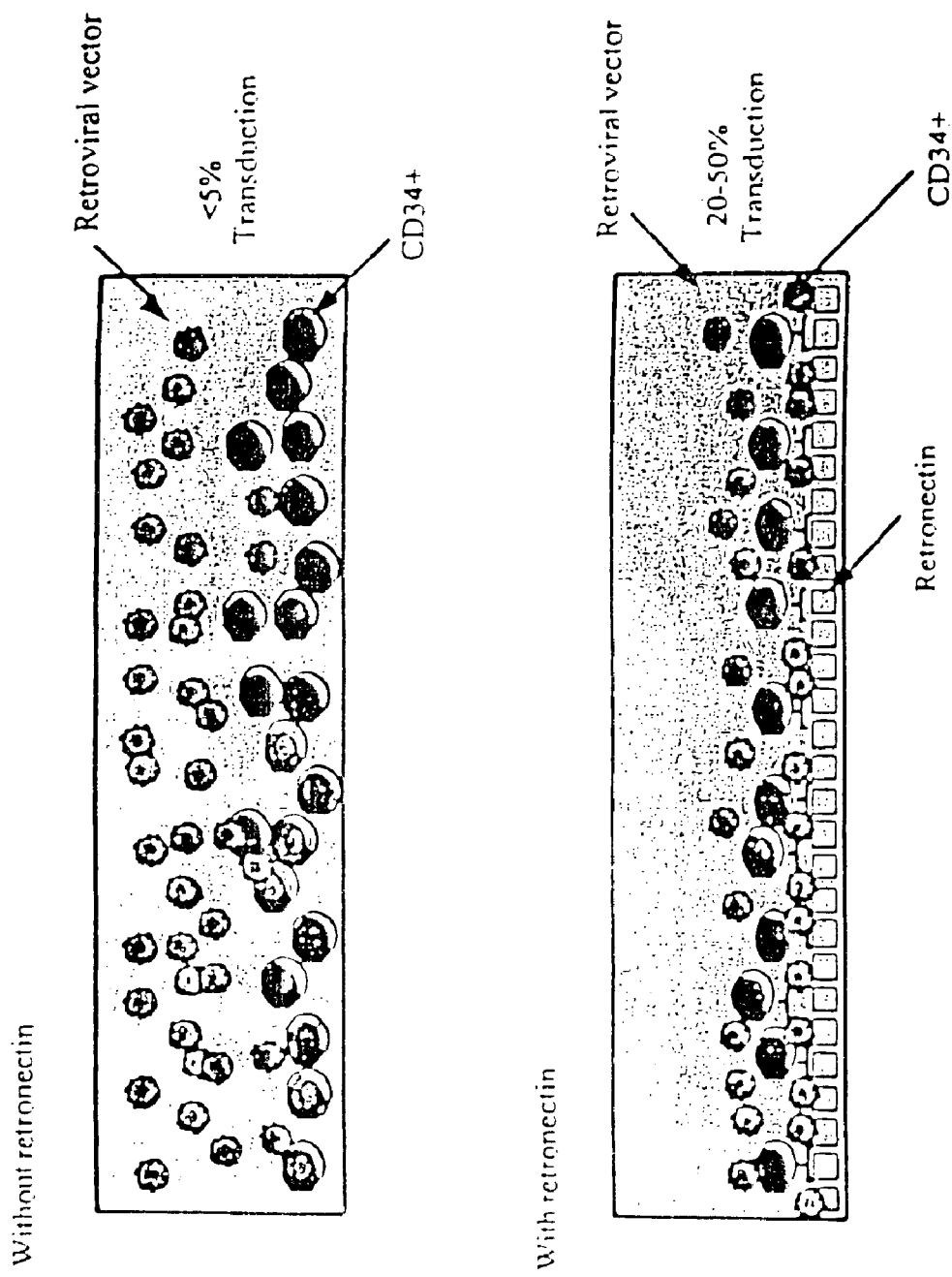
FIG. 6. Effect of retronectin on transduction. This shows schematically how retronectin facilitates retroviral transduction by bringing the CD34+ cells into close proximity to the retroviral vector.

To improve transduction efficiency, 7 subsequent patients received autologous CD34+ cells transduced in the presence of the CH296 fragment of human fibronectin (Hanenberg et 1997; Hanenberg et al 1996). In these patients, transduction efficiency increased to a median level of 32%+/−6.9 (range 7% to 57%) (FIG. 6). Calculation of transduction efficiencies was carried out by performing competitive PCR in transduced CD34+ cells (Knop et al 1999). Efficiencies were also determined by performing PCR for vector sequences in single colonies grown from the final transduced CD34+ cell product.

On average, transduction efficiency for LNL6 was 1.6 times higher than that obtained with RRz2, probably reflecting differences in vector titers. After a median follow up of 30 months (range 12 to 36 months), transgenes were detected in all patients at multiple time points and in multiple hematopoietic lineages. On average, gene presence was found in 0.1 to 0.01% of PBMC analyzed.

FIG. 7 shows long-term multilineage gene presence in a representative patient. FIG. 7a shows LNL6 and RRz2 vector sequences in peripheral blood mononuclear cells (PBMC), bone marrow mononuclear cells (BMMC), T-lymphocytes and monocytes in patient 5 two years after infusion of transduced CD34+ cells. T-lymphocytes and monocytes were selected from PBMC to a purity >90%, as confirmed by flow cytometry. For each cell type, 4 replicates of a pool of samples are shown.

Figure 7A:
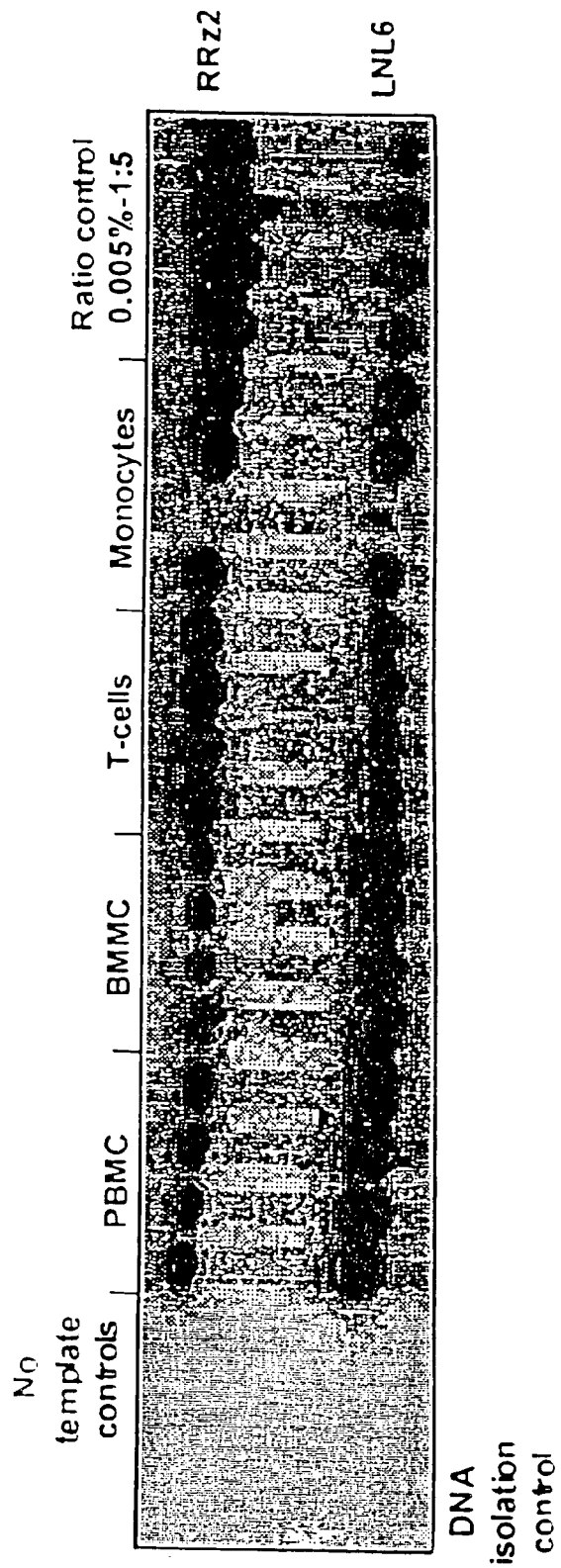
FIG. 7. Long-term vector presence and expression. Semi-quantitative PCR analysis was performed in leukocyte subsets using primers directed against the neo$^R$ gene that overlap the Rz2 sequence in the RRz2 vector. PCR products for LNL6 and RRz2 are 174 and 216 base pairs respectively, and include a tract of the untranslated terminus of the neo$^R$ gene. Graph A shows LNL6 and RRz2 vector sequences in peripheral blood mononuclear cells (PBMC), bone marrow mononuclear cells (BMMC), T-lymphocytes and monocytes in patient 5 two years after infusion of transduced CD34+ cells. Graph B shows short- and long-term expression of both LNL6 and RRz2 in PBMC in 3 representative patients, as measured by RT-PCR. Expression was assessed in a reverse-transcriptase (RT+) nested polymerase chain reaction using radiolabelled primer. For each sample, a reaction that did not contain reverse-transcriptase (−RT) was included. Graph C. Detection of vector sequences in naïve T-lymphocytes. Gel shows PCR analysis for LNL6 and RRz2 vector sequences in CD4+ and CD8+ T-lymphocytes, and in naïve T-lymphocytes subsets selected from peripheral blood in patient 7 two years after infusion of transduced CD34+ cells. D, E and F show detection of vector sequences in naïve T-lymphocytes. Gel shows PCR results for LNL6 and RRz2 vector sequences in CD4+ and CD8+ T-lymphocytes, and in naïve T-lymphocytes subsets selected from peripheral blood in 3 patients. Vector sequences were detected in naïve T-cell subsets as early as 4 weeks post-infusion (panel F), and long-term detection is shown in panels E and D, at 2.5 and 2 years after infusion of transduced CD34+ cells respectively.
Figure 7B:
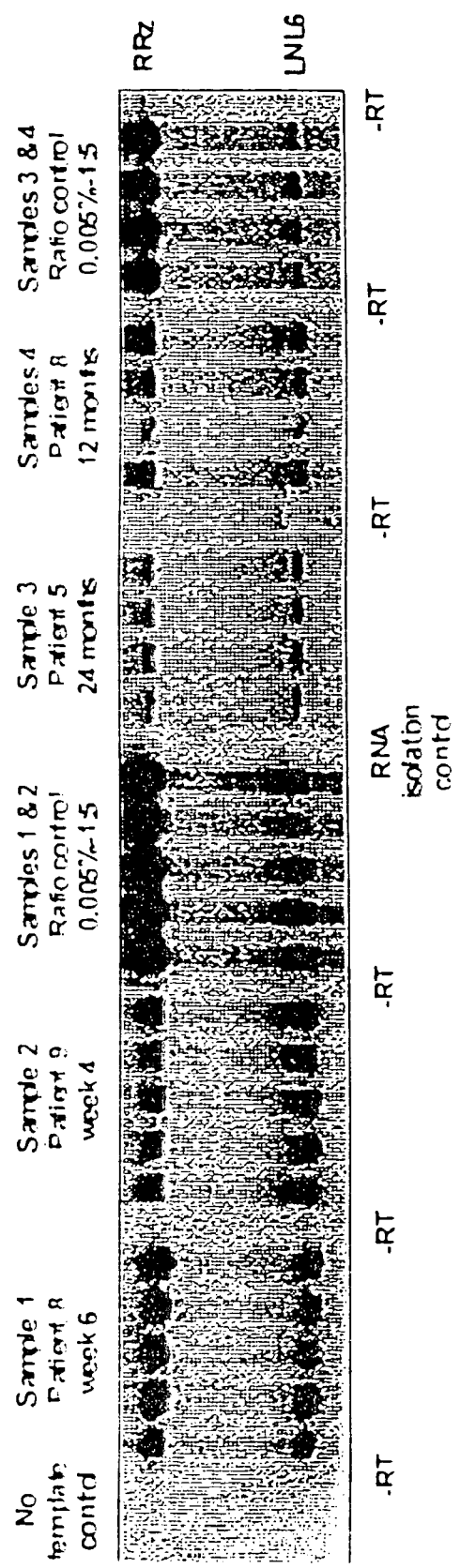

We also analyzed expression of the gene constructs in PBMC using RT-PCR. RNA was prepared from PBMC selected by Ficoll-Hypaque centrifugation of blood samples, using the Qiagen RNeasy kit (Valencia, Calif.), following the manufacturer's instructions. Residual DNA was removed by DNase digestion. RNA was reverse-transcribed using Gibco Superscript Reverse Transcriptase (Carlsbad, Calif.) with 7 replicates of each sample. Samples were then pooled, and cDNA amplification was performed on 10 replicates. Round 1 hot start PCR was performed using Promega Taq bead (Madison, Wis.). Round 2 was performed using Perkin Elmer Ampliwax gem (Boston, Mass.). FIG. 7b shows short- and long-term vector expression of both LNL6 and RRz2 in PBMC up to 2 years post-infusion in 3 representative patients using a radiolabelled primer. For each sample, a reaction that did not contain reverse-transcriptase (−RT) was included.

To determine whether transduced CD34+ cells could undergo T-lymphocyte development in HIV-infected patients we selected peripheral blood CD4+ and CD8+ cells for CD45RA and CD62L surface marker expression, which characterize naïve T-lymphocytes (Sanders et al 1988; Tedder et 1985; Kansas 1996; Picker et al 1993), and we analyzed these T-lymphocyte subpopulations for the presence of LNL6 and RRz2.

Semi-quantitative PCR analysis was performed in leukocyte subsets using primers directed against the neo$^R$ gene that overlap the Rz2 sequence in the RRz2 vector. For PCR detection, DNA was extracted from cell populations using the Acest Polymer extraction method (Ward et al 1998). A DNA ratio control was constructed by diluting DNA from CEM T4 cells transduced with LNL6 & RRz2 at a ratio of 1:5 (where LNL6=1) in a background of PBL (negative) DNA to a concentration of 0.005% marked cells. Nested (hot start) PCR was then performed in a 50 µl PCR reaction mixture. Primers used were 5L1A: CAC TCA TGA GAT GCC TGC AAG (SEQ ID NO. 4); 3L2A: GAG TTC TAC CGG CAG TGC AAA (SEQ ID NO. 5); 5Nes1: GAT CCC CTC GCG AGT TGG TTC A (SEQ ID NO. 6) (Primers Round #1: 5Nes1 & 3L2A, Round #2: 3L2A and labeled: 5L1A). Ten replicates per sample were included in a Round 1 PCR of 17 cycles annealing at 68 C and denaturation at 94 C. The replicate samples were then pooled and used as template for the Round 2 PCR of 35 cycles with annealing temperature at 68 C and denaturation temperature at 94 C. Quadruple product samples were resolved on a 5% denaturing PAGE gel, and quantitated using Molecular Dynamics Imagequant software. PCR products for LNL6 and RRz2 were 174 and 216 base pairs respectively, and include a stretch of the untranslated terminus of the neo$^R$ gene. Results were included if the ratio control was within the acceptable limits (for a ratio of 1:3.5 LNL6:RRz2 in a 0.005% vector containing sample, accepted range was 1:1.1 to 1: 6.9).

Figure 7C:
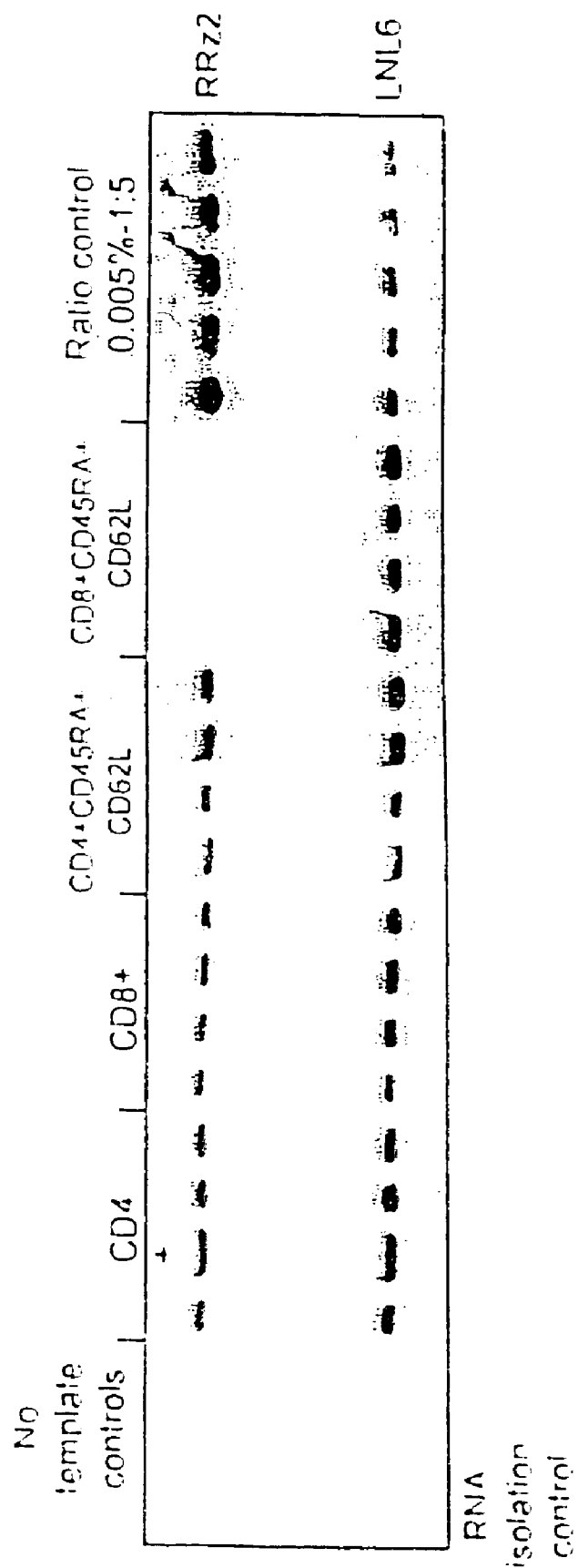

FIG. 7c shows detection of vector sequences in naïve T-lymphocytes. The gel shows PCR analysis for LNL6 and RRz2 vector sequences in CD4+ and CD8+ T-lymphocytes, and in naïve T-lymphocytes subsets selected from peripheral blood in patient 7 two years after infusion of transduced CD34+ cells. Naïve T-lymphocyte populations were selected to purity >90% from CD4 and CD8 selected populations. T-lymphocytes and monocytes were selected from PBMC using CD3 and CD14 MACS MicroBeads (Miltenyi Biotec Inc., Auburn, Calif.). Naïve T-lymphocytes were selected by staining with a FITC-conjugated monoclonal IgG$_1$ anti-CD45RA antibody (Becton Dickinson, Franklin Lakes, N.J.) followed by selection using an anti-FITC Multisort kit (Miltenyi Biotec Inc., Auburn, Calif.). Subsequently, CD62L selection was performed using a murine IgG$_2$a anti-CD62L antibody (Becton Dickinson, Franklin Lakes, N.J.), followed by selection with rat anti-mouse IgG$_{a+b}$ Microbeads (Miltenyi Biotec Inc., Auburn, Calif.).

Figure 7D:
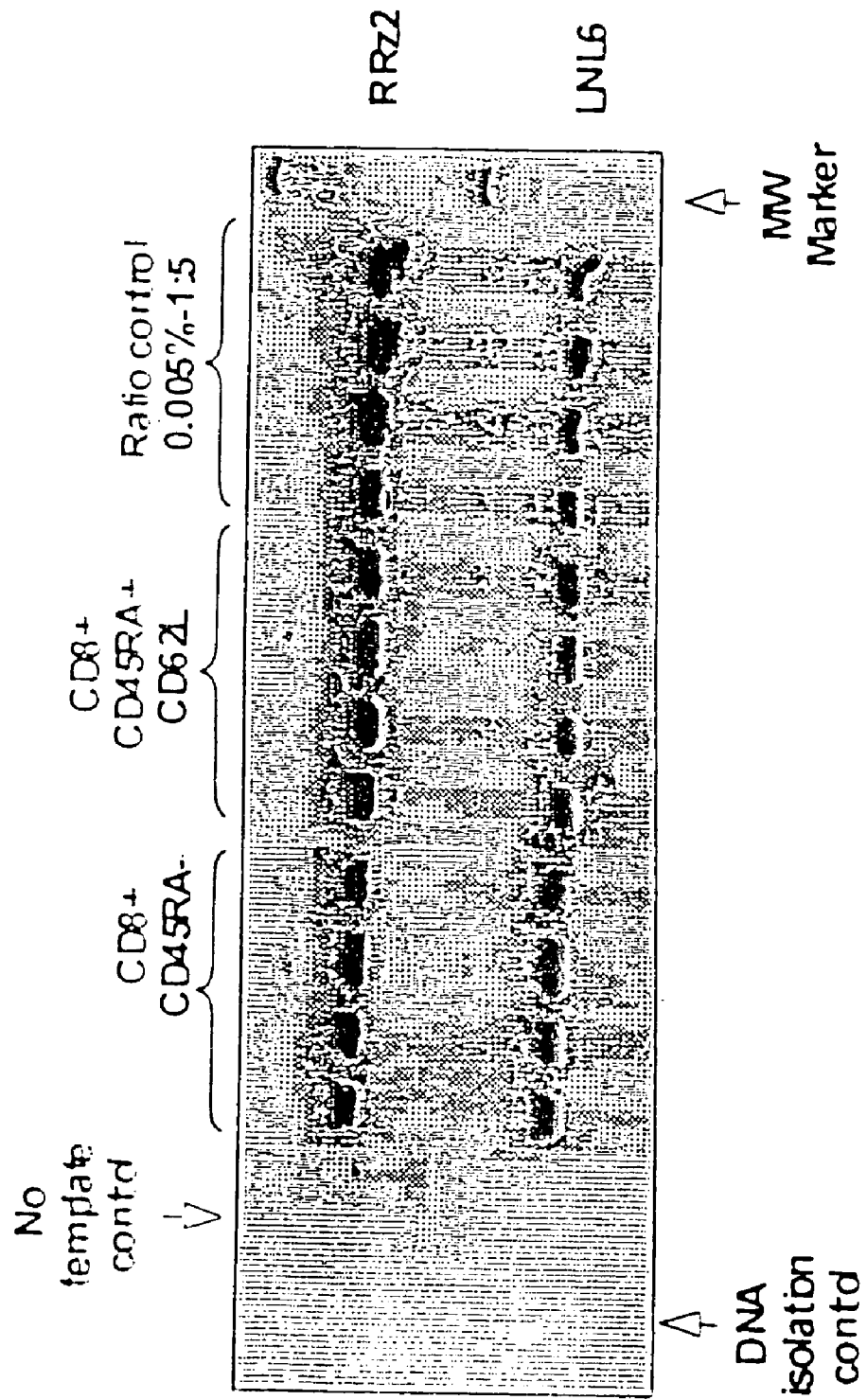

FIG. 7(D) shows vector sequences detected in naïve T-cell subsets in patient 5 at 2.5 years.

Figure 7E:
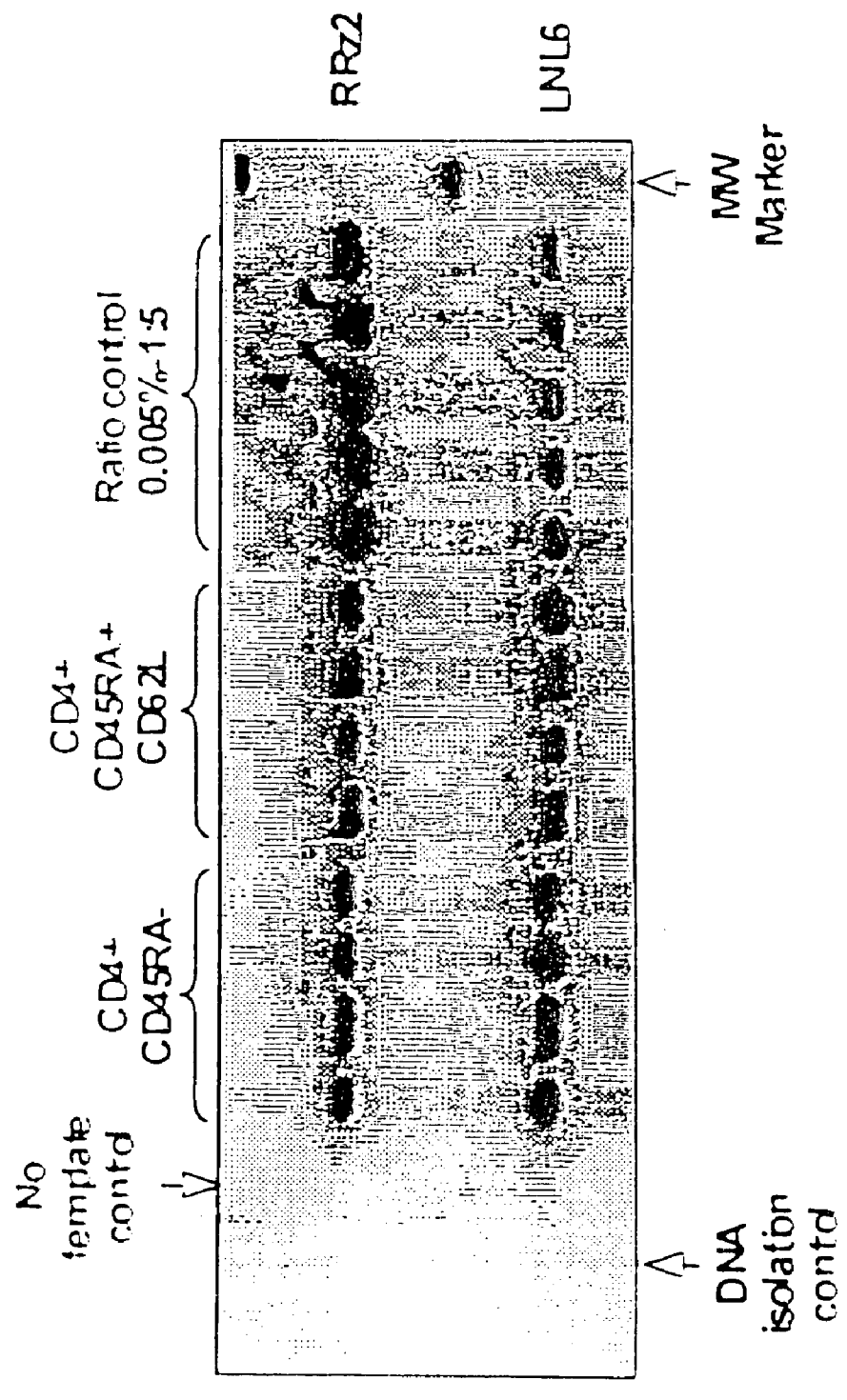

FIG. 7(E) shows vector sequences detected in naïve T-cell subsets in patient 7 at 2 years.

Figure 7F:
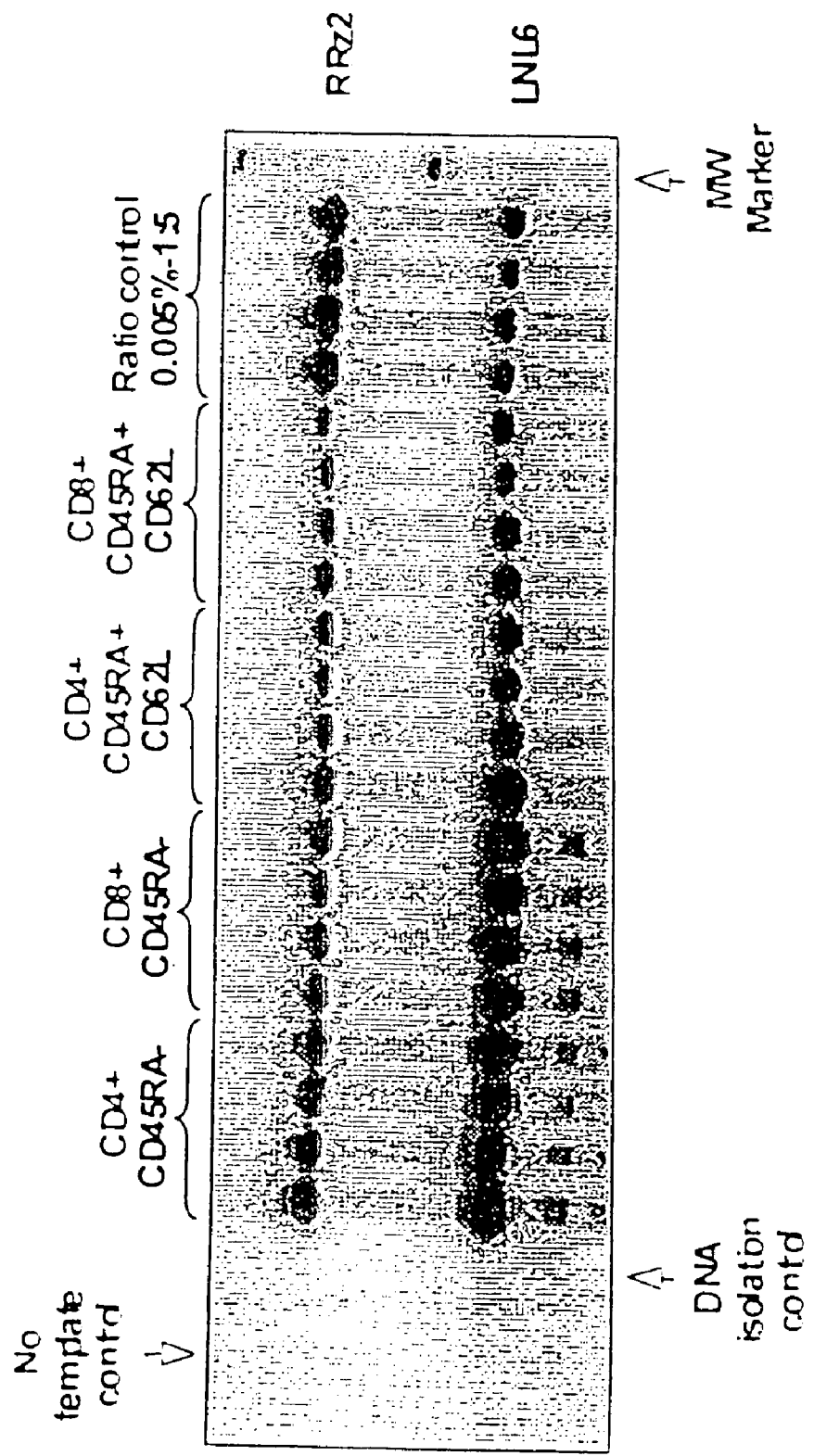

FIG. 7(F) shows vector sequences detected in naïve T-cell subsets in patient 8 at 4 weeks post-infusion.

Figure 8:
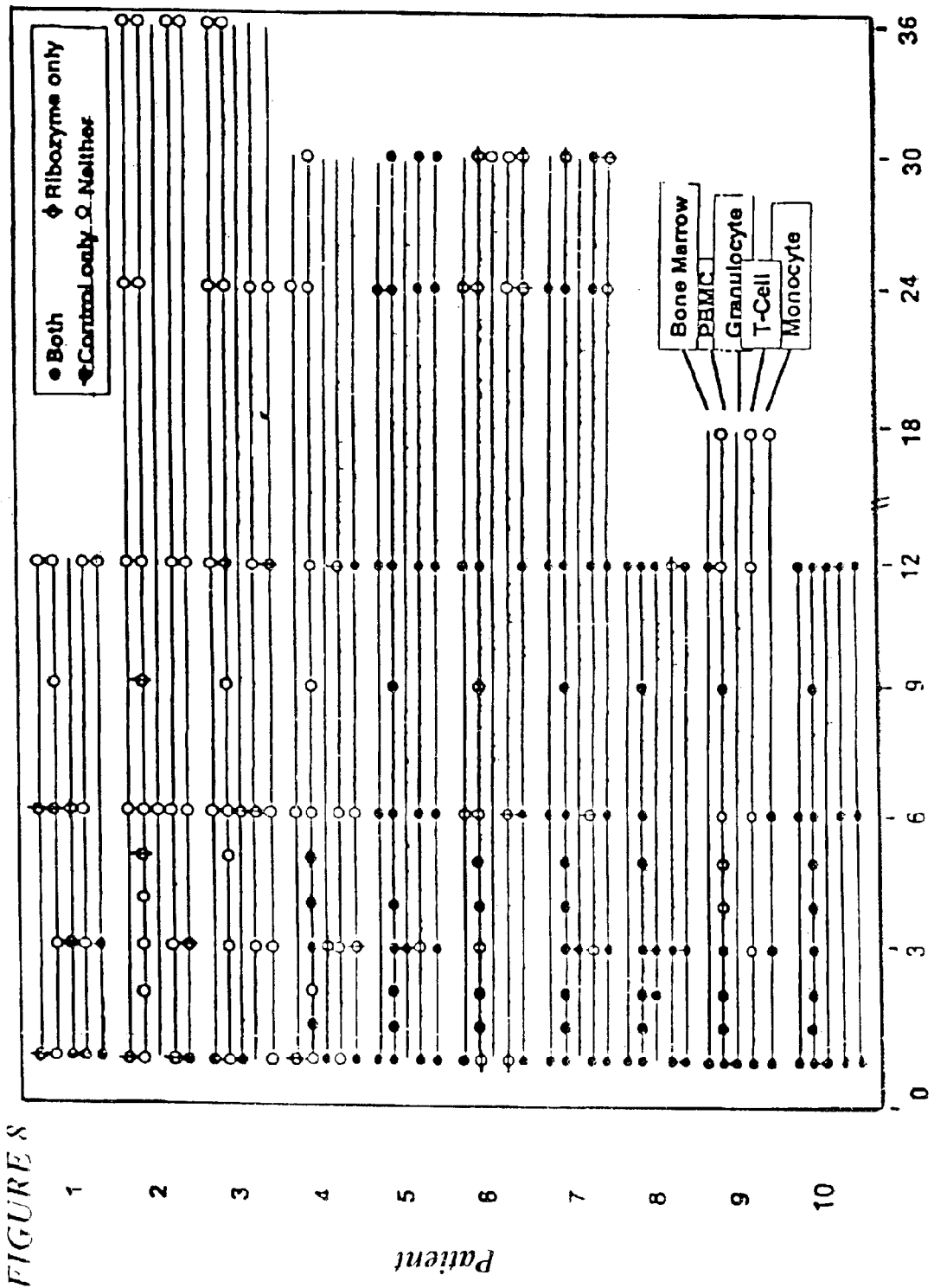
FIG. 8. Summary of vector detection by PCR in 10 patients. Cells were examined by PCR for LNL6 or RRz2 vector detection up to 36 months post-infusion. Cell types were bone marrow mononuclear cells, peripheral blood mononuclear cells (PBMC), granulocytes, T-lymphocytes and monocytes as indicated. Data are shown for each patient as labeled in the Y-axis. Longer-term gene marking was observed after the use of the fibronectin fragment (CH-296), which resulted in an increase in transduction efficiency (see table 1). The presence or absence of vector detection is indicated by circles, without regards to vector copy number: black, both vectors detected; open, neither vector detected; circle with vertical stripe, ribozyme vector only detected; circle with horizontal stripe, LNL6 control vector only detected.

FIG. 8 shows a summary of detection of both ribozyme and control vector transgene by semi-quantitative PCR in bone marrow mononuclear cells (BMMC), PBMC, granulocytes, T-lymphocytes and monocytes in all 10 patients up to 3 years post-infusion.

In all 10 patients, biological assays for replication competent retrovirus (RCR) at the end of transduction using both viral supernatant and cultured CD34+ enriched cells were negative. RCR testing of the final cell infusate was performed on 5% of the culture supernatant at the end of transduction as well as on 1% of the transduced CD34+ cells by co-cultivation, using a 2 passage amplification step in the Mus dunni cell line. The resulting Mus dunni cell culture supernatants were then tested for infectious retrovirus using the PG4 S+L-focus assay. Patient PBMC samples analyzed by PCR for RCR 6 months and 1 year following CD34+ cell infusion revealed no evidence of RCR. For RCR detection in patient cells, DNA extracted from PBMC 6 months and 1 year after transduced-CD34+ cell infusion was analyzed for the presence of amphotropic envelope sequences using the following primers: 5'-CTA TGT GAT CTG GTC GGA GA-3' (SEQ ID NO. 7) and 5'-CCA CAG GCA ACT TTA GAG CA-3' (SEQ ID NO. 8). The assay allows the detection of replication competent retrovirus by amplifying a highly conserved region that encodes part of the host-determining region of the envelope gene, which is required for infection of cells through the amphotropic receptor. The amplified region is 289 base pair-long. The sensitivity of the assay is 1 positive cell in a background of 10$^5$ negative cells. As a positive control, the PA317-packaging cell line was run in each assay. PCR products were resolved on a 2.5% NuSieve gel.)

For both vectors, we found a strong linear correlation between the number of transduced CD34+ cells infused and the persistence of gene detection at 2 years post-infusion in both PBMC (LNL6 p=0.021; RRz2 p=0.034) and T-lymphocytes (p<0.0001 for both LNL6 and RRz2). Spearman rank correlation was used to quantify the relationship between the number of transduced cells reintroduced and subsequent marking of progeny PBMC and T lymphocytes. Analyses are based on values given in cells/kg for each patient. In these analyses, LNL6 marking is correlated with the quantity of LNL6-transduced cells reintroduced, and RRz2 marking is correlated with the quantity of RRz2-transduced cells reintroduced. The minimum number of transduced CD34+ cells that resulted in marking longer than one year was 0.5×10$^6$ cells/kg.

Vector sequences were detected in naïve cells up to 2.5 years post-infusion (the last time point evaluated). For example, FIG. 7c shows presence of vector sequences in highly enriched naïve cells in a representative patient.

Vector sequences were detected in naïve cells up to 3 years post-infusion (the last time point evaluated). FIGS. 7D-F show vector sequences in highly enriched naïve and memory cells from 4 to 130 weeks post-infusion in 3 patients. The average age and viral load of patients whose naïve T-lymphocytes had detectable vector sequences were 41 years (range 32 to 48 years) and 3,680 copies/ml (range: undetectable to 22,628 copies/ml) respectively. A summary of vector detection is naïve T-lymphocytes and viral load at the time of detection is shown in Table 2. We also analyzed fine needle aspirates of lymph nodes from 4 patients for the presence of vector sequences. Both LNL6 and RRz2 were detected in 2 of the 4 patients (patient 7 at 2.5 years post-infusion and patient 10, 1 year post-infusion).

Table 2—Naïve T-Cell Vector Detection Summary.

Circulating naïve T-lymphocyte populations were selected to purity >85% from CD4 and CD8 selected populations. Cells were analyzed by PCR. Viral load at the time point of vector analysis is shown under each symbol, ND: not determined. Two values indicate that two determinations are available from a time interval. NT: not tested; (+): LNL6, RRz2 or both vectors detected in CD4+ CD45+CD62L+ or CD8+ CD45+CD62L+(naïve) Tlymphocytes; (−): Neither vector detected in CD4 or CD8 naïve T-cells.

| PATIENT NUMBER | <3 MONTHS | 3 TO 6 MONTHS | 6-12 MONTHS | 12-24 MONTHS | >24 MONTHS |
|---|---|---|---|---|---|
| 1 | NT | NT | +<br>660 | NT | NT |

-continued

| PATIENT NUMBER | <3 MONTHS | 3 TO 6 MONTHS | 6-12 MONTHS | 12-24 MONTHS | >24 MONTHS |
|---|---|---|---|---|---|
| 2 | NT | NT | + 12,893 | NT | NT |
| 3 | NT | NT | − 782 | − ND | NT |
| 4 | + 590 | NT | + 22,628 | NT | NT |
| 5 | NT | NT | + 3,183 | + 3,899 | ++ 130/15,800 |
| 6 | NT | ++ 368/606 | − 2,905 | − | NT |
| 7 | + 4,509 | NT | + ND | + 12,496 | + ND |
| 8 | + ND | NT | NT | NT | NT |
| 9 | + ND | NT | + ND | + ND | NT |
| 10 | NT | + 925 | + 1,384 | + 4,562 | NT |

To determine whether the presence of the anti-HIV-1 ribozyme in CD4+ cells conferred protection against HIV infection, we measured LNL6 and RRz2 vector copy numbers by PCR in different cell types over time. Intra-construct comparisons of marking decay rate are implemented as mixed effect linear regression (Miller, 1986). Marking intensity is regressed on (a) (log) time since infusion, (b) an indicator of cell type, and (c) a time×cell type interaction term (multiplicative product). Mixed linear models analysis could be performed for these data because estimation algorithms consistently converged (models fit in SAS PROC MIXED). Intra-subject correlation of marking intensities was modeled using a "repeated measures" blocking structure for the data. Throughout these analyses, we fit models using either an unstructured variance-covariance matrix for residuals, or assuming a compound symmetric matrix. Substantively identical parameter estimates and significance tests emerged from each type of analysis.

A more sustained level of RRz2 marking in HIV vulnerable cell types than in cell types not subject to HIV-induced depletion is consistent with Rz2-induced protection providing a selective survival advantage for RRz2-transduced cells.

Figure 9A:
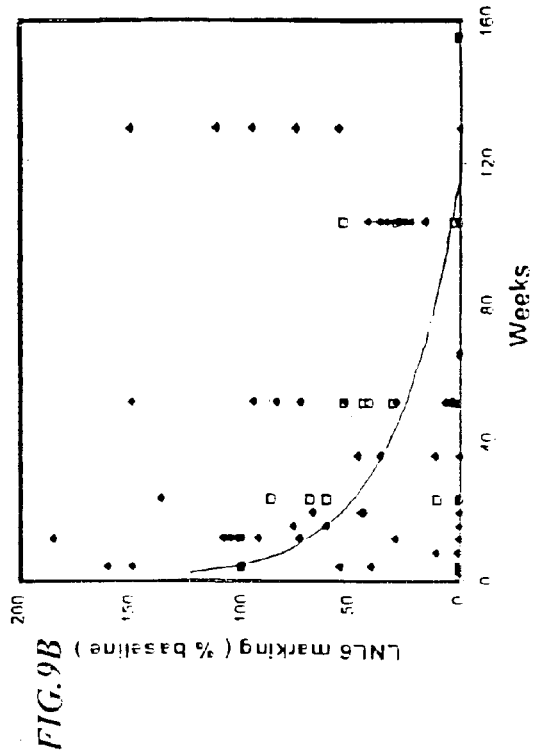
FIG. 9. Comparison between the kinetics of vector decay in T-lymphocytes and bone marrow mononuclear cells. Comparison of rate of decay of vector copies across T-lymphocytes and bone marrow mononuclear cells (BMMC) shows increased persistence of RRz2 marking in T-lymphocytes compared to that of LNL6 (A) LNL6 marking is shown in (B). Plots show vector marking level represented as percent of baseline, where baseline is defined as the average of vector copy numbers at weeks 4 and 12 for each cell type (red diamond and line: T-lymphocytes, open squares and black line: BMMC). (C) and (D) show the plots depicting the linear relationship between RRz2-transduced CD34+ cell dose, and difference between LNL6 and RRz2 copy number (protection index) in T-lymphocytes (C) and PBMC (D). (E), (F), (G) and (H) show the comparison between the kinetics of vector decay in T-lymphocytes and bone marrow mononuclear cells, and correlation with transduced-CD34+ cell dose infused. Ribozyme-induced protection against HIV-related cell depletion was assessed by comparing the decay of RRz2 and LNL6 vector DNA in cells vulnerable and nonvulnerable to HIV infection. Panel E shows detection of RRz2 and LNL6 vectors by PCR in CD4+ T-lymphocytes for patient 7 at the time points indicated. Radioactivity volumes for each band were normalized to known standards run in the same PCR reaction (not shown), and the ratio of RRz2 to LNL6 (values shown under each gel) was plotted against time (panel F). As a negative control for RRz2 protection, the plot of BMMC (which contain mostly cells invulnerable to HIV infection) is shown in panel F (PCR gels not shown). Trends over time in the ratio of RRz2 marking to LNL6 marking were estimated by linear regression, with P values reflecting the difference from a change rate of 0 (expected if RRz2 and LNL6 marking decay at equivalent rates). In this patient, the ratio of RRz2 to LNL6 marking in BMMC remained approximately constant over time (slope=−0.0005, difference from 0, P=0.281). In contrast, RRz2 marking increased relative to LNL6 marking over time in HIV-vulnerable T lymphocytes (slope=0.0036, difference from 0, P=0.008). The difference between trend lines was statistically significant (P<0.0006). To determine whether the magnitude of differential decay in LNL6 vs. RRz2 gene marking for a given patient was related to the number of RRz2-transduced cells infused, the difference between decay slopes of each vector for was correlated (spearman rank) with the number of RRz2-transduced CD34+ cells reintroduced. Patient-specific decay slopes for LNL6 and RRz2 marking were calculated by linear regression, and the difference between these slopes (RRz2-LNL6) was taken as an indicator of RRz2-mediated protection. Panels G and H show the plots depicting this linear relationship and confidence intervals (dotted lines) between RRz2-transduced CD34+ cell dose, and difference between LNL6 and RRz2 copy number (protection index) in T-lymphocytes (plot H) and PBMC (plot G).
Figure 9B:
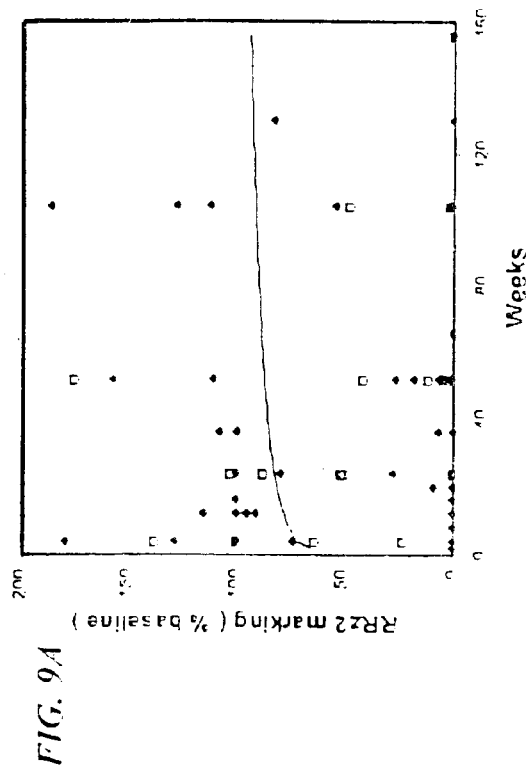

As shown in FIG. 9a, RRz2 marking decayed at approximately one eighth the rate in peripheral blood T-lymphocytes than in BMMC (−0.081 cells per log-week for T-lymphocytes vs. −0.643 cells for BMMC per log-week, difference p=0.0095). Unlike the decay rate of RRz2-containing BMMC, the rate of decay of RRz2-containing T-lymphocytes was not significantly different from zero, and the difference between both rates was significant (p<0.0001 for BMMC, p=0.55 for T-lymphocytes, p=0.009 for the statistical test comparing decay rates of RRz2-containing cells between both cell types). To exclude the possibility that these results are due to intrinsic decay rate differences between the cell types, LNL6 marking is shown in FIG. 9b. This analysis showed a decay rate of LNL6 copies of −0.716 for T-lymphocytes and −0.725 for BMMC. Both curves were significantly different from a zero decay rate curve (p values 0.0019 and 0.004 for T-lymphocytes and bone marrow respectively). The p value for the statistical test comparing the decay rates of RRz2 between both cell types was 0.97 reflecting near identical decay kinetics for the LNL6 vector. These comparisons were implemented as mixed effect regression models (Miller 1986). Consistent with the lack of protective activity against HIV conferred by LNL6, no differential decay was observed for LNL6 marking between these two cell types (p=0.9781), (FIG. 9b). These results show that statistically significant differences in marking decay rates between the two vectors were observed in favor of RRz2 in PBMC and T-lymphocytes, but equal decay rates were observed between vectors in the case of BMMC and granulocytes. Moreover, RRz2 containing naïve T-lymphocytes increased over time, whereas LNL6 containing ones declined (+0.145 vs. −0.240 per log week for RRz2 and LNL6 respectively, difference p=0.033). These results indicate that RRz2 confers a selective survival advantage to HIV-vulnerable cells, including recent thymic emigrants, in patients with HIV-1 infection.

We next sought to determine whether the magnitude of differential decay between T-lymphocytes containing LNL6 and RRz2 was correlated with the number of RRz2-transduced CD34+ cells that each patient received. To this end, the difference between decay slopes between both vectors for each patient was correlated with the number of RRz2-transduced CD34+ cells that were infused. Patient-specific decay slopes for LNL6 and RRz2 marking were calculated by linear regression, and the difference in slopes (RRz2-LNL6) was taken as an indicator of RRz2-mediated protection. Spearman rank correlation was used to examine relationships between differential decay rates and the numbers of transduced CD34+ cells infused.).

Figure 9C:
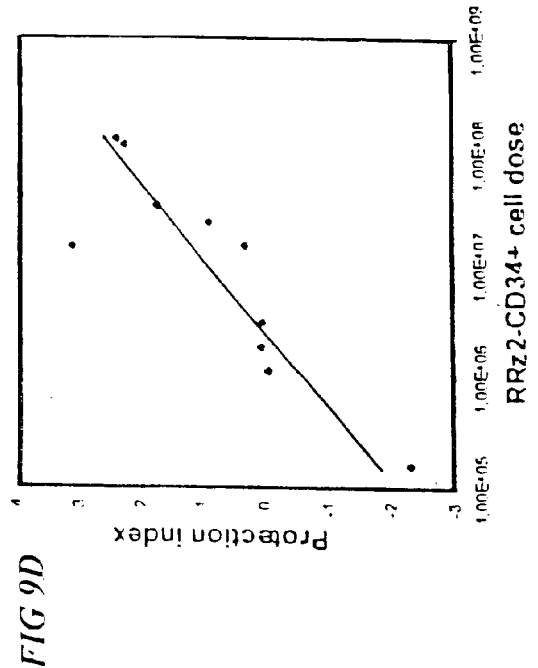
Figure 9D:
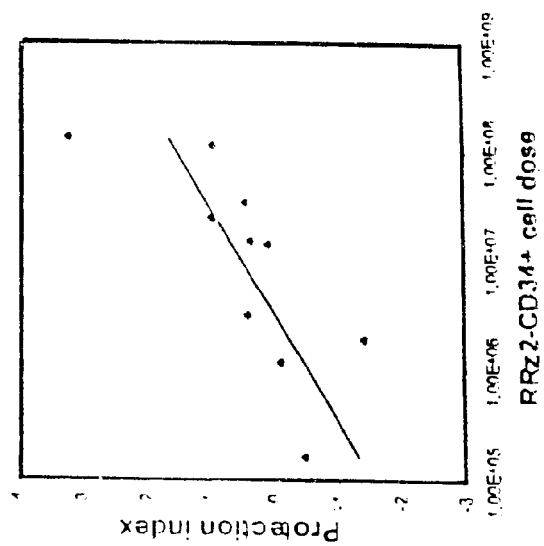
Figure 9F:
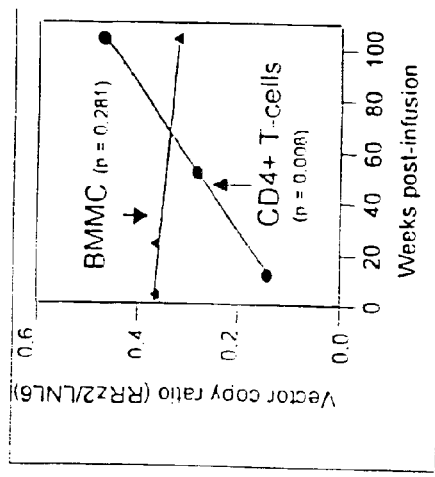
Figure 9H:
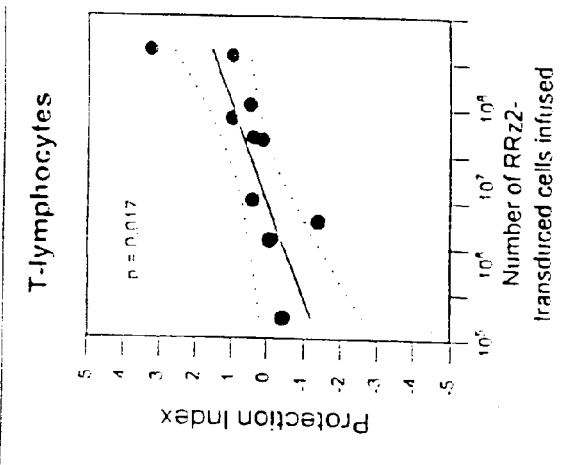
Figure 9E:
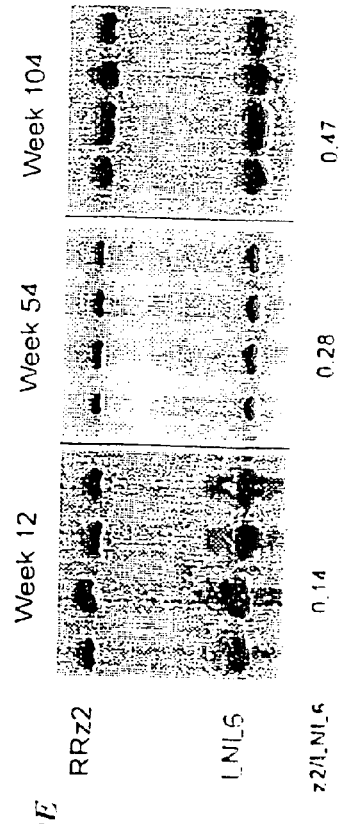
Figure 9G:
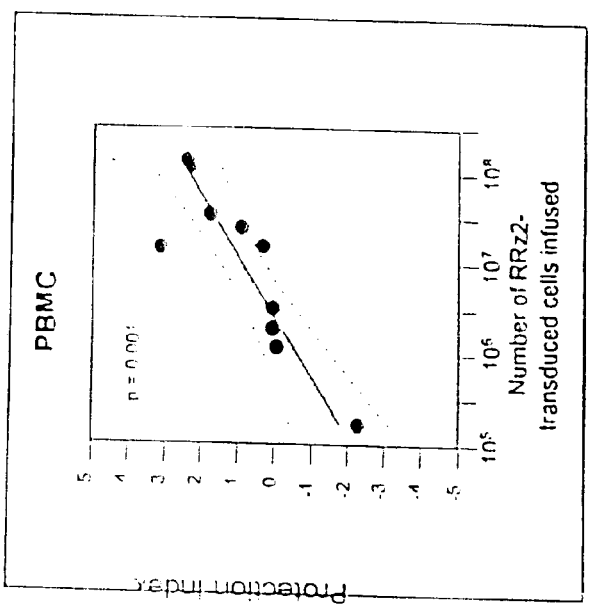

Plots depicting this relationship for T-lymphocyte and PBMC decay slopes are shown in FIG. 9c&d respectively. These analyses demonstrate a strong linear relationship between the number of transduced CD34+ cells that were infused and the magnitude of differential decay of LNL6 vs. RRz2 in both PBMC and T-lymphocytes. When reinfused RRz2-transduced CD34+ cell numbers are taken as a continuous variable predicting the differential decay of marking over time in a regression analysis, results are statistically significant with p<0.0001 (Regression coefficient t statistics for the interaction term in a regression of differential marking (RRz2-LNL6) on (log) time, infused cell number, and their product-term interaction). These data indicate that there is an unexpected dose dependent effect on differential survival between protected and unprotected HIV-1-vulnerable cells, and that clinical benefit using hematopoietic progenitor cell gene therapy strategies will be dependent on the dose of transduced progenitors administered to patients.

Figure 10A:
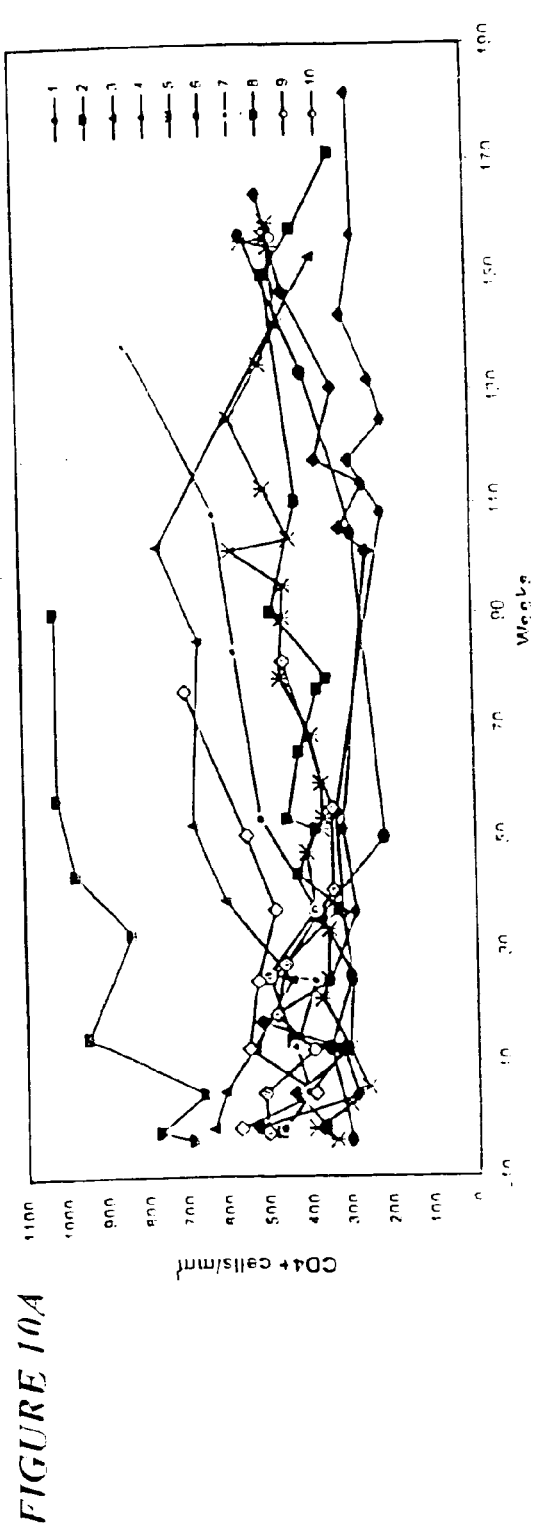
FIG. 10. Absolute CD4+ cell counts (A) and viral loads (B) in study patients. Absolute CD4+ cell counts per mm³ (A) and viral loads (B) in HIV RNA copies per ml of blood are shown for patient Nos. 1-10 through the study. An initial increase in viral load was observed at day 1 post-infusion in some patients who discontinued antiretroviral therapy during the period of mobilization. Drug discontinuation or substitution of nucleoside reverse transcriptase inhibitors for non-nucleoside reverse transcriptase inhibitor or protease inhibitor was included in the protocol to prevent potential inhibition of MMLV reverse transcriptase during transduction. Occasional rises in viremia were corrected after modification of antiretroviral therapy.
Figure 10B:
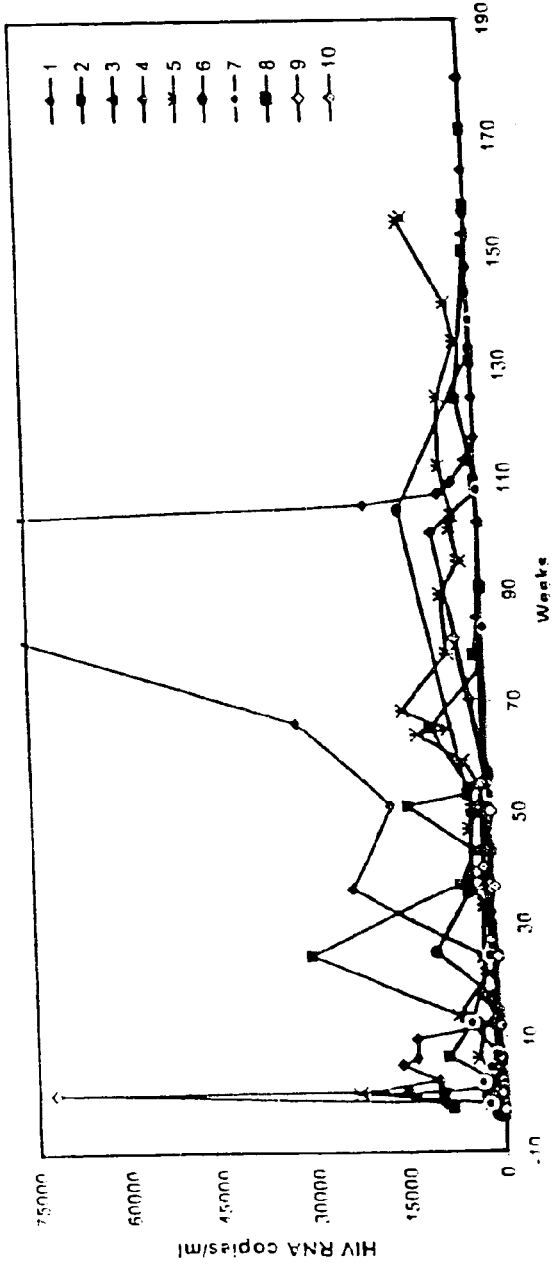
Figure 11:
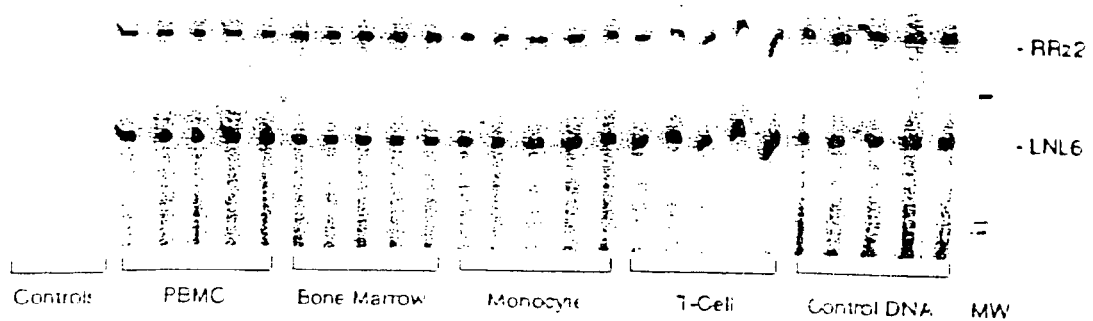
FIG. 11. Long-term marking of hematopoietic cell populations in Patient #005 from the Phase I Autologous CD34+ study. Shown in the gel are PCR amplified bands from LNL6 and RRz2 marked cells in bone marrow and peripheral blood populations 2 years post-infusion.
Figure 12:
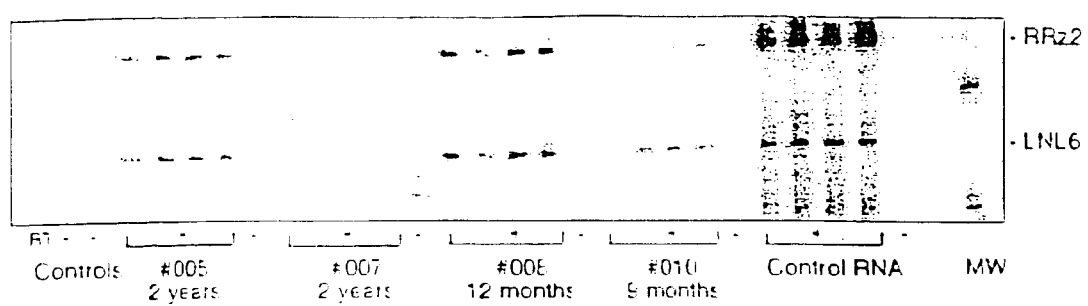
FIG. 12. Gene Expression in Peripheral Blood Mononuclear Cells in 4 patients from the Phase I autologous CD34+ cell study. Expression of both LNL6 and RRz2 is shown for 2 patients at 2 years post-infusion. Expression was assessed in a reverse transcriptase-nested PCR reaction using radiolabelled primer. For each sample, a reaction that did not contain RT (−RT) was included. Presence or absence of RT is indicated.
Figure 13:
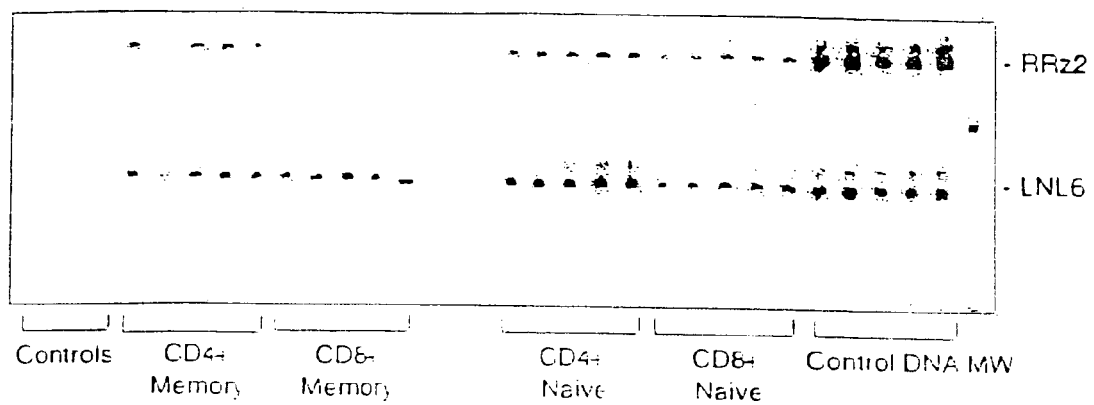
FIG. 13. Long-term marking of T-lymphocyte (CD4+, CD8+) sub-populations in Patient #007. Results show the marking in naïve and memory CD4+ and CD8+ lymphocytes 1 year post-infusion of the autologous LNL6 or RRz2 transduced CD34+ cells.

All patients in this phase I study have been receiving antiretroviral therapy and to date, none of the patients have developed opportunistic infections. The kinetics of CD4+ cell count and viral load are illustrated in FIG. 10. An initial increase in viral load was observed at day 1 post-infusion in some patients who discontinued antiretroviral therapy during the period of mobilization. Drug discontinuation or substitution of nucleoside reverse transcriptase inhibitors for non-nucleoside reverse transcriptase inhibitor or protease inhibitor was included in the protocol to prevent potential inhibition of MMLV reverse transcriptase during transduction (H. Bazin, et al., 1989). Occasional rises in viremia responded to modifications of antiretroviral therapy.

The average change in CD4+ T-lymphocyte count from entry to year 3 was an increase of 10 cells per mm$^3$ (range −40 to +80). Viral load decreased by an average of 2.25 logs in 6 patients (range 0.35 to 3.9), remained undetectable in 3 patients, and increased by 1 log in one patient. These changes did not correlate with the degree or persistence of vector detection or vector expression in any cell type, and are thought to be influenced by individual viral susceptibility to antiretroviral therapy.

Viral genotyping demonstrated multiple drug resistance mutations in all patients (data not shown). We also performed genotypic analysis of the Rz2 binding/cleavage region of HIV in all patients at study entry and at 12, 24, 52 and 104 weeks post treatment Ribozyme cleavage site analysis was done as previously described (Wang et al. 1998) with minor modifications. Briefly, viral RNA was extracted and reverse transcribed with the Access RT-PCR kit (Promega, Madison, Wis.) using Primer 1 (TGGCAATGAAAGCAACACT) (SEQ ID NO. 9) for 45 minutes at 48° C. The resulting cDNA was PCR amplified by addition of Primer 2 (TTTAGAGGAGCTTAAGAATGA) (SEQ ID NO. 10) for 25 cycles (94° C. for 20 sec., 55° C. for 30 sec., and 68° C. for 30 sec.). Single-stranded DNA for cycle sequencing was produced by a second PCR step using AmpliTaq (Perkin-Elmer) and Primer 3 (AGTTTTAGGCTGACTTCCTGG) (SEQ ID NO. 11) for 25 cycles at 94° C. for 20 sec., 55° C. for 30 sec., and 68° C. for 30 sec. Sequencing was performed on purified PCR products with the ABI PRISM Dye termination cycle sequencing Ready Reaction kit with AmpliTaq DNA polymerase (Perkin-Elmer) on an automated DNA sequencer (ABI Model 377, Applied Biosystems, Foster City, Calif.) using Primer 4 (TGGAAGCCATAATAAGAAT) (SEQ ID NO. 12). Sequence alignment was performed with Sequence Navigator software (Perkin-Elmer) and manually proofread and edited. The resulting sequence was compared to the HXB2 Glade B HIV-1 reference strain.

Six of the 10 patients had viral loads that permitted sequence determination. Patients 1, 2, 5 and 6 had wild-type sequences. Patient 4 had an A to C transition at position −1 from the GUA target triplet. Patient 7 had a G to T transition at position −4 from the GUA target triplet. Evidence indicates that the mutant RNAs are clearable by the ribozyme. The mutations detected in both these patients were present before treatment; hence they did not arise as a result of efficacy-induced resistance to the construct.

The studies described here were conducted in the absence of myelosuppression, therefore the engineered CD34+ cells contributed to form a chimeric hematopoietic system. Transduced CD34+ cells must compete with endogenous stem cells for hematopoietic reconstitution. Indeed our results indicate a correlation between cell dose and the length of engraftment with transduced cells. Because no survival advantage is expected to occur at the level of the transduced CD34+ cells, and given the established correlation of survival to numbers of infused CD34+ cells, future studies will aim to increase the number of gene modified cells administered. Recently, it was reported that genetic correction of the yc cytokine receptor deficiency that characterizes human severe combined immunodeficiency (SCID)-X1 disease leads to the development of a functional immune system (Cavazzana-Calvo et al. 2000). With regards to the application of gene correction strategies, the HIV-infection model is different from the SCID-X1 model. Unlike in the setting of HIV/AIDS, where both transduced and non-transduced CD34+ cells can contribute to thymopoiesis, in the SCID-X1 case, where the resulting functional receptor mediates survival signals, thymopoiesis results only from CD34+ cells that contain the exogenous gene. Thus, in HIV infection, a survival advantage at the level of the CD4+ T-lymphocyte resulting in an expansion of these ribozyme-carrying cells would presumably take place in the presence of HIV replication. In this case the virus provides the selective survival pressure, as unprotected cells would remain vulnerable. This hypothesis was not tested in our study, as our patients have remained on antiretroviral therapy. It is possible that a greater degree of preferential survival may occur in the presence of uncontrolled viral replication.

These studies have shown that gene constructs can be retrovirally introduced into CD34+ hematopoietic progenitor cells, and that these cells will contribute long-term to multi-lineage hematopoiesis in HIV-infected patients. Our study represents the second report of a stem cell gene therapy trial in HIV infection. A previous trial employing a retroviral vector containing a rev-responsive element decoy gene in pediatric patients resulted in detection of the anti-HIV gene in 2 of the 4 patients only on one occasion at day 1 following cell infusion. Control vector was detected at low levels in all 4 patients at 30 days, in 3 patients at 90 days and in 1 patient 250 and 330 days post-infusion (Kohn et al. 1999). These results contrast with our long-term reconstitution results. Based on our results, the short-term marking observed in the previous report seems to be due at least in part to low doses of transduced CD34 cells administered. Whereas previous HIV gene therapy studies using transduced T-lymphocytes have shown longer persistence of a therapeutic-vector as compared to a control vector up to a year after infusion (Ranga et al. 1998), ours is the first report to indicate that T-lymphocyte development ensues long-term from genetically modified hematopoietic progenitors in the context of HIV infection, and to show evidence of cell protection of naïve and memory T-lymphocytes against HIV-induced depletion. The finding that sustained production of transgene-containing naïve T-lymphocytes occurs even in patients with detectable viremia is significant, given that naïve thymocytes are known to be infected by HIV (Ostrowski et al. 1999), and that the thymus can act as a source of HIV-1 latency during T-lymphocyte differentiation (Brooks et al. 2001). As thymopoiesis continues in the adult patient, replacement of this naïve T-lymphocyte-based latent pool with cells that are engineered to effectively inhibit virus replication should result in restoration of protected immune cells and in inhibition of viral rebound following withdrawal from antiretroviral therapy, or after the development of drug resistance. The presence of ribozyme sequences in other viral reservoirs such as monocytes could also contribute to control of virus replication in these settings. Such results justify further exploration of anti-HIV stem cell gene transfer as a form of anti-HIV therapy.

Example 3

Specific Methods Used 3.1 *Mycoplasma* Assay

Following culture and transduction, the harvested cell cultures were tested for mycoplasma. The procedure used was based on the amplification of a mycoplasma-specific DNA sequence by PCR and subsequent detection of the amplicon by ELISA. The procedure used the *Mycoplasma* PCR ELISA test kit (Boehringer Mannheim, Cat #1 663 925). Test samples (1 sample per donor) and a negative control sample (1 ml aliquot of fresh RPMI culture media containing 5% human serum albumin) were centrifuged in microcentrifuge tubes at maximum speed for 10 minutes at 4° C. to sediment any mycoplasma. To solubilize the pellet, 10 μl of sterile water and 10 μl Lysis Reagent (solution 1 of the kit) was added. Further processing was carried out according to the kit instructions. Cross-contamination of samples and reagents in the PCR procedure was avoided by using fresh aerosol tips for all pipetting steps. Each experiment included two negative controls and a positive assay control. The PCR amplification used 1 cycle of 5 min at 95 $C_{1-39}$ cycles of 30 secs at 94° C.; 30 secs at 62° C.; 1 min at 72° C., ending with 10 min at 72° C. After the ELISA step according to the manufacturers instructions, negative controls were accepted if they were lower than 0.25 $A_{450}$-$A_{690}$-units, if not the assay was repeated. Positive assay controls were accepted if they were higher than 1.2 $A_{450}$-$A_{690}$-units, if lower the assay was repeated. Samples were regarded as positive for mycoplasma contamination if the absorbance was more than 0.2 $A_{450}$-$A_{690}$-units higher than the negative controls.

3.2 Endotoxin Assay.

The presence of endotoxin was determined in the cell cultures following culture and transduction for two reasons: the presence of low level endotoxin in the cultures would be an indication of a possible previous contamination by Gram negative micro-organisms, and secondly, high levels of endotoxin are toxic to cells in culture. This assay was carried out on the day of harvest after transduction, prior to infusion. The assay was carried out using the QCL-1000 *Limulus Amebocyte* Lysate kit (BioWhittaker # 50-647U) according to the manufacturers instructions. A stop solution consiting of 0.25% glacial acetic acid was prepared as it was not provided with the BioWhittaker kit. One kit was sufficient for 5 patient cultures. Results were analyzed with Softmax software. If the results of the diluted infusion sample or diluted VCM sample were greater than 5 EU/ml, the infusion would not have been proceeded with. If the results of the undiluted infusion sample or undiluted VCM sample were greater than 0.3 EU/ml, the Gram stain results were referred to for confirmation of a possible contamination by bacteria in the infusion bag. Otherwise the infusion was proceeded with.

3.3 Gram Stain.

Gram staining was used to test for Gram positive and Gram negative bacteria in cell cultures before infusion. Quality controlled slides, which have positive and negative controls incorporated (Fisherbrand Gramv QC slides cat #08-80) and the Fisher diagnostics Gram Stain Set (Cat #SG 100D) were used according to the manufacturers instructions. A 5 µl sample of each infusion mixture was smeared evenly on the slides. After staining, slides were examined under a 100× objective with immersion oil. Control squares in the first column marked with "+", containing Gram positive *Staph. aureus* appeared as dark purple round dots. Control squares in the first column marked with "−" containing Gram negative *E. coli* appeared as red-pink rods. If the controls did not look like this, the staining was repeated. If the infusion samples had contained any objects looking like the controls, infusion would not have proceeded. Cultured cells showed up as relatively large objects and cell membranes as pale wispy shreds.

3.4 Preparation of Co-cultivation and Amplification Samples for RCR testing.

The patient retrovirus-transduced cells and the transduced cell culture supernatant were tested for replication competent retrovirus (RCR). Per U.S. Food & Drug Administration (FDA) requirements, 1% or 108 of the total transduced patient cells (whichever was less) for each patient was tested in a *Mus dunni* co-cultivation assay and 5% of the transduced cell culture supernatant was tested in the *Mus dunni* amplification assay. These assays were performed at BioReliance Corp., (formerly MA BioServices in Rockville, Md., USA). Samples for these assays were taken at the time of cell harvesting and preparation for infusion and stored until all patient tranduction/harvest procedures were completed and then shipped for testing.

Amplification RCR Samples were prepared for storage as follows. Supernatant samples from the final harvested CD34$^+$ cells were prepared in triplicate and consisted of alignots of clarified supernatant (5% total volume per tube). They were stored at −80° C. until the final transduced patient amplification sample had been collected. Duplicate RCR Co-cultivation Samples were prepared for storage, using 2% of each CD34$^+$ cell batch per sample, and resuspended in cryopreservation media. Samples were then stored in liquid nitrogen until time of shipment. Enough cells were included to assure that the correct number of viable cells (1%) would be achieved upon thawing of the sample at BioReliance Corp. laboratories.

3.5 Plasma/PBMC/Bone Marrow Isolation.

Blood samples and bone marrow samples were collected from patients at screening prior to infusion and at various time points up to at least 3 years after infusion. The blood was collected into 10 ml ACD tubes, the volume collected depending on the tests required. From these blood samples, plasma was collected and PBMC prepared as cell pellets or cryopreserved samples. BMMC were prepared from bone marrow and used fresh for CFC assay and the remainder cryopreserved. The procedures used were as follows.

Collection of plasma: Blood tubes (10 ml, ACD-A vacutainers) were centrifuged for 10 minutes at 2000 rpm. The plasma fraction from each tube was carefully collected and pooled into a 50 ml sterile tube. 2 ml volumes of plasma were aliquoted and stored at −80° C.

Preparation of PBMC: Using the erythrocyte/leukocyte cell pellet after collection of the plasma, the cells were diluted to 3 times the initial starting volume with Wash Buffer and distributed in 30 ml lots in 50 ml centrifuge tubes. Each dilute cell suspension was underlaid with 10 ml Ficoll-Paque (Pharmacia Cat#17-0849-03) and centrifuged at 2000 rpm for 20 min at 20° C. in a swinging bucket rotor. The upper layer was aspirated, leaving the mononuclear cell layer undisturbed at the interphase. The interphase cells were transferred to a new 50 ml tube, pooled if appropriate, washed with Wash Buffer, centrifuged at 1500 rpm for 15 min, and the pellet resuspended in 5-10 ml Wash Buffer. A viable cell count was carried out on 50 µl cell mixture using a hemacytometer and Trypan Blue (1:25 dilution). The cells were aliquoted at 1-2× 10$^6$ cells per tube and stored frozen if required, and lysed with 140 µl Urea Lysis Buffer. For cryopreservation, cells were resuspended at 1-5×10$^6$ cells per ml in PBMC Cryopreservative Medium and cooled gradually in liquid nitrogen for storage.

Preparation of Bone Marrow Mononuclear Cells (BMMC): Bone Marrow was diluted 1:1 with Wash Buffer, and 30 ml samples underlaid with Ficoll-Paque and treated as above for PBMC. Viable Cell counts were carried out on 30 µl samples and the volume required for CFC assay (2.5-3×10$^6$ cells) put aside for the assay. All remaining BMMC was cryopreserved at 1×10$^7$ cells per ml of CD34$^+$ Cryopreservation Medium.

3.6 Screening Sample Bone Marrow CFU Assay

CFU assays were performed on bone marrow from patients prior to infusion, thereby providing a baseline or control for all other colony assays performed after infusion. As the cells had not been exposed to a gene therapeutic or control, they were not selected on G418. All procedures were performed in a biocontainment hood and aseptic technique was applied at all times.

BMMC prepared as described above were aliquoted into three 1.5 ml sterile microfuge tubes at 1.5×10$^6$ cells, 7.5×10$^5$ cells, and 3×10$^5$ cells per tube. The samples were centrifuged at 2500 rpm for 2 min, the medium aspirated and the cell pellets resuspended thoroughly in 300 µl of RPMI (Gibco BRL, Cat # 118-030)+1% FBS (Stem Cell technologies, Cat# HCC-6450). The cell mixtures were pipetted into tubes (6 ml polystyrene Falcon, Cat#2058) each containing 3 ml of Methocult GFH4434 (Stem Cell Technologies, Cat# HCC-4434). The contents were vortexed thoroughly for at least 15 seconds, let sit until bubbles settled, and 1.1 ml aliquots layered carefully onto grid dishes (Nunc Cat# 174926) arranged in a petri dish. The petri dishes had an additional grid dish containing sterile water, opened to maintain humidity during culture. The petri dishes with the grid dishes were incubated at 37° C. in a humidified incubator and colonies observed after $10^{-14}$ days.

3.7 Post-Infusion CFC Assay.

The post infusion Colony Forming Cell (CFC) assay included cultures with and without G418. This was used to assess transduced progenitor cell development following infusion. Two cell numbers/dish are used to ensure that colonies are at an optimum density when picked.

BMMC were prepared as described above and aliquoted at $6 \times 10^5$ or $1.5 \times 10^6$ cells to sterile microfuge tubes. The cells were pelleted at ~2500 rpm for 2 min. The medium was aspirated and the cell pellets resuspended thoroughly in 600 µl of RPMI+1% FBS. 300 µl of each cell mixture was added to tubes containing 3 ml of Methocult GFH4434 (StemCell Technologies, Cat# HCC-4434), one +G418 at 0.9 mg/ml (G418, crystalline geneticin, Gibco-BRL Cat # 11811-031) and the other without—G418. The samples were then vortexed and further treated as described above for the Screening Sample Bone Marrow CFU Assay.

3.8 T-Cell, Monocyte and Granulocyte Preparation from Blood.

Leucocytes were isolated from patient's blood at several time points after infusion. These cells were fractionated into 3 types (the T-cell, macrophage and granulocyte lineages) to follow RRz2 or LNL6 presence and HIV levels. The blood was first separated on 1-Step Polymorphs into erythrocytes, granulocytes, and peripheral blood mononuclear cells (PBMCs) The PBMCs are further fractionated on two columns: A CD3 column to yield lymphocytes and a CD14 column to yield monocytes. The granulocyte fraction was assessed for purity by Giemsa stain and the Lymphocyte and monocyte fractions were FACS stained to assess purity. All fractions were treated to prepare cell lysates for later DNA extraction and PCR analysis.

All procedures were performed in a Class II Biological Containment cabinet. 5 ml of fresh, ACD anticoagulated, human blood in 10 ml tubes, collected less than 2 hours previously and kept at room temperature, was overlaid on 3.5 ml of 1-Step Polymorphs (Accurate Chemical & Scientific Corporation, Cat# AN221710, store at room temperature and protect from light).

The tubes were centrifuged at 1650 rpm for 30 minutes at room temp in a swinging-bucket rotor. After centrifugation, two leukocyte bands were visible. The top band at the plasma/1-Step interface consisted of mononuclear cells and the lower band of PMN cells (Granulocytes). The erythrocytes are pelleted. All but about 1 ml of plasma was aspirated and transferred to a "Plasma" tube, leaving the mononuclear cell layer undisturbed at the interface. All plasma collections were pooled for each patient, aliquoted in 2 ml lots and kept for later preparation of the granulocyte stain. The PBMC interface cells were carefully transferred to a "PBMC" tube, being careful not to pick up the lower band. All PBMC collections were pooled for each patient. The lower band was transferred to a "Granulocyte" tube and pooled. An equal volume of hypotonic PBS was added to the granulocyte tube. Both the "PBMC" and "Granulocyte" tubes were filled with wash buffer up to 50 ml, mixed and centrifuged at 1500 rpm for 15 minutes at room temperature. The supernatant was aspirated and the cells washed once with 50 ml of Wash Buffer. After pelleting, the cells were resuspended in 10 ml of PBS. A cell count was performed (1:20 dilution with PBMC cell suspension and a 1:5 with the Granulocyte suspension).

Granulocyte cell pellet/lysate preparation and phenotyping: The original suspension or cell pellet was resuspended to a final concentration of $1 \times 10^7$ cells/ml, if necessary repelleting the cells first. 100 µl was transferred to a microfuge tube for phenotype staining. These cells were pelleted in a microfuge at ~3000 rpm for 1 minute, suspended in 10 µl of plasma fraction, and 5 µl of this concentrated suspension smeared onto each of two microscope slides. The slides were air dried, stained with Giemsa stain for 30 min, rinsed with distilled water and let air dry. They were examined under a 20× objective and the fraction of granulocytes counted. The remainder of the Granulocyte cells were pelleted in a microfuge at 3000 rpm for 2 minutes for late DNA exraction.

3.9 DNA Preparation from Cells (Vacutainer-Phenoling DNA).

Vacutainers (Hemogard, SerumSep, 6 ml. Cat# 369789) were used for some DNA extractions. This was a rapid way to extract genomic DNA from CD34 selected cells, methylcellulose colonies, and patient PBMCs. 1 or 2 million cells in a 1.5 ml microfuge tube were pelleted at 3000 RPM for 3 minutes in the microcentrifuge, washed once with 1 ml of PBS and then dispersed in 70 µl of water. 140 µl of Urea Lysis Buffer was added to each tube, and the phases mixed throughly by vortexing the tubes five to eight times. These tubes can be kept frozen at −70 C indefinitely. For each sample, 0.5 ml 10 phenol solution (Tris equilibrated United States Biochemical #20083, with 0.4 g of hydroxyquinoline hemisulfate added per 400 ml) was added, and the mixture pumped 2 or 3 times using a 1 ml syringe with a 23 or 25 G needle, then squirted into a vacutainer containing 210 µl of water. 15 µl of chloroform was then added to each vacutainer. They were capped, centrifuged at 2400 rpm for 5 min, then 0.5 ml of phenol/chloroform added. They were shaken for 30 seconds and recentrifuged at 2000 rpm for 3 min. The phenol/chloroform extraction was repeated, followed by two extractions with chloroform/isoamyl alcohol. 400 µl of the extract above the plug was transferred to a microfuge tube with an aerosol-resistant tip, and the DNA precipitated with 25 µl 5 M NaCl and 850 µl absolute ethanol at −20° C. The DNA was recovered by centrifugation, washed once with 70% ethanol, air dried, and resuspended in 50 µl water or 5 mM Tris pH 9. For PBMC fractions or bone marrow samples, 20 µl was used for each $10^6$ cells. DNA preparations were stored at −70° C. For samples from colonies, the 210 µl water in the vacutainers contained 10 µg tRNA (Sigma R 9001) as carrier.

DNA was also prepared from cells using the "Acest Protocol" and used in competitive PCR and PCR-RCR assays. Cell pellets of approximately $5 \times 10^6$ cells in a microfuge tube were resuspended in 300 µl lysis buffer (10 mM Tris-HCl, 50 mM KCl, 3 mM $CaCl_2$, 0.4% Triton×100, pH 8.0, filter sterilized), 3 µl of PreTaq (Boehringer Mannheim Cat #1696491) added, the sample boiled for 5 min and centrifuged at 13000 rpm for 2 min. The supernatant was transferred to a clean screw-capped 1.5 ml tube, 100 µl ACES Buffer (2.28 Aces (Sigma Cat. No. A-7949), 12.5 ml 05M NaOH, 12.5 ml Tween-20, pH6.8, in total volume 50 ml, filter sterilized) and 25 µl Polymer (Ward et al 1998) added, the sample mixed by vortexing briefly and then centrifuged for 2 min at 13000 rpm. The pellet was resuspended in 50 µl of 20 mM NaOH and left at room temperature until thoroughly dissolved. The sample was boiled for 5 min and the DNA concentration determined by measuring the optical density at 260 nm. Extractions from post-infusion cells were carried out under PC3 containment due to HIV presence.

3.10 PCR

For detection of LNL6 or RRz2 sequences in cells or cell colonies, PCR analysis of cellular DNA was carried out. PCR primers were labelled with P32 to enable quantitative detection of the PCR product. Labelling was carried out with $\gamma^{32}P$-ATP (ICN # 3502005) and T4 Polynucleotide kinase (GIBCO-BRL Cat# 18004-010) by the recommended procedure. Excess unincorporated label was removed using G25 Sephadex spin columns. 10× buffer was used for PCRs, containing 250 mM Tris, 50 mM $MgCl_2$, 500 mM NaCl, 2.5 mM each of dATP, dCTP, dGTP, TTP (Gibco BRL 10297-018), 1.0 mg/ml BSA (Sigma A-4378, made up as 100 mg/ml), pH 8.0.

Standards of pLNL6 and pRRz2 DNA were diluted in 5 mM Tris, pH 9 to give 1,000 and 100,000 copies per µl using human liver DNA as carrier and subsequently diluted to give a range of 5-5000 copies per 5 µl sample. For human beta globin analysis, human DNA standards were made from a 1 mg/ml stock to make dilutions at 10,000, 3000, 1000, 300 and 100 gene copies per µl.

LNL6/RRz2 "High copies": Method used for quantitating relatively high levels of LNL6 and RRz in preparations of DNA. Such DNA was derived from CD34 cells and hematopoietic colonies. In this protocol the PCR reactions were of 25 µl with no more than $10^4$ copies of the human genome. Oligonucleotide primers were 5L1A, 3L1D, Taq polymerase from Fisher. Amplification was carried out at 94° C. for 3 min, 68° C. for 1 min, followed by 27 cycles of 94° C. for 1 min and 68° C. for 1 min using an MJ Research Programmable Thermal Controller. Ten standard (control) samples were also treated, containing 5000, 1000, 500, 100, 50, 10, 5, 0, 0, and 0 copies of RRz2 and 0, 0, 0, 5, 10, 50, 100, 500, 1000, and 5000 copies of LNL6, respectively, all in the presence of 5000 copies of the human genome.

LNL6/RRz2 "Low copies": Method used for quantitating relatively low levels of LNL6 and RRz in preparations of DNA. Such DNA was derived from peripheral blood cells (lymphocytes, macrophages, and granulocytes). In this protocol the reaction was run on 50 µl samples with approximately 106 copies of the human genome. 20 µl of DNA samples were mixed with 30 µl containing primers 5L1A and 3L1D (one labeled), buffer and polymerase, and treated as for the "High copies" except that the 94° C. steps were for 90 seconds. The standard samples were in the presence of 106 copies of the human genome.

Amplified samples were analyzed on 5% or 6% polyacrylamide gels by electrophoresis using Tris-Borate-EDTA buffer (10× TBE, 0.89M Tris borate pH 8.3+20 mM EDTA) and radioactivity in bands quantitated using an AMBIS 4000 Radioimager.

As an additional standard, beta globin DNA was quantitated in preparations of DNA where the number of copies of the human genome was=10000. Such DNA was derived from $CD34^+$ cells and hematopoietic colonies, and patient PBMCs, T-cells, and bone marrow. Amplification was carried out using oligonucleotide primers LX1 and LA2, and 25 cycles of 94° C. for 1 min, 65° C. for 2 min.

A nested radioactive PCR method was also used to calculate the ratio of LNL6:RRz2 marking where less than approximately 0.01% of cells contain either construct. The two rounds of PCR provided increased sensitivity and the incorporation of radioactive label readily allowed quantitation using Imagequant software. Meticulous laboratory technique was used to avoid cross-contamination and appropriate controls carried out. The first round of PCR used 1 µg of template DNA, primers 5Nes1 and 3L2A, Buffer II (Perkin Elmer Cat #$N_8O_8$-0010) with 2 mM MgCl2, dNTPs and Taq DNA Polymerase (Perkin Elmer Cat #N801-0060) in 50 µl volumes with taqbeads (Perkin Elmer Cat #$N_8O_8$-0100). Amplification was carried out for ten replicates of each sample in Thermofast 96 PCR plates (Advanced Biotechnologies, Cat #AB0600) using 1 cycle at 94 $C_{1-17}$ cycles of 30 sec/68° C. and 30 sec/94° C., and cooling to 4° C. Products from the ten replicates were pooled and 5 µl pooled sample used for each second round amplification reaction. The second round PCR used labelled primer 5L1A and primer 3L2A under the same conditions as the first round except that 35 cycles of amplification were carried out. Products were analysed on polyacrylamide gels. The 216 bp product corresponded to RRz2, the 174 bp product to LNL6.

3.11 RCR-PCR.

The RCR-PCR assay allowed the detection of replication competent retrovirus by amplifying a highly conserved region of the env gene. The amplified sequence encodes part of the host-determining region of the envelope protein which is required for infection of cells through the amphotropic receptor. The amplified region was 289 bp long. The sensitivity of the assay was one positive cell in a background of one million negative cells ($10^{-6}$).

The PCR reaction used 7 µl DNA sample and the primers 5RCR6=5'-CTA TGT GAT CTG GTC GGA GA-3' and 3RCR6=5'-CCA CAG GCA ACT TTA GAG CA-3' with Buffer II (Perkin Elmer, Cat # $N_8O_8$-0010) and $Mg^{2+}$ (Perkin Elmer, Cat# $N_8O_8$-0010), 0.25 mM dNTPs (Gibco BRL 10297-018), and Taq polymerase (Taqbead™ DNA Polymerase, Promega, Cat # M5661). Amplification was carried out with 3 min at 94° C., followed by 45 cycles of 94° C. for 30 secs, 63° C. for 30 secs and 72° C. for 30 secs. Amplified samples were analyzed on 2.5% NuSieve gels. Presence of the 289 bp band indicated the presence of RCR.

A "no DNA" control containing water instead of sample DNA was run in each PCR experiment to verify that there was no contamination of any reagent. A negative control (CEMT4 DNA) was also run to ensure the specificity of the amplicons generated. A positive control ($10^{-5}$ PA317) was run in each PCR to verify that the sensitivity of the PCR was at least 1 positive in 100,000 negative cells. "PA317 spiked" samples, referring to the addition of 10 µl of $10^{-3}$ PA317 'spiking' DNA at 20 ng/ml, was also included in each experiment to all test samples in replicate PCR tubes. The addition of this positive, $10^{-3}$ PA317 DNA verified that a negative PCR result was a true negative for RCR, not a false negative result due to unamplifiable DNA. All manipulations involved meticulous laboratory technique to avoid cross-contamination, for example cleaning benches and pipettes with 0.1 M sodium hydroxide, frequent changing of gloves and use of aerosol barrier tips.

3.12 Colony Isolation in CFC Assay

The CFC assay was performed on patient bone marrow cells, $CD34^+$ enriched cells from apheresis, and the final transduced product. Colonies from the assay were analyzed by PCR for the LNL6 and RRz2 genes as described above. Cells from colonies after 14 days growth in methocellulose medium were isolated and lysed as follows. Under microscope, individual colonies were aspirated with P200 aerosol-resistant tips and flushed into microfuge tubes. Tips were rinsed with PBS to remove all methocellulose. The samples were vortexed at medium speed for 15 seconds to dissolve the methocellulose without shearing cells. DNA was isolated from the cells after lysis as described above.

3.13 RNA Extraction and RT-PCR Analysis

RNA was extracted from patient samples using the QIAmp RNA Blood Mini Kit (Qiagen Cat No 52304) by following the manufacturers instructions. RNA was extracted from 1-5× $10^6$ cells and resuspended in 50 µl RNase-free water. After DNase treatment of the RNA preparations using RQ-1 DNase (Promega, Cat No. M6101), synthesis of cDNA was carried out by using approximately 700-1000 ng RNA per reaction, primer 3L2A, and enzyme Superscript RNase H minus RT (Gibco Cat No. 18053-017) at 37 C for 45 min. Seven replicates were performed for each RNA sample and the products pooled before use as template in the nested PCR method described above.

Example 4

The HP cells are harvested, transduced and re-infused as follows. The method comprises the following steps:
HP Cell Mobilization from the human subject's bone marrow into the peripheral blood;
Apheresis of the peripheral blood of the individual to obtain the mobilized HP cells;
Washing Step #1; washing of the unpurified peripheral blood mononuclear cells by using a cell washer in preparation for de-bulking;
De-bulking Step; to remove excess red cells, granulocytes, platelets, and T-lymphocytes;
Washing Step #2; of the enriched HP cells using a cell washer;
$CD34^+$ Cell Selection or depletion of antigen positive cells from the HP cell population;
Washing Stop #3, washing of the purified HP cells using a cell washer;
Cell Culture by placing the purified HP cells into culture with cytokines/growth factors;
Transduction Procedure of the HP cells by using a retroviral vector containing the gene construct in the presence of a transduction-facilitating agent, preferably introducing the viral vector introduced using a cell washer;
Harvest Cell Product and wash the HP cells, including the transduced HP cells using a cell washer;
Preparation of Infusion Product, placing the HP cells into an infusion bag and perform product safety release testing; and
Infusion of Patient, delivering the cells back into the same subject.

These steps are described in more detail with examples and other modifications as follows:
Step 1-HP Cell Mobilization.

The first step of this procedure uses an agent to mobilize HP cells from the bone marrow into the peripheral blood. An example here is the use of Granulocyte Colony Stimulating Factor (G-CSF, Neupogen™) which is administered to the patient subcutaneously, at least at 10 μg/kg/day and preferably at 30 μg/kg/day, once daily, for up to five consecutive days. Complete Blood Counts (CBCs), differential and platelet count are performed daily during G-CSF administration to assess the extent of the leucocytosis. A blood sample for $CD34^+$ cell count is drawn on day 3 of G-CSF administration to ensure that the peripheral blood $CD34^+$ count is greater than 20 cells/mm$^3$ prior to the start of apheresis. Failure to attain this $CD34^+$ cell number does not however prevent apheresis on days 4, 5 and 6 of G-CSF administration.
Step 2-Apheresis.

Apheresis is a method of "blood filtration" to obtain the mononuclear cell fraction of the peripheral blood. It is conducted with a Cobe Spectra (Gambra), Hemonetics (Domedica) or Amicus (Baxter) machines on at least two separate occasions, (preferably on days 4, 5 or 6 following mobilization, where day 1 is the first day of induced mobilization), though in other examples this can be done on earlier or later days by determining the day at which the peripheral blood $CD34^+$ count is greater than 5 cells/mm$^3$ or more preferably 10 cells/mm$^3$ and most preferably 20 cells/mm$^3$. In a preferred embodiment, this apheresis yields cellular product from about 5 Liters (L) of blood flow through, preferably this will be 5-10 L, but more preferably 10-20 L, and more preferably still 20 L or greater. Product from each apheresis is either treated separately or, in a preferred embodiment, pooled after the second apheresis. Total cell counts, and absolute $CD34^+$ cell numbers are recorded. Use of Steps 1 & 2 will produce up to greater than $5 \times 10^6$, preferably greater than $2 \times 10^7$, more preferably greater than $4 \times 10^7$ HP (as measured by CD34 positivity) cells/kg
Step 3—Washing Step #1 (Preferably on Days of Apheresis).

The pooled cells are washed. This is done by cell centrifugation or more preferably using an automated cell washer, in one example this cell washing is done by using a Nexell CytoMate washer.
Step 4—De-Bulking Step (Preferably on Days of Apheresis).

In one embodiment, the cells from the apheresis procedure(s) are "de-bulked" using a system like a Charter Medical DACS—SC™ system. In the embodiment where product is stored overnight from the first day for pooling with second day product, the two apheresis products are de-bulked on the day of collection and the first product stored until the second product has been de-bulked.
Step 5—Washing Step #2 (Preferably Day 6).

The cells are taken, pooled (in the embodiment where there are two products) and washed by centrifugation or by using a Nexell CytoMate device or similar. (If there are more than two products all will be pooled at the latest time point).
Step 6—$CD34^+$ Cell Selection (Preferably Day 6).

$CD34^+$ cells are selected from the post-washing product by using the Isolex 300i, Miltenyi or a lineage depletion strategy of cells expressing markers (e.g. CD2, CD3, CD14, CD16, CD19, CD24, CD56, CD66b glycoprotein A, StemSep). The enriched pool of $CD34^+$ or lineage depleted cells preferably comprises at least 40%, more preferably at least 60% and most preferably at least 80% cells of this type.
Step 7—Washing Step #3 (Preferably Day 6).

The cells are washed by centrifugation or by using the Nexell CytoMate or similar equipment.
Step 8—Cell Culture (Preferably Days 6-9).

The cells are counted and placed at preferably $1 \times 10^5$ to $5 \times 10^6$ cells/ml into cell culture flasks, cell culture bags or in a preferred embodiment into 1,000 ml (390 cm$^2$) Nexell Lifecell X-Fold Culture Bag or similar with Iscove's Modified Dulbecco's Medium plus 10% Fetal Bovine Serum (FBS) containing cytokines/growth factors. In a preferred embodiment this cytokine/growth factor mixture consists of Stem Cell Factor (50 ng/ml) and Megakaryocyte Growth and Development Factor (10 ng/ml). Steps 3-9 will result in up to $12 \times 10^7$ HP cells or more (as assessed by CD34 positivity) per kg.
Step 9—Transduction Procedure (Preferably Day 8).

The cells are harvested from the first flask, tissue culture bag, including a preferred embodiment of a Lifecell Culture Bag or similar and using the Cytomate device or similar, resuspended in retroviral supernatant (an example of this is a 200 ml aliquot) and transferred into a second tissue culture container, one type of which is the Lifecell X-Fold Culture Bag which have a retrovirus transduction facilitating agent. Such agents include polybrene, protamine sulphate, cationic lipids or in a preferred embodiment, in a tissue culture container that has been pre-coated with RetroNectin at 1-4 mcg/cm$^2$. After 4-10 hours or up to 24 hours, the transfer procedure will be repeated using the CytoMate or similar; for this second transduction cells are either transferred to a new tissue culture container (polybrene, protamine sulphate) or returned to the same or similar RetroNectin-coated container from which they came. In a preferred embodiment, this is done in a fresh aliquot of retroviral supernatant and cultured overnight. In other embodiments this is either not done or repeated several times for similar periods of time. An aliquot of the retroviral supernatant(s) is collected for sterility testing. This will result in up to $6 \times 10^7$ gene-containing HP cells or more (as assessed by CD34 positivity) per kg. This number is determined by a quantitative assay. The transduction efficiency will be at least 0.20%, and preferably in the range from 30-50%, and more preferably greater than 50%.

Step 10—Harvest Cell Product (Preferably on Day 9).

On the morning of day 9, cells are harvested and washed using standard cell centrifuge or automated systems such as the Cytomate samples of cell culture. This will yield up to $5.7 \times 10^7$ gene-containing HP cells or more (as assessed by CD34 positivity) per kg.

Step 11—Infusion Product (Preferably Day 9).

Cells are resuspended in a physiologic infusion buffer containing 5% human serum albumin or similar as carrier. Aliquot samples are removed for sterility (aerobic, anaerobic, fungal, mycoplasma). Infusion product is not released until the results of endotoxin (LAL) and Gram stain testing are available.

Step 12—Infusion of Patient (Preferably Day 9).

The CD34$^+$ cell preparation is administered to the patient pre-medicated as appropriate. In a preferred embodiment, the patient receives a single infusion of $0.5-6 \times 10^7$ transduced CD34$^+$ cells per kilogram of body weight (cells/kg) in the physiologic infusion buffer containing 5% human serum albumin or similar as carrier. The dose of transduced CD34$^+$ cells per patient will depend on the efficiency of each step of the mobilization, apheresis, isolation, culture and transduction procedures. The total number of CD34$^+$ cells (transduced and non-transduced) is determined by cell counting and flow cytometry. The introduced gene-containing HP cells give rise to a chimeric hematopoietic system in which there is a percentage of gene-containing HP cells in the bone marrow. In a preferred embodiment, the one for the treatment of HIV/AIDS, this percentage of gene-containing HP cells is at least 5%, preferably greater than 10% and more preferably than 20%.

Example 5

Use of RNAi with Multiple-Targeting Ability to Inhibit HIV-1 Replication

Figure 14:
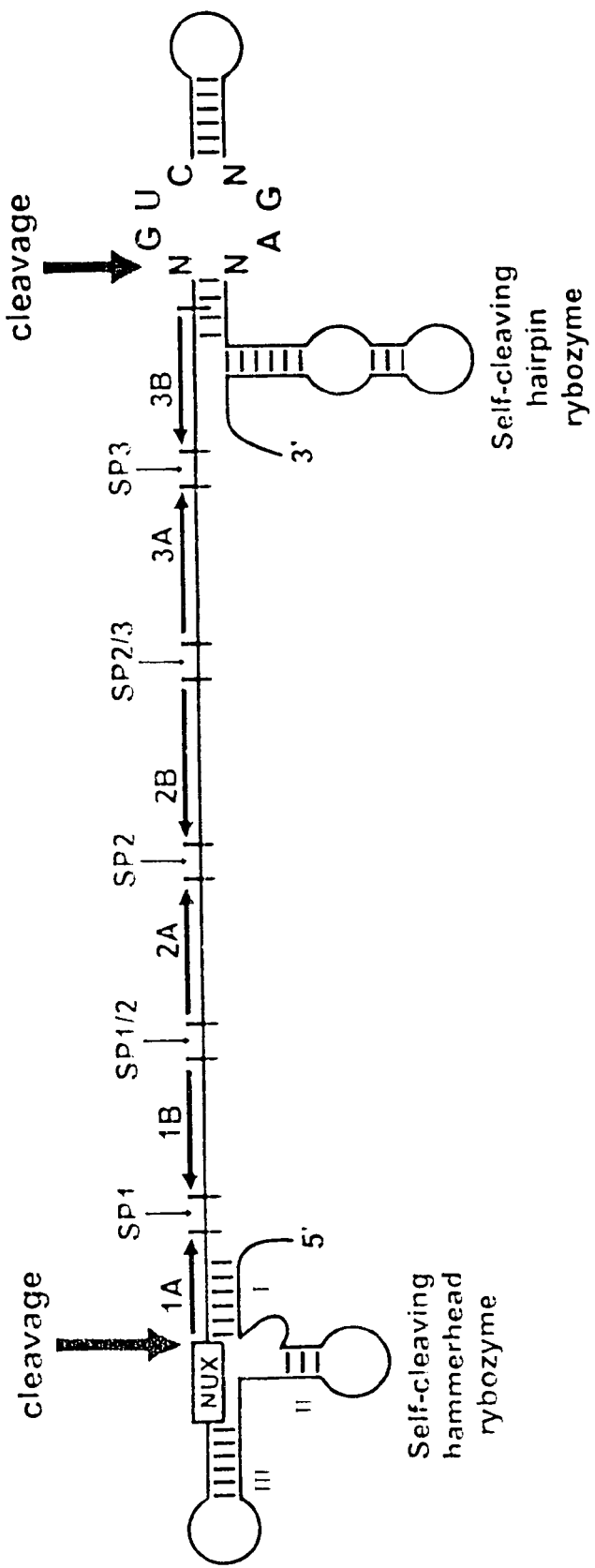
FIG. 14. Schematic design of an RNAi with multiple-targeting ability. The RNA transcript contains three RNAi units each containing sense (1A, 2A, 3A) and antisense (1B, 2B, 3B) segments separated by spacers (SP). The RNAi units are flanked by self cleaving hammerhead and hairpin ribozymes, which cleave at the positions indicated by arrows.

An RNAi construct with multiple-targeting ability against HIV-1 is designed as follows. A cassette is made comprising three RNAi units each having 19-25 nucleotide segments corresponding to HIV-1 in sense orientation (1A, 2A, 3A) and antisense orientation (1B, 2B, 3B) see FIG. 14, such that 1B, 2B and 3B are complementary in sequence to 1A, 2A and 3A, respectively. The sequences 1A, 2A and 3A are selected as being highly conserved in most HIV-1 strains, for example sequence position 5831-5849 (atggagccagtagatccta) (SEQ ID NO. 13), sequence position 5852-5870 (ctagagccctggaagcatc) (SEQ ID NO. 14), and sequence position 5971-5989 (tggcaggaagaagcggaga) (SEQ ID NO. 15) in strain HXB2 or corresponding regions in other strains. The sequences were calculated using the service located at the following web site: hiv-web.lanl.gov/content/hiv-db/NUM-HXB2/HXB2.Nuc.html. The sequences 1A, 2A and 3A preferably differ by not more than 1 nucleotide compared to the corresponding sequences in most HIV-1 strains. Each of the above nineteen nucleotide sequences are reasonably conserved within the tat gene over many HIV subtypes and very well conserved in Subtype B. Each of these nineteen nucleotide sequences have no more than one base pair deviation from the consensus sequence within Subtype B. The first sequence includes the target for Rz2. Differences close to the ends of the sequences may be better tolerated. The RNAi units are separated by spacers which may be 3-7 nucleotides in length. Spacers may be longer, for example comprising intron sequences to aid in cytoplasmic localization of the RNAi units. The cassette is flanked by self-cleaving ribozyme sequences to allow release of the multiple RNAi molecule. For example, the 5' end may be processed by a hammerhead ribozyme where the catalytic domain is designed according to U.S. Pat. No. 6,127,114, and the 3' end by an autocatalytic hairpin ribozyme designed according to U.S. Pat. No. 5,856,188. Such a configuration allows basepaired (blunt) ends to the RNAi molecule without extra nucleotides, although these can be tolerated. Autocatalytic cleavage occurs at the arrowed positions (FIG. 14) to release the 3 RNAi containing molecule. Spacers 1/2 and 2/3 may comprise cleavable sequences, for example sequences cleavable by the hammerhead or hairpin ribozymes or additional ribozyme units, to allow separation of the RNAi units. Clearly, single RNAi units can be used or multimers of up to six or even ten units.

The cassette is assembled as a DNA molecule from overlapping annealed oligonucleotides and inserted into a plasmid vector under the control of a T7 promoter. A recombination-deficient E. coli strain that allows the stable replication of plasmids with inverted repeat sequences, well understood in the art, is used as a cloning host. Longer spacers (eg introns) also assist in this regard. The nucleotide sequence of the DNA insert is confirmed by DNA sequencing. T7 RNA polymerase is used to transcribe the DNA in vitro in the presence of radiolabelled UTP and the self-cleavage ability of the ribozyme units is assayed by electrophoresis of the transcription products on polyacrylamide gels and autoradiography. Self-cleavage occurs at greater than 90% efficiency during transcription at 37° C. for 1 hour. The length and/or sequence of stems and loops in the ribozyme domains can be adjusted if cleavage is less efficient than desired.

The cassette is inserted into the plasmid form of a retroviral vector such as pLNL6 under the control of an RNA polymerase II-dependent promoter. Alternatively, an RNA polymerase III-dependent promoter can be used. The cassette is inserted into a restriction site in the vector in the appropriate orientation. The resultant plasmid is introduced into packaging cell lines such as the AM-12 line and stably transfected cells used to produce retroviral vector. The CemT4 cell line or PBLs are transduced with the retroviral vector and the expression of the RNAi construct determined by RNAse protection assays or reverse transcription-PCR, well understood in the art. Significant protection of the transduced cells is observed after infection with any of several HIV-1 strains. A reduction of p24 production of more than 90% compared to the control (vector without RNAi cassette) is observed, indicating reduced HIV-1 replication.

CD34$^+$ cells are obtained from patients, transduced with the retroviral vector in the presence of RetroNectin by methods as described earlier in this application. At least $0.5 \times 10^6$ transduced CD34$^+$ cells per kg (of weight of the patient) in a total cell population of more than $1.63 \times 10^6$ CD34$^+$ such cells per kg are administered to the patients by infusion. Preferably, more than $5 \times 10^6$ transduced CD34$^+$ cells per kg are administered. These cells engraft the patients' bone marrow and produce protected T-lymphocytes and macrophages/monocytes for more than three years post-infusion. These cells are relatively protected against HIV-1 infection and contribute to improved immune function.

CONCLUDING DISCUSSION

In the clinical trial described herein, the introduction of a gene for expression of an anti-HIV agent into CD34$^+$ cells ex vivo and infusion of these cells into autologous patients was shown to be technically feasible and safe. The presence and expression of the ribozyme construct in peripheral blood lymphoid and myeloid cells was found for at least three years. The degree of cell marking varied in the ten patients treated in this study, and this allowed the following conclusions. The relevant parameters to the degree of cell marking were found to be—the percentage of CD34+ cell transduction, the number of transduced CD34+ cells infused, and the total number of CD34+ cells infused. The actual number of transduced cells was found to be important. The non-transduced cells could play a role in enhancing the survival of the transduced cells in the peripheral blood and organs such as the liver as they are homing to the bone marrow compartment. Prolonged engraftment of transduced CD34+ hematopoietic cells required a minimum dose of $0.52 \times 10^6$ transduced cells in a total CD34+ cell population of at least $1.63 \times 10^6$ cells, in the context of the absence of myeloablative pre-conditioning. There was preferential survival of ribozyme-containing lymphocytes over control lymphocytes, even under relatively low levels of selection. The degree of preferential survival was CD34+ cell dose-dependent, i.e. correlated positively with the number of infused transduced cells, which was unexpected. It is reasonable to expect an even greater degree of preferential survival of ribozyme-protected lymphocytes at higher levels of selection, and greater therapeutic benefit at higher cell doses.

This provides a basis for effective gene therapy of hematopoietic cells for treatment of AIDS/HIV infection and many other diseases. It provides important knowledge for effective quality assurance and evaluation of the procedure in a clinical setting.

| References | | |
|---|---|---|
| Abonour et al | 2000 | Nature Medicine 6: 552-8 |
| Amado et al | 1998 | Human Gene Ther 9: 173-183 |
| Amado and Chen | 1999 | Science 285: 674-676 |
| Amado et al | 1999 | Human Gene Ther 10: 2255-2270 |
| Austin et al | 2000 | Blood 95: 829-36 |
| Autran et al | 1997 | Science 277: 112-116 |
| Bagnis et al | 2002 | Exp Hematol 30: 108-15 |
| Bai et al | 2000 | Molecular Therapy 1: 244-54 |
| Barnett et al | 1998 | Brit J Hematol 102: 553-65 |
| Bazin et al | 1989 | Biochem Pharmacol 38: 109-19 |
| Behringer et al | 1999 | Bone Marrow Transplant 24: 295-302 |
| Benboubker et al | 2001 | Brit J Hematol 113: 247-50 |
| Bender et al | 1987 | J Virol 61: 1639-46 |
| Bender et al | 1991 | Blood 77: 2591-6 |
| Bertolini et al | 1998 | Bone Marrow Transplant 21: S5-7 |
| Bodine et al | 1998 | Ann NY Acad Sci 850: 139-50 |
| Bonyhadi et al | 1997 | J Virol 71: 4704-16. |
| Bordignon et al | 1995 | Science 270: 470-5 |
| Brenner | 2001 | J Int Medicine 249: 345-58 |
| Briones et al | 1999 | Haematologica 84: 483-8 |
| Brooks et al | 2001 | Nature Med 7: 459-64 |
| Bunnell and Morgan | 1998 | Clin Micro Rev 11: 42-56 |
| Bunting et al | 1999 | Ann NY Acad Sci 872: 125-40 |
| Campos | 1993 | Leukemia 7: 1409-15 |
| Case et al | 1999 | Proc Natl Acad Sci USA 96: 2988-93 |
| Carpinteiro et al | 2002 | Int J of Cancer 98: 785-92 |
| Cavazzana-Calvo et al | 2000 | Science 288: 669-672 |
| Cavazzana-Calvo | 2001 | J Gene Med 3: 201-6 |
| Challita and Kohn | 1994 | Proc Natl Acad Sci USA 91: 2567-71 |
| Chang and Roninson | 1996 | Gene 183: 137-42 |
| Chatterjee et al | 1999 | Blood 93: 1882-1894 |
| Cheng et al, | 2000 | Nat Med 6: 1235-40 |
| Cherry et al, | 2000 | Mol Cell Biol 20: 7419-26 |
| Chu et al | 1998 | J Mol Med 76: 184-192 |
| Cohen-Haguenauer et al | 1998 | Hum Gene Ther 9: 207-16 |
| Cornetta et al | 1996 | Hum Gene Ther 7: 1323-30 |
| Crystal | 1995 | Science 270: 404-10 |
| Dao et al | 1997 | Blood 89: 446-56 |
| Dao et al | 1998 | Proc Natl Acad Sci USA 95: 13006-11 |
| Dao et al | 1998 | Blood 92: 4612-21 |
| Dao and Nolta | 1999 | Leukemia 13: 1473-80 |
| Dao and Nolta | 2000 | Leukemia 14: 773-6 |
| Donahue et al | 1998 | Nature Med 4: 181-6 |
| Douek et al | 1998 | Nature 396: 690-695 |
| Ducos et al | 2000 | Gene Ther 7: 1790-4 |
| Dunbar et al | 1995 | Blood 85: 3048-3057 |
| Dunbar et al | 1998a | Hum Gene Ther 9: 2629-40 |
| Dunbar et al | 1998b | Hum Gene Ther 7: 231-53 |
| Dunbar et al | 2001 | Ann NY Acad Sci 938: 236-45 |
| Eglitis and Schneiderman | 1997 | Biochem Biophys Res Commun 231: 477-80 |
| Fan et al, | 2000 | Hum Gene Ther 11: 1313-27 |
| Fehse et al, | 1997 | Hum Gene Ther 8: 1815-24 |
| Feng et al | 1997 | Nature Biotechnol 15: 866-870 |
| Fisher-Adams et al | 1996 | Blood 88: 492-504 |
| Fu and Liesveld | 2000 | Blood Rev 14: 205-18 |
| Gabarre et al | 2000 | The Lancet 355: 1071-2 |
| Gambotto et al | 2000 | Methods Mol Biol 135: 495-508 |

-continued

| References | | |
|---|---|---|
| Gerard et al | 1996 | Hum Gene Ther 7: 343-54 |
| Gervaix et al | 1997 | Hum Gene Ther 8: 2229-38 |
| Giarratana et al | 1998 | Bone Marrow Transpl 22: 707-15 |
| Gitlin et al | 2002 | Nature advance online publicn. June 26, 2002 |
| Glimm et al | 1998 | Hum Gene Ther 9: 771-8 |
| Gluckman | 2000 | Exp Hematol 28: 1197-205 |
| Goerner et al | 1999 | Blood 94: 2287-92 |
| Gothot et al | 1998 | Blood 92: 2641-2649 |
| Grande et al | 1999 | Blood 93: 3276-85 |
| Grimm and Kleinschmidt | 1999 | Hum Gene Ther 10: 2445-2450 |
| Haas et al | 2000 | Mol Ther, 2: 71-80 |
| Hacein-Bey-Abina et al | 2002 | New Eng J Medicine 346: 1185-93 |
| Halene et al | 1999 | Blood 94: 3349-57 |
| Halene and Kohn | 2000 | Hum Gene Ther 11: 1259-67 |
| Hampel et al | 1990 | Nucleic Acids Res 18: 299-304 |
| Hanenberg et al | 1996 | Nat Med 2: 876-82 |
| Hanenberg et al | 1997 | Hum Gene Ther 8: 2193-2206 |
| Hao et al | 1996 | Blood 88: 3306-3313 |
| Harrison | 1980 | Blood 55: 77-81 |
| Harrison et al | 1988 | Proc Natl Acad Sci USA 85: 822-6 |
| Haseloff and Gerlach | 1988 | Nature 334: 585-91 |
| Hennemann et al | 1999 | Exp Hematol 27: 817-825 |
| Herrera et al | 2001 | Brit J Hematol 114: 920-30 |
| Hesforffer et al | 1998 | J Clin Oncol 16: 165-72 |
| Ho | 1993 | Leukemia 7: 1738-46 |
| Ho et al | 1995 | Nature 373: 123-126 |
| Ho et al | 1996 | Blood 88 (suppl 1): 405a |
| Hodgson and Bradley | 1979 | Nature 281: 381-2 |
| Hogan et al | 2002 | Proc Natl Acad Sci USA 99: 413-8 |
| Hoogerbrugge et al | 1996 | Gene Ther 3: 179-183 |
| Huhn et al | 1996 | Exp Hematol 24: 839-47. |
| Huss | 2000 | Stem Cells 18: 1-9 |
| Hutchings et al | 1998 | J Hematother 7: 217-24 |
| Imbert et al | 1998 | Exp Hematol 26: 374-81 |
| Jacque et al | 2002 | Nature advance online publicn June 26, 2002 |
| Jamieson et al | 1999 | Immunity 10: 569-575 |
| Jones et al | 1990 | Nature 347: 188-9 |
| Kansas | 1996 | Blood 88: 3259-87 |
| Kiem et al | 1997 | Blood 90: 4638-4645 |
| Kiem et al | 1998 | Blood 92: 1878-1886 |
| Kirby et al | 2000 | Blood 95: 3710-5 |
| Knaan-Shanzer et al | 2001 | Hum Gene Ther 12: 1989-2005 |
| Knop et al | 1999 | Gene Therapy 6: 373-84 |
| Kobari et al | 2000 | Exp Hematol 28: 1470-80 |
| Kohn | 1995 | Nature Medicine 1: 1017-1023 |
| Kohn et al | 1998 | Nature Medicine 4: 775-780 |
| Kohn et al | 1999 | Blood 94: 368-71 |
| Kramer et al | 1999 | Proc Natl Acad Sci USA 96: 2087-92 |
| Kume et al | 1999 | Int J Hematol 69: 227-33 |
| Lane et al | 1995 | Blood 85: 275-82 |
| Lange and Blankenstein | 1997 | Gene Therapy 4: 303-8 |
| Lataillade et al | 2000 | Blood 95: 756-68 |
| Law et al | 1999 | Exp Hematol 27: 147-54 |
| LeDoux et al | 2001 | Hum Gene Ther 12: 1611-21 |
| Lee et al | 1994 | J Virol 68: 8254-64 |
| Lewis and Verfaillie | 2000 | Exp Hematol 28: 1087-95 |
| Lieber et al | 1999 | J Virol 73: 9314-24 |
| Lisziewicz et al | 1993 | Proc Natl Acad Sci USA 90: 8000-4 |
| Liu et al | 1999 | Hum Gene Ther 10: 2337-46 |
| Lyman and Jacobsen | 1998 | Blood 91: 1101-34 |
| Maciejewski et al | 1995 | Nature Med 1: 667-73 |
| Malech et al | 1997 | Proc Natl Acad Sci USA 94: 12133-8 |
| Malik et al | 1995 | Blood 86: 2993-3005 |
| Marandin et al | 1996 | Blood 88: 4568-78 |
| Marasco et al | 1998 | Human Gene Ther 9: 1627-42 |
| Marini et al | 2000 | Caner Gene Ther 7: 816-25 |
| Martinez et al | 1999 | Exp Hematol 27: 561-8 |
| Mautino and Morgan | 2002 | AIDS Patient Care and Stds 16: 11-26 |
| Michallet et al | 2000 | Exp Hematol 28: 858-70 |
| Michienzi et al | 2000 | Proc Natl Acad Sci USA 97: 8955-60 |
| Miller | 1986 | Beyond ANOVA; New York; John Wiley and Sons |
| Miller and Buttimore | 1986 | Mol Cell Biol 6: 2895-902 |
| Miyoshi et al | 1999 | Science 283: 682-686 |
| Moore and MacKenzie | 1999 | Prog Exp Tumor Res 36: 20-49 |
| Mountain | 2000 | TIBTECH 18: 119-128 |
| Murray et al | 1999 | Exp Hematol 27: 1019-28 |
| Murray et al | 2000 | Hum Gene Ther 11: 2039-50 |
| Nagler et al | 2000 | Exp Hematol 28: 1096-104 |

References -continued

| | | |
|---|---|---|
| Naldini et al | 1996 | Science 272: 263-7 |
| Newbound et al | 2001 | Exp Hematol 29: 163-73 |
| Ng et al | 2002 | Brit J Hematol 117: 226-37 |
| Nolta et al | 1992 | Exp Hematol 20: 1065-1071 |
| Novina et al | 2002 | Nature advance online publicn June 3, 2002 |
| Ogawa et al | 1993 | Blood 81: 2844-2853 |
| Ojwang et al | 1992 | Proc Natl Acad Sci USA 89: 10802-6 |
| Omori et al | 1999 | J Hematother Stem Cell Res 8: 503-14 |
| Orlic and Bodine | 1994 | Blood 84: 3991-3994 |
| Orlic et al | 1999 | Ann NY Acad Sci 872: 115-24 |
| Orlic et al | 2001 | Ann NY Acad Sci 938: 221-230 |
| Ostrowski et al | 1999 | J Virol 73: 6430-5 |
| Quan et al | 1999 | Exp Hematol 27: 1511-8 |
| Pakker et al | 1998 | Nature Medicine 4: 208-14 |
| Parkman | 1986 | Science 232: 1373-78 |
| Peters et al | 1996 | Blood 87: 30-7 |
| Picker et al | 1993 | J Immunol 150: 1105-21 |
| Poulin et al | 1999 | J Exp Med 190: 479-86 |
| Ragg et al | 2000 | Cancer Res 60: 5187-95 |
| Ramezani et al | 2002 | Frontiers in Bioscience 7: A29-36 |
| Ranga et al | 1998 | Proc Natl Acad Sci USA 95: 1201-6 |
| Reese et al | 1999 | J Hematother Stem Cell Res 8: 515-23 |
| Reis | 1999 | Transplant Proc 31: 2970-2 |
| Relander et al | 2001 | J Gene Med 3: 207-18 |
| Relander et al | 2002 | J Gene Med 4: 122-32 |
| Richter and Karlson | 2001 | Int J Hematol 73: 162-69 |
| Rivella et al | 2000 | J Virology 74: 4679-87 |
| Robbins et al | 1998 | Proc Natl Acad Sci USA 95: 10182-7 |
| Roe et al | 1993 | EMBO J 12: 2099-2108 |
| Rosler et al | 2000 | Exp Hematol 28: 841-52 |
| Rossi et al | 1992 | AIDS Res and Human Retroviruses 8: 183-9 |
| Rovira et al | 2000 | Blood 96: 4111-7 |
| Sadelain et al | 2000 | Curr Opin Hematol 7: 364-77 |
| Sanders et al | 1988 | Immunol Today 9: 195-9 |
| Sandhaus et al | 1998 | Exp Hematol 26: 73-8 |
| Sanyal and Schuening | 1999 | Hum Gene Ther 10: 2859-68 |
| Sarver et al | 1990 | Science 247: 1222-5 |
| Sato et al | 1999 | Blood 94: 2548-2554 |
| Saylors et al | 1999 | Gene Ther 6: 944-6 |
| Schilz et al | 1998 | Blood 92: 3163-71 |
| Schilz et al | 2000 | Mol Ther 2: 609-18 |
| Schilz et al | 2001 | J Gene Med 3: 427-36 |
| Sczakiel and Pawlita | 1991 | J Virol 65: 468-72 |
| Shaheen et al | 1996 | J Virol 70: 3392-400 |
| Siena et al | 1989 | Blood 74: 1905-14 |
| Smythe et al | 1994 | Proc Natl Acad Sci USA 91: 3657-61 |
| Solar et al | 1998 | Blood 92: 4-10 |
| Strayer et al | 2000 | Gene Ther 7: 886-95 |
| Su et al | 1997 | Blood 89: 2283-90 |
| Sun et al | 1995 | Proc Natl Acad Sci USA 92: 7272-6 |
| Sun et al | 1995 | Nucl Acids Research 23: 2909-13 |
| Sun et al | 1996 | Nucl Acids Mol Biol Catalytic RNA 10: 329-342 |
| Sutton et al | 1998 | J Virol 72: 5781-8 |
| Takatoku et al | 2001 | J Clinical Investig 108: 447-55 |
| Takenaka et al | 2000 | PNAS 97: 7515-20 |
| Takiyama et al | 1998 | Eur J Hematol 61: 1-6 |
| Tavolini | 1997 | Gene Ther 4: 150-5 |
| Thomas et al | 1999 | Methods 17: 202-18 |
| To et al | 1997 | Blood 85: 2233-58 |
| Traycoff et al | 1998 | Exp Hematol 26: 53-62 |
| Uchida et al | 1998 | Proc Natl Acad Sci USA 95: 1939-44 |
| Vassilopoulos et al | 2001 | Blood 98: 604-609 |
| Veres et al | 1998 | J Virol 72: 1894- |
| Verfaillie et al | 2000 | Exp Hematol 28: 1071-9 |
| Vignoli et al | 1998 | AIDS 12: 999-1005 |
| von Laer et al | 1998 | J Virol 72: 1424-30 |
| Wang et al | 1998 | Human Gene Ther 9: 1283-91 |
| Ward et al | 1998 | American J Pathology 153: 373-379 |
| Wilcox et al | 2000 | Blood 95: 3645-52 |
| Williams et al | 1999 | Ann NY Acad Sci 872: 109-13 |
| Yu et al | 1995 | Proc Natl Acad Sci USA 92: 699-703 |
| Zanjani et al | 1998 | Exp Hematol 26: 353-60 |
| Zauli et al | 1996 | J Exp Med 183: 99-108 |
| Zhang et al | 1999 | J Exp Med 190: 725-32 |
| Zhang et al | 1998 | Proc Natl Acad Sci USA 95: 1154-9 |
| Zimmermann et al | 1995 | Bone Marrow Transpl 9: 439-44 |

What is claimed is:

1. A process of making a composition comprising:
   a) mobilizing CD34+ hematopoietic progenitor cells into the blood of a human subject by administering to the subject an amount of one or more cytokines sufficient to mobilize the hematopoietic cells;
   b) isolating by apheresis leukocytes from the blood of the subject of step a);
   c) isolating the CD34+ hematopoietic cells from the isolated leukocytes of step b);
   d) culturing the isolated CD34+ hematopoietic cells of step c) in the presence of a mixture of cytokines and growth factors;
   e) subjecting the CD34+ hematopoietic cells of step d) to a transduction process with a viral vector containing a gene of interest in the presence of an agent that colocalizes the cells with the gene of interest;
   f) recovering the CD34+ hematopoietic cells of step e);
   g) determining the number of transduced CD34+ hematopoietic cells and the total number of CD34+ hematopoietic cells present in the product of step f); and
   h) if the number of transduced CD34+ hematopoietic cells of step g) is at least $0.52 \times 10^6$ cells per kg of body weight of the human subject, based on a determination by competitive PCR of the CD34+ hematopoietic cells, and the total number of CD34+ hematopoietic cells is at least $1.63 \times 10^6$ cells per kg of body weight of the human subject, then formulating the composition to be ready for delivery into a human subject, otherwise again performing steps a)-f) and combining the recovered CD34+ hematopoietic cells prior to step g).

2. The process of claim 1, wherein the agent that colocalizes the cells with the gene of interest is a recombinant fragment of fibronectin.

3. The process of claim 2, wherein the recombinant fragment of fibronectin is the CH296 fragment of human fibronectin.

4. The process of claim 1, wherein the step of mobilizing CD34+ hematopoietic progenitor cells in the subject is performed by administering to the subject an amount of a form of G-CSF sufficient to mobilize the hematopoietic cells.

5. The process of claim 1, wherein in the step of isolating the leukocytes from the subject's blood, apheresis is performed at least twice.

6. The process of claim 1, wherein in the step of culturing the isolated CD34+ hematopoietic cells, the mixture of cytokines and growth factors comprises Stem Cell Factor (SCF) and Megakaryocyte Growth and Development Factor (MGDF).

7. The process of claim 1, wherein the human subject is an adult human subject.

8. The process of claim 1, wherein the gene of interest encodes an anti-HIV agent.

9. The process of claim 8, wherein the anti-HIV agent is an RNA.

10. The process of claim 8, wherein the anti-HIV agent is an RNAi molecule.

11. The process of claim 8, wherein the anti-HIV agent is an antisense molecule.

12. The process of claim 8, wherein the anti-HIV agent is a ribozyme.

13. The process of claim 12, wherein the anti-HIV agent is a ribozyme encoded by DNA comprising nucleotides having the sequence 5'-TTA GGA TCC TGA TGA GTC CGT GAG GAC GAA ACT GGC TC-3' (SEQ ID NO. 3).

14. The process of claim 1, wherein in step h), if the number of transduced CD34+ hematopoietic cells is less than $0.52 \times 10^6$ cells per kg of body weight of the human subject or the total number of CD34+ hematopoietic is less than $1.63 \times 10^6$ cells per kg of body weight of the human subject, then further including a step of cryogenically storing the CD34+ hematopoietic cells recovered in step f), repeating steps a)-f), and combining cryogenically stored cells with the cells recovered from step f).

15. A process of making a composition comprising:
   a) mobilizing CD34+ hematopoietic progenitor cells into the blood of a human subject by administering to the subject an amount of one or more cytokines sufficient to mobilize the hematopoietic cells;
   b) isolating by apheresis leukocytes from the blood of the subject of step a);
   c) isolating the CD34+ hematopoietic cells from the isolated leukocytes of step b);
   d) culturing the isolated CD34+ hematopoietic cells of step c) in the presence of a mixture of cytokines and growth factors;
   e) subjecting the CD34+ hematopoietic cells of step d) to a transduction process with a viral vector containing a gene of interest in the presence of an agent that colocalizes the cells with the gene of interest;
   f) recovering the CD34+ hematopoietic cells of step e);
   g) determining the number of transduced CD34+ hematopoietic cells and the total number of CD34+ hematopoietic cells present in the product of step f); and
   h) if the number of transduced CD34+ hematopoietic cells of step g) is at least $0.5 \times 10^6$ cells per kg of body weight of the human subject, based on a determination by competitive PCR of the CD34+ hematopoietic cells, and the total number of CD34+ hematopoietic cells is at least 1.7×10⁶ cells per kg of body weight of the human subject, then preparing the composition, otherwise again performing steps a)-f) and combining the recovered CD34⁺ hematopoietic cells prior to step g).

16. The process of claim 15, wherein the gene of interest encodes an anti-HIV agent.

17. The process of claim 16, wherein the anti-HIV agent is an RNA.

18. The process of claim 16, wherein the anti-HIV agent is an antisense molecule.

19. The process of claim 16, wherein the anti-HIV agent is a ribozyme.

20. The process of claim 19, wherein the anti-HIV agent is a ribozyme encoded by DNA comprising nucleotides having the sequence 5'-TTA GGA TCC TGA TGA GTC CGT GAG GAC GAA ACT GGC TC-3' (SEQ ID NO. 3).

21. The process of claim 15, wherein in step h), if the number of transduced CD34⁺ hematopoietic cells is less than 0.5×10⁶ cells per kg of body weight of the human subject or the total number of CD34⁺ hematopoietic cells is less than 1.7×10⁶ cells per kg of body weight of the human subject, then further including a step of cryogenically storing the CD34⁺ hematopoietic cells recovered in step f), repeating steps a)-f), and combining cryogenically stored cells with the cells recovered from step f).

22. The process of claim 1, wherein the viral vector is a retroviral vector.

23. The process of claim 15, wherein the viral vector is a retroviral vector.

24. The process of claim 15, wherein the agent that colocalizes the cells with the gene of interest is a recombinant fragment of fibronectin.

25. The process of claim 15, wherein the recombinant fragment of fibronectin is the CH296 fragment of human fibronectin.

26. The process of claim 15, wherein the step of mobilizing CD34⁺ hematopoietic progenitor cells in the subject is performed by administering to the subject an amount of a form of G-CSF sufficient to mobilize the hematopoietic cells.

27. The process of claim 15, wherein in the step of isolating the leukocytes from the subject's blood, apheresis is performed at least twice.

28. The process of claim 15, wherein in the step of culturing the isolated CD34⁺ hematopoietic cells, the mixture of cytokines and growth factors comprises Stem Cell Factor (SCF) and Megakaryocyte Growth and Development Factor (MGDF).

29. The process of claim 15, wherein the human subject is an adult human subject.

* * * * *

SEQUENCE LISTING

<160> NUMBER OF SEQ ID NOS: 15

<210> SEQ ID NO 1
<211> LENGTH: 39
<212> TYPE: RNA
<213> ORGANISM: Artificial Sequence
<220> FEATURE:
<223> OTHER INFORMATION: ribozyme

<400> SEQUENCE: 1
uuaggauccu gaugaguccg ugaggacgaa acuggcucc                      39

<210> SEQ ID NO 2
<211> LENGTH: 17
<212> TYPE: RNA
<213> ORGANISM: Human immunodeficiency virus

<400> SEQUENCE: 2
ggagccagua gauccua                                              17

<210> SEQ ID NO 3
<211> LENGTH: 38
<212> TYPE: DNA
<213> ORGANISM: Artificial Sequence
<220> FEATURE:
<223> OTHER INFORMATION: DNA encoding a ribozyme

<400> SEQUENCE: 3
ttaggatcct gatgagtccg tgaggacgaa actggctc                       38

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
cactcatgag atgcctgcaa g                                         21

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
gagttctacc ggcagtgcaa a                                         21

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
gatcccctcg cgagttggtt ca                                        22

<210> SEQ ID NO 7
<211> LENGTH: 20
<212> TYPE: DNA
<213> ORGANISM: Artificial Sequence
<220> FEATURE:

<223> OTHER INFORMATION: primer

<400> SEQUENCE: 7
ctatgtgatc tggtcggaga                                                    20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
ccacaggcaa ctttagagca                                                    20

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9
tggcaatgaa agcaacact                                                     19

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
tttagaggag cttaagaatg a                                                  21

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
agttttaggc tgacttcctg g                                                  21

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
tggaagccat aataagaat                                                     19

<210> SEQ ID NO 13
<211> LENGTH: 19
<212> TYPE: DNA
<213> ORGANISM: HIV-1

<400> SEQUENCE: 13
atggagccag tagatccta                                                     19

<210> SEQ ID NO 14
<211> LENGTH: 19
<212> TYPE: DNA

```
<213> ORGANISM: HIV-1

<400> SEQUENCE: 14
ctagagccct ggaagcatc                                               19

<210> SEQ ID NO 15
<211> LENGTH: 19
<212> TYPE: DNA
<213> ORGANISM: HIV-1

<400> SEQUENCE: 15
tggcaggaag aagcggaga                                               19
```